(12) United States Patent
Grima Poveda et al.

(10) Patent No.: US 8,022,218 B2
(45) Date of Patent: *Sep. 20, 2011

(54) 4-PHENYL-5-OXO-1,4,5,6,7,8-HEXAHYDRO-QUINOLINE DERIVATIVES FOR THE TREATMENT OF INFERTILITY

(75) Inventors: Pedro Manuel Grima Poveda, Oss (NL); Willem Frederik Johan Karstens, Oss (NL); Cornelis Marius Timmers, Oss (NL)

(73) Assignee: N.V. Organon, Oss (NL)

( * ) Notice: Subject to any disclaimer, the term of this patent is extended or adjusted under 35 U.S.C. 154(b) by 805 days.

This patent is subject to a terminal disclaimer.

(21) Appl. No.: 11/912,736

(22) PCT Filed: May 2, 2006

(86) PCT No.: PCT/EP2006/061972
§ 371 (c)(1),
(2), (4) Date: Oct. 26, 2007

(87) PCT Pub. No.: WO2006/117368
PCT Pub. Date: Nov. 9, 2006

(65) Prior Publication Data
US 2008/0275042 A1    Nov. 6, 2008

(30) Foreign Application Priority Data
May 4, 2005    (EP) .................................. 05103735

(51) Int. Cl.
*C07D 215/04*    (2006.01)
(52) U.S. Cl. ........................................................ 546/173
(58) Field of Classification Search .................. 546/165, 546/173; 544/128
See application file for complete search history.

(56) References Cited

U.S. PATENT DOCUMENTS

| 5,455,253 | A | * | 10/1995 | Ohnmacht et al. | ............ | 514/311 |
| 5,622,964 | A | * | 4/1997 | Ohnmacht et al. | ............ | 514/311 |
| 6,087,503 | A | | 7/2000 | Furuya et al. | | |
| 6,194,428 | B1 | | 2/2001 | Urbahns et al. | | |
| 2008/0262033 | A1 | | 10/2008 | Karstens et al. | | |
| 2008/0300270 | A1 | | 12/2008 | Timmers et al. | | |
| 2009/0215773 | A1 | | 8/2009 | Van Straten et al. | | |

FOREIGN PATENT DOCUMENTS

| DE | 1070162 | 12/1959 |
| EP | 0 755 931 | 1/1997 |
| JP | 2003026630 | 1/2003 |
| WO | WO 94/08966 | 4/1994 |
| WO | WO 96/06610 | 3/1996 |
| WO | WO 00/08015 | 2/2000 |
| WO | WO 00/78768 | 12/2000 |
| WO | WO 02/09706 | 2/2002 |
| WO | WO 03/004028 | 1/2003 |
| WO | WO 2004/056779 | 7/2004 |

OTHER PUBLICATIONS

Altmayer, et al., "Propofol Binding to Human Blood Proteins", *Arzneim.-Forsch./Drug Res.* (1995) 45: 1053-1056.
Anelli et al., "Smiles Rearrangement as a Tool for the Preparation of 5-[(2-Hydroxyacyl)amino]-2,4,6-thiodo-1,3-benzenedicarboxamides: Main Pathway and Side Reactions," *Tetrahedron* (1997) 53:11919-11928.
Aranyos, et al., "An Application of the Stille Coupling for the Preparation of Arylated Phthalonitriles and Phthalocyanines", *Acta Chem. Scand.* (1999) 53: 714-720.
Bahner, et al., "Halogenated Aminobenzaldehydes and Aminostyrylquinolines", *J. Org. Chem*, 25 (1960) 2053-2055.
Baker, William R. "Alkoxide-Accelerated Smiles Rearrangements. Synthesis of N-(2-Hydroxyethyl)anilines from N-(2-Hydroxyethyl)(aryloxy)acetamides," *J. Org. Chem.* (1983) 48: 5140-5143.
Bierbaum et al., "Hypotensive 1,2,4-Benzothiadiazines," *J. Med. Chem.* (1963) 6: 272-275.
Claiborne et al., "Orally Efficacious NR2B-Selective NMDA Receptor Antagonists," *Bioorg. & Med. Chem. Lett.* 13:697-700, 2003.
Crich, et.al., "Enantiospecific Synthesis with Amino Acids. Part 2. a-Alkylation of Tryptophan: A Chemical and Computational Investigation of Cyclic Tryptophan Tautomers", *J. Chem. Soc. Perkin Trans.* 2 (1992) 2233-2240.
Devroey, et al., "Successful in-vitro fertilisation and embryo transfer after treatment with recombinant human FSH", *Lancet* 339 (1992) 1170-1171.
Dondoni et al., "Two- and Three-Component Hantzsch Reaction Using C-Glycosylated Reagents. Approach to the Asymmetric Synthesis of 1,4-Dihydropyridines", *Synlett* (2002) 89-92.
Dorrington & Armstrong, "Effects of FSH on Gonadal Functions", *Recent Prog. Horm. Res.*, 35 (1979) 301-342.
Dow, et al., "Discovery of a Novel Series of 6-Azauracil-Based Thyroid Hormone Receptor Ligands:Potent, Tβ Subtype-Selective Thyromimetics", *Bioorg. & Med. Chem. Lett.* 13 (2003) 379-382.
Drizin, et al., "Structure-Activity Studies for a Novel Series of Tricyclic Dihydropyrimidines as KATP Channel Openers (KCOs)", *Bioorg. & Med. Chem. Lett.* 12 (2002) 1481-1484.
Eisner, et al., "The Chemistry of Dihydropyridines", *Chem. Rev.* 72 (1972) 1-42.
Fisher, et al., "Heteroatom-Directed Metalation. Lithiation of N-Propenylbenzamides and N-Propenyl-o-toluamides. Novel Routes to Ortho-Substituted Primary Benzamide Derivatives and N-Unsubstituted Isoquinolin-I(2H)-ones", *J. Org. Chem.* 57 (1992) 2700-2705.

(Continued)

*Primary Examiner* — Nizal Chandrakumar
(74) *Attorney, Agent, or Firm* — Janet E. Fair; John C. Todaro

(57) ABSTRACT

The present invention relates to 4-phenyl-5-oxo-1,4)5,6,7,8-hexahydroquinoline derivatives according to Formula I, Formula I or a pharmaceutically acceptable salt thereof, wherein $R^1$ is (1-6C)alkyl, (2-6C)alkenyl or (2-6C)aDcynyl; $R^2$, $R^3$ are independently halogen, (1-4C)allcyl, (2-4C)alkenyl, (2-4C)-alkynyl, (1-4C)aBcoxy, (3-4C)alkenyloxy or (3-4C)alkynyloxy; $R^4$ is phenyl or (2-5C)-heteroaryl, both substituted with $R^7$ and optionally substituted on the (hetero)aromatic ring with one or more substituents selected from hydroxy, amino, halogen, nitro, trifluoromethyl, cyano, (1-4C)alkyl, (1-4C)alkoxy, (1-4C)alkylthio and (di)(1-4C)-alkylamino. The invention also relates to pharmaceutical compositions comprising said derivatives, as well as to the use of these 4-phenyl-5-oxo-1,4,5,6,7,8-hexahydro-quinoline derivatives in therapy, more specifically for the treatment of infertility.

14 Claims, 1 Drawing Sheet

OTHER PUBLICATIONS

Fukuyama, et al., "2,4-Dinitrobenzenesulfonamides: A Simple and Practical Method for the Preparation of a Variety of Secondary Amines and Diamines", *Tetrahedron Lett.* 38 (1997) 5831-5834.

Greiner, A., "TDA-1 Catalysis in Smiles Rearrangement of N-Arylphenoxyamides. Accelerating Effect of the 2,4,6-Trichloro Substitution," *Tetrahedron Lett.* 30:931-934, 1989.

Guilford, et al., "Synthesis, Characterization, and Structure-Activity Relationships of Amidine-Substituted (Bis)benzylidene-Cycloketone Olefin Isomers as Potent and Selective Factor Xa Inhibitors," *J. Med. Chem.* 42:5415-5425, 1999.

Guo, et al., "Enantioselective Addition of Diethylzinc to Benzaldehyde Catalyzed by Chiral Titanate Complexes with Helical Ligands", *Tetrahedron* 53 (1997) 4145-4158.

Harvey, et al., "o-Nitroaniline Derivatives. Part 11. 4- and 7-Amino-1H-benzimidazole 3-Oxides", *J. Chem. Soc. Perkin Trans.* 1 (1988) 1939-1943.

Insler, V., "Gonadotropin Therapy: New Trends and Insights", *Int. J. Fertil.*, 33 (1988) 85-97.

Jia, et al., "Expression of Human Luteinizing Hormone (LH) Receptor: Interaction with LH and Chorionic Gonadotropin from Human but not Equine, Rat, and Ovine Species", *Mol. Endocrinol.* 5 (1991) 759-768.

Kansal, et al., "Diuretic Agents: Synthesis of 1,2-Disubstituted 7-Sulphamoylbenzimidazole-5-Carboxylic Acids," *Indian J. Chem.* 18B:88-90, 1979.

Katsumi, et al., "Studies on Styrene Derivatives. I. Synthesis and Antiinflammatory Activities of a-Benzylidene-γ-butyrolactone Derivatives", *Chem. Pharm. Bull.* 34 (1986) 121-129.

Kesten, et al., "Synthesis and Antimalarial Properties of 1-Imino Derivatives of 7-Chloro-3-substituted-3,4-dihydro-1,9(2H,10H)-acridinediones and Related Structures", *J. Med. Chem.* 35 (1992) 3429-3447.

Krohn, et al., "Total Synthesis of Angucyclines. Part 15: A Short Synthesis of (±)-6-Deoxybrasiliquinone B", *Tetrahedron* 56 2000 4753-4758.

Kuehne, et al., "1,4-Dihydrobenzoic Acid", *Org. Synth. Coll.* 5 (1973) 400.

Kumar, et al., "Synthesis and Evaluation of Anticancer Benzoxazoles and Benzimidazoles Related to UK-1", *Bioorg. & Med. Chem.* 10 (2002) 3997-4004.

Lal, et al., "Regiospecific Oxidation by DDQ of Unhindered Alkyl Groups in Sterically Hindered Aromatic Amines", *Tetrahedron Lett.* 25 (1984) 2901-2904.

Langry, K.C., "Synthesis of Imidazoquinolines and Imidazoisoquinolines From Azanaphthalene Carboxylic Acids", *Org. Prep. Proced. Int.* 26 (1994) 429-438.

Larget, et.al. "A Convenient Extension of the Wessely-Moser Rearrangement for the Synthesis of Substituted Alkylaminoflavones as Neuroprotective Agents In Vitro", *Bioorg. & Med. Chem. Lett.* 10 (2000) 835-838.

Lavilla, R., "Recent developments in the chemistry of dihydropyridines", *J. Chem. Soc., Perkin Trans.* 1 (2002) 1141-1156.

Loev, et al., "Hantzsch-Type Dihydropyridine Hypotensive Agents", *J. Med. Chem.* 17 (1974) 956-965.

Manchand, et al., "Synthesis of 3,4,5-Trimethoxybenzaldehyde", *Synth. Commun.* 20 (1990) 2659-2666.

Mariella, et al., "Synthesis of Some Aromatic Malononitriles", *J. Org. Chem.* 23 (1958) 120-121.

Mayer, et.al., "Über Carbocyclische Reduktone. Dihyrogpyogallol und Dihydrogallussäure", *Chem. Ber.* 88 (1955) 316-327.

McCarthy, et al., "Synthesis and Renal Vasodilator Activity of 2-Chlorodopamine and N-Substituted Derivatives," *J. Med. Chem.* 29: 1586-1590 (1986).

Miri, et al., "Synthesis and Calcium Channel Modulating Effects of Modified Hantzsch Nitrooxyalkyl 1,4-Dihydro-2,6-dimethyl-3-nitro-4-(pyridinyl or 2-trifluoromethylphenyl)-5-pyridinecarboxylates", *Drug Dev. Res.* 51 (2000) 225-232.

Mitchell, et al., "N-Bromosuccinimide-Dimethylformamide: A Mild, Selective Nuclear Monobromination Reagent for Reactive Aromatic Compounds", *J. Org. Chem.* 44 (1979) 4733-4735.

Morse, et al., "Hetrogeneity of Proteins in Commercial Preparations of Human Chorionic Gonadotropin (hCG) Demonstrated by Western Blotting", *Amer. J. Reproduct. Immunol. and Microbiology* 17 (1988) 134-140.

Navot, et al., "The Use of Follicle-Stimulating Hormone for Controlled Ovarian Hyperstimulation in In Vitro Fertilization", *J. In Vitro Fert. Embryo Transf.* 5 (1988) 3-13.

Nguyen, et al., "Hantzsch 1,4-Dihydropyridines Containing a Nitrooxyalkyl Ester Moiety to Study Calcium Channel Antagonist Structure-Activity Relationships and Nitric Oxide Release", *Drug Dev. Res.* 51 (2000) 233-243.

Nobel, D., "The Copper-Carbon Dioxide System, a New Mild and Selective Catalyst for the Methoxylation of Non-activated Aromatic Bromides", *J. Chem. Soc., Chem. Commun.* 4 (1993) 419-420.

Novak, et al, :Hydrolysis and $Fe^{2+}$-Induced Reduction of N-Aryl-O-pivaloylhydroxylamines: Aqueous Solution Chemistry of Model Carcinogens, *J. Org. Chem.* 53 (1988) 4762-4769.

Olijve, et al., "Molecular Biology and Biochemistry of Human Recombinant Follicle Stimulating Hormone (Puregon®)", *Mol. Hum. Reprod.* 2 (1996) 371-382.

Olson, et al., "A Dopamine Receptor Model and Its Application in the Design of a New Class of Rigid Pyrrolo[2,3-g]isoquinoline Antipsychotics", *J. Med. Chem.* 24 (1981) 1026-1034.

Raviña, et al., "Conformationally Constrained Butyrophenones with Affinity for Dopamine (D1, D2, D4) and Serotonin (5-HT2A, 5-HT2B, 5-HT2C) Receptors: Synthesis of Aminomethylbenzo[b]furanones and Their Evaluation as Antipsychotics", *J. Med. Chem.* 43 (2000) 4678-4693.

Sainani, et al., "Synthesis of 4-aryl-1,4,5,6,7,8-hexahydro-5-oxo-2,7,7-trimethylquinoline-3-carboxylates and amides", *Indian J. Chem.* 33B (1994) 526-531.

Sarma, et al., "Solid State Nuclear Bromination with N-Bromosuccinimide. Part 2. Experimental and theoretical studies of reactions with some substituted benzaldehydes", *J. Chem. Soc., Perkin Trans.* 2, (2000) 1119-1124.

Sarma, et al., "Solid State Nuclear Bromination with N-bromosuccinimide. Part 1. Experimental and theoretical studies on some substituted aniline, phenol and nitro aromatic compounds", *J. Chem. Soc., Perkin Trans.* 2, (2000) 1113-1118.

Shadyro et al, "Synthesis and Antiviral Activity of N-Acyl Derivatives of 4,6-Di-(*tert*-Butyl)-2-Aminophenor", *Pharm. Chem. J.*, 36 (2002) 410-412.

Sharma, et al., "Syntheses of Some Mannich Bases of Formyl & Other Substituted Phenols as Potential Spermicides", *Indian J. Chem.*, 20B (1981) 1010-1013.

Sharpe, R.M., "Intratesticular Control of Steroidogenesis", *Clin. Endocrinol.*, 33 (1990) 787-807.

Shilcrat, et al., "A New Regioselective Synthesis of 1,2,5-Trisubstituted 1H-Imidazoles and Its Application to the Development of Eprosartan ," *J. Org. Chem.* 62:8449-8454, 1997.

Sircar, et al., "Calcium Channel Blocking and Positive Inotropic Activities of Ethyl 5-Cyano-1,4-dihydro-6-methyl-2-[(phenylsulfonyl)methyl]-4-aryl-3-pyridine-carboxylate and Analogues. Synthesis and Structure-Activity Relationships", *J. Med. Chem.*, 34 (1991) 2248-2260.

Stratowa, et al., "Use of a luciferase reporter system for characterizing G-protein-linked receptors", *Curr. Opin. Biotechnol.*, 6 (1995) 574-581.

Theilacker, et al.,"Zur Konstitution der Triacylmethane. II. Über das Bicyclo-[2,2,2]-octantrion-(2,6,7)", *Justus Liebig's Annalen der Chemie*, 570 (1950) 15-33.

Turconi, et al., "Synthesis of a New Class of 2,3-Dihydro-2-oxo-1H-benzimidazole-1-carboxylic Acid Derivatives as Highly Potent 5-HT3 Receptor Antagonists", *J. Med. Chem.*, 33 (1990) 2101-2108.

Vierhapper, et al., "Zur Sauerstoffoxidation von Kreosolderivaten in alkalisch-wäßriger Lösung", *Monatsh. Chem.*, 106 (1975) 1191-1201.

Visentin, et al. "Synthesis and Voltage-Clamp Studies of Methyl 1,4-Dihydro-2,6-dimethyl-5-nitro-4-(benzofurazanyl)pyridine-3-carboxylate Racemates and Enantiomers and of Their Benzofuroxanyl Analogues," *J. Med. Chem.*, 42 (1999) 1422-1427.

Vitolina, et al. "Synthesis and Study of the pharmacological activity of derivatives of condensed 1, 4-dihydropyridines," *Khimiko-Farmatsevticheskii Zhurnal*, 15 (1981) 39-42.

Wadia, et al., "A Convenient Preparation of N-Alkyl and N-Arylamines by Smiles Rearrangement—Synthesis of Analogues of Diclofenac," *Synth. Commun.*, 33:2725-2736, 2003.

White, et al., "Resistance-Modifying Agents. 9. Synthesis and Biological Properties of Benzimidazole Inhibitors of the DNA Repair Enzyme Poly(ADP-ribose) Polymerase", *J. Med. Chem.*, 43 (2000) 4084-4097.

Wong, et al., "Identification of a Dihydropyridine as a Potent α1a Adrenoceptor-Selective Antagonist That Inhibits Phenylephrine-Induced Contraction of the Human Prostate", *J. Med. Chem.*, 41 (1998) 2643-2650.

Yagupolskii, et al., "Vasorelaxation by New Hybrid Compounds Containing Dihydropyridine and Pinacidil-Like Moieties", *J. Med. Chem.*, 42 (1999) 5266-5271.

Database CAPLUS Chemical Abstracts Service, Columbus, Ohio, US; XP-002288485 retrieved from STN accession No. 1802 Database accession No. 1981:497547.

XP-002369583 Retrieved from STN, Database Registry [Online] RN:330674-72-1, Apr. 10, 2001.

Search Report issued on May 12, 2005 in connection with PCT Intl. Appln. No. PCT/EP2005/052042.

Written Opinion issued on Nov. 4, 2007 in connection with PCT Intl. Appln. No. PCT/EP2005/052042.

International Preliminary Report on Patentability issued on Nov. 6, 2007 in connection with PCT Intl. Appln. No. PCT/EP2005/052042.

Search Report issued on Aug. 18, 2006 in connection with PCT Intl. Appln. No. PCT/EP2006/061972.

Written Opinion issued on Nov. 4, 2007 in connection with PCT Intl. Appln. No. PCT/EP2006/061972.

International Preliminary Report on Patentability issued on Nov. 6, 2007 in connection with PCT Intl. Appln. No. PCT/EP2006/061972.

Search Report issued on Jul. 5, 2006 in connection with PCT Intl. Appln. No. PCT/EP2006/061976.

Written Opinion issued on Nov. 4, 2007 in connection with PCT Intl. Appln. No. PCT/EP2006/061976.

International Preliminary Report on Patentability issued on Nov. 6, 2007 in connection with PCT Intl. Appln. No. PCT/EP2006/061976.

Search Report issued on Jul. 5, 2006 in connection with PCT Intl. Appln. No. PCT/EP2006/061978.

Written Opinion issued on Nov. 4, 2007 in connection with PCT Intl. Appln. No. PCT/EP2006/061978.

International Preliminary Report on Patentability issued on Nov. 6, 2007 in connection with PCT Intl. Appln. No. PCT/EP2006/061978.

Non-Final Rejection issued Jan. 8, 2010 in connection with US2009/0215773.

\* cited by examiner

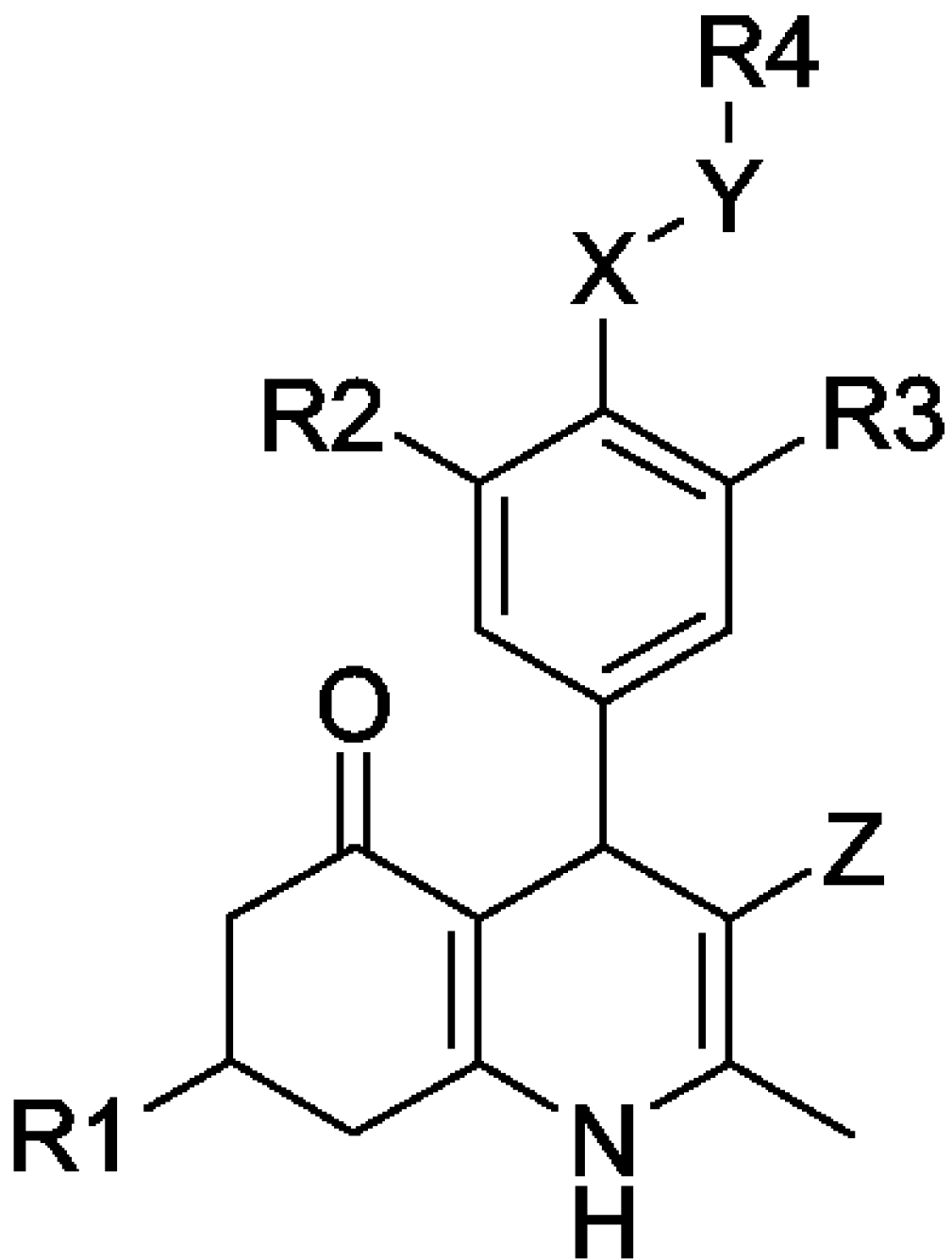

4-PHENYL-5-OXO-1,4,5,6,7,8-HEXAHYDROQUINOLINE DERIVATIVES FOR THE TREATMENT OF INFERTILITY

CROSS REFERENCE TO RELATED APPLICATION

This application claims priority based on International Patent Application No. PCT/EP2006/061972, filed on May 2, 2006.

FIELD OF THE INVENTION

The present invention relates to 4-phenyl-5-oxo-1,4,5,6,7,8-hexahydroquinoline derivatives, to pharmaceutical compositions comprising the same and to the use of said derivatives for the manufacture of medicaments for the treatment of infertility.

BACKGROUND OF THE INVENTION

Gonadotropins serve important functions in a variety of bodily functions including metabolism, temperature regulation and the reproductive process. Gonadotropins act on specific gonadal cell types to initiate ovarian and testicular differentiation and steroidogenesis. The pituitary gonadotropin FSH (follicle stimulating hormone) for example plays a pivotal role in the stimulation of follicle development and maturation whereas LH (luteinizing hormone) induces ovulation (Sharp, R. M. Clin Endocrinol. 33:787-807, 1990; Dorrington and Armstrong, Recent Prog. Horm. Res. 35:301-342, 1979). Currently, FSH is applied clinically for ovarian stimulation i.e. ovarian hyperstimulation for in vitro fertilisation (IVF) and induction of ovulation in infertile anovulatory women (Insler, V., Int. J. Fertility 33:85-97, 1988, Navot and Rosenwaks, J. Vitro Fert. Embryo Transfer 5:3-13, 1988), as well as for male hypogonadism and male infertility.

The gonadotropin FSH is released from the anterior pituitary under the influence of gonadotropin-releasing hormone and estrogens, and from the placenta during pregnancy. In the female, FSH acts on the ovaries promoting development of follicles and is the major hormone regulating secretion of estrogens. In the male, FSH is responsible for the integrity of the seminiferous tubules and acts on Sertoli cells to support gametogenesis. Purified FSH is used clinically to treat infertility in females and for some types of failure of spermatogenesis in males. Gonadotropins destined for therapeutic purposes can be isolated from human urine sources and are of low purity (Morse et al, Amer. J. Reproduct. Immunol. and Microbiology 17:143, 1988). Alternatively, they can be prepared as recombinant gonadotropins. Recombinant human FSH is available commercially and is being used in assisted reproduction (Olijve et al. Mol. Hum. Reprod. 2:371, 1996; Devroey et al. Lancet 339:1170, 1992).

The actions of the FSH hormone are mediated by a specific plasma membrane receptor that is a member of the large family of G-protein coupled receptors. These receptors consist of a single polypeptide with seven transmembrane domains and are able to interact with the Gs protein, leading to the activation of adenylate cyclase.

The FSH receptor is a highly specific target in the ovarian follicle growth process and is exclusively expressed in the ovary. Blocking of the receptor or inhibiting the signalling which is normally induced after FSH-mediated receptor activation will disturb follicle development and thus ovulation and fertility. Low molecular weight FSH antagonists could form the basis for new contraceptives, while low molecular weight FSH agonists can be used for the same clinical purposes as native FSH, i.e. for the treatment of infertility and for ovarian hyperstimulation on behalf of in vitro fertilisation.

Low molecular weight FSH mimetics with agonistic properties were disclosed in the International Application WO 2000/08015 (Applied Research Systems ARS Holding N.V.) and in WO 2002/09706 (Affymax Research Institute).

Certain tetrahydroquinoline derivatives have recently been disclosed in the International Application WO 2003/004028 (AKZO NOBEL N.V.) as FSH modulating substances, either having agonistic or antagonistic properties.

There remains a need for low molecular weight hormone mimetics that selectively activate the FSH receptor.

DETAILED DESCRIPTION OF THE INVENTION

To that aim the present invention provides 4-phenyl-5-oxo-1,4,5,6,7,8-hexahydroquinoline derivatives of general formula I

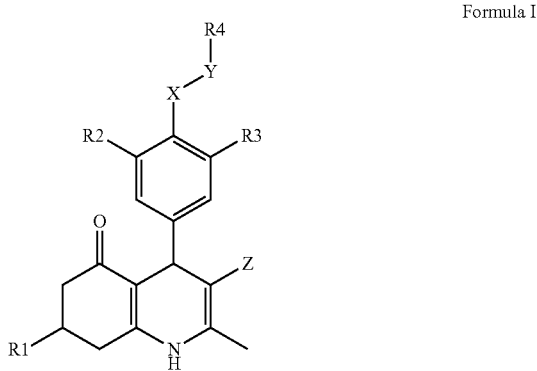

Formula I or a pharmaceutically acceptable salt thereof, wherein
$R^1$ is (1-6C)alkyl, (2-6C)alkenyl or (2-6C)alkynyl;
$R^2$, $R^3$ are independently halogen, (1-4C)alkyl, (2-4C)alkenyl, (2-4C)alkynyl, (1-4C)-alkoxy, (3-4C)alkenyloxy or (3-4C)alkynyloxy;
$R^4$ is phenyl or (2-5C)heteroaryl, both substituted with $R^7$ and optionally substituted on the (hetero)aromatic ring with one or more substituents selected from hydroxy, amino, halogen, nitro, trifluoromethyl, cyano, (1-4C)alkyl, (1-4C)alkoxy, (1-4C)alkylthio and (di)(1-4C)alkylamino;
$R^7$ is H, (1-4C)alkylthio, (1-4C)alkylsulfonyl, (di)(1-4C)alkylamino, $R^8R^9$-amino, $R^{10}R^{11}$-aminocarbonyl, $R^{12}R^{13}$-amino(1-4C)alkylcarbonylamino, $R^{14}R^{15}$-amino-(1-4C)-alkyl, $R^{16}$-oxy, $R^{17}R^{18}$-aminocarbonyl(1-4C)alkoxy, $R^{19}$-oxy(1-4C)alkyl, $R^{19}$-oxycarbonyl(1-4C)alkyl, $R^{20}R^{21}$-aminosulfonyl, $R^{20}$-oxysulfonyl, aminoiminomethyl, (di)(1-4C)alkylaminoiminomethyl or (2-6C)heterocycloalkyliminomethyl, trifluoromethylsulfonyl; $R^{23}$-oxycarbonyl, $R^{23}$-carbonyl or $R^{23}R^{24}$-aminocarbonyl;
$R^8$ is H or (1-4C)alkyl;
$R^9$ is (1-4C)alkylsulfonyl, (1-6C)alkylcarbonyl, (2-6C)alkenylcarbonyl, (2-6C)-alkynylcarbonyl, (3-6C)cycloalkylcarbonyl, (3-6C)cycloalkyl(1-4C)alkylcarbonyl, (1-4C)alkoxycarbonyl, (3-4C)alkenyloxycarbonyl, (3-4C)alkynyloxycarbonyl, (di)(1-4C)alkylaminocarbonyl, (2-6C)heterocycloalkylcarbonyl, (5-8C)alkyl, (3-6C)-cycloalkyl, (3-6C)cycloalkyl(1-4C)alkyl, (di)(1-4C)alkylamino(2-4C)alkyl, (2-6C)-heterocycloalkyl(2-4C)alkyl or phenylcarbonyl, phenylsulfonyl, phenyl(1-4C)alkoxy (1-4C)alkylcarbonyl, phenyl(1-4C)alkyl, (2-5C)heteroarylcarbonyl, (2-5C)heteroarylsulfonyl, (2-5C)heteroaryl(1-4C)alkyl, optionally substituted on the (hetero) aromatic ring with one or more substituents selected from hydroxy, amino, halogen, nitro, trifluoromethyl, cyano, (1-4C)alkyl, (1-4C)alkoxy or (di)(1-4C)alkylamino;

$R^{10}$ is H or (1-4C)alkyl;

$R^{11}$ is hydroxy(2-4C)alkyl, amino(2-4C)alkyl, (1-4C)alkoxy (2-4C)alkyl or (di)-(1-4C)alkylamino(2-4C)alkyl; or $R^{10}R^{11}$ in $R^{10}R^{11}$-aminocarbonyl may be joined in a (4-6C) heterocycloalkenyl ring or a (2-6C)heterocycloalkyl ring substituted with one or more substituents selected from (1-4C)alkyl, (1-4C)alkoxy(1-4C)alkyl and hydroxy(1-4C) alkyl;

$R^{12}$, $R^{13}$ are independently H, (1-6C)alkyl, (2-6C)alkenyl, (2-6C)alkynyl, (3-6C)-cycloalkyl, hydroxy(2-4C)alkyl, (1-4C)alkoxy(2-4C)alkyl, (3-6C)cycloalkyl-(1-4C)alkyl, (2-6C)heterocycloalkyl(1-4C)alkyl, amino(2-4C)alkyl, (di)(1-4C)alkylamino(2-4C)alkyl or phenyl(1-4C)alkyl, (2-5C)heteroaryl(1-4C)alkyl, optionally substituted on the (hetero)aromatic ring with one or more substituents selected from hydroxy, amino, halogen, nitro, trifluoromethyl, cyano, (1-4C)alkyl, (1-4C)alkoxy and (di)(1-4C) alkylamino; or $R^{12}R^{13}$ in $R^{12}R^{13}$-amino(1-4C)alkylcarbonylamino may be joined in a (4-6C)heterocycloalkenyl ring or a (2-6C)heterocycloalkyl ring, optionally substituted with one or more substituents selected from (1-4C)alkyl, (1-4C)alkoxy(1-4C)alkyl and hydroxy(1-4C)alkyl;

$R^{14}$, $R^{15}$ are independently H, (1-6C)alkyl, (2-6C)heterocycloalkyl(1-4C)alkyl, (3-6C)cycloalkyl(1-4C)alkyl, (1-4C)alkoxy(2-4C)alkyl, hydroxy(2-4C)alkyl, (di)(1-4C)alkylamino(2-4C)alkyl, amino(2-4C)alkyl, (1-4C)alkoxycarbonyl-(1-4C)alkyl, (1-6C)alkylcarbonyl, (3-6C)cycloalkylcarbonyl, (1-4C)alkoxycarbonyl, (3-4C)alkenyloxycarbonyl, (di)(1-4C)alkylaminocarbonyl, (2-6C)heterocycloalkylcarbonyl or (2-5C)heteroaryl(1-4C)alkyl, phenyl(1-4C)alkyl, (2-5C)heteroarylcarbonyl, phenylcarbonyl, optionally substituted on the (hetero)aromatic ring with one or more substituents selected from hydroxy, amino, halogen, nitro, trifluoromethyl, cyano, (1-4C)alkyl or (1-4C)alkoxy, (di)(1-4C)alkylamino; or $R^{14}R^{15}$ in $R^{14}R^{15}$-amino(1-4C)alkyl may be joined in a (4-6C)heterocycloalkenyl ring or a (2-6C)heterocycloalkyl ring, optionally substituted with one or more substituents selected from (1-4C)alkyl, (1-4C)alkoxy(1-4C) alkyl and hydroxy(1-4C)alkyl;

$R^{16}$ is (2-6C)heterocycloalkyl(1-4C)alkyl, (di)(1-4C)alkylamino(2-4C)alkyl, (2-4C)alkoxy(1-4C)alkyl, hydroxy(2-4C)alkyl, amino(2-4C)alkyl, hydroxycarbonyl(1-4C) alkyl, (1-4C)alkoxycarbonyl(1-4C)alkyl, (1-4C)alkoxycarbonyl, (3-4C)alkenyloxycarbonyl, (3-4C)alkynyloxycarbonyl, (di)(1-4C)alkylaminocarbonyl, (2-6C)heterocycloalkylcarbonyl, or phenyl(1-4C)alkyl, (2-5C)heteroaryl(1-4C)alkyl, optionally substituted on the (hetero)aromatic ring with one or more substituents selected from hydroxy, amino, halogen, nitro, trifluoromethyl, cyano, (1-4C)alkyl, (1-4C)alkoxy and (di)(1-4C) alkylamino;

$R^{17}$, $R^{18}$ are independently H, (1-6C)alkyl, (3-6C)cycloalkyl (1-4C)alkyl, (1-4C)-alkoxy (2-4C)alkyl, hydroxy(2-4C) alkyl, amino(2-4C)alkyl, (di)(1-4C)alkylamino(2-4C) alkyl, (2-6C)heterocycloalkyl(2-4C)alkyl, or phenyl(1-4C)alkyl, (2-5C)heteroaryl(1-4C)alkyl, optionally substituted on the (hetero)aromatic ring with one or more substituents selected from hydroxy, amino, halogen, nitro, trifluoromethyl, cyano, (1-4C)alkyl, (1-4C)alkoxy and (di) (1-4C)alkylamino; or $R^{17}R^{18}$ in $R^{17}R^{18}$-aminocarbonyl(1-4C)alkoxy may be joined in a (4-6C)heterocycloalkenyl ring or a (2-6C)heterocycloalkyl ring, optionally substituted with one or more substituents selected from (1-4C)alkyl, (1-4C)alkoxy(1-4C)alkyl and hydroxy(1-4C)alkyl;

$R^{19}$ is H or (1-6C)alkyl;

$R^{20}$, $R^{21}$ are independently H, (1-6C)alkyl, (1-6C)alkenyl, (1-6C)alkynyl or (1-4C)alkoxy(1-4C)alkyl; or $R^{20}R^{21}$ in $R^{20}R^{21}$-aminosulfonyl may be joined in a (4-6C) heterocycloalkenyl ring or a (2-6C)heterocycloalkyl ring, optionally substituted with one or more substituents selected from (1-4C)alkyl, (1-4C)alkoxy(1-4C)alkyl and hydroxy-(1-4C)alkyl;

X is O or N—$R^{22}$;

Y is $CH_2$, C(O) or $SO_2$;

Z is CN or NO2;

$R^{22}$ is H, (1-4C)alkyl;

$R^{23}$, $R^{24}$ are independently H, (1-4C)alkyl, (2-4C)alkenyl, (2-4C)alkynyl, (3-6C)cycloalkyl, (3-6C)cycloalkyl(1-4C) alkyl, (2-6C)heterocycloalkyl, (2-6C)heterocycloalkyl(1-4C)alkyl, (1-4C)alkoxycarbonyl(1-4C)alkyl, (di)(1-4C) alkylaminocarbonyl(1-4C)alkyl or phenylaminocarbonyl (1-4C)alkyl, (2-5C)heteroarylaminocarbonyl(1-4C)alkyl, phenyl, (2-5C)heteroaryl, phenyl(1-4C)alkyl, (2-5C)heteroaryl(1-4C)alkyl, optionally substituted at the (hetero) atom with one or more substituents selected from hydroxy, amino, halogen, nitro, trifluoromethyl, cyano, (1-4C)alkyl, (2-4C)alkenyl, (2-4C)alkynyl, (1-4C)alkoxy and (di)(1-4C)alkylamino; or $R^{23}R^{24}$ in $R^{23}R^{24}$-aminocarbonyl may be joined in a (4-6C) heterocycloalkenyl ring or a (2-6C)heterocycloalkyl ring, optionally substituted with one or more substituents selected from (1-4C)alkyl, (1-4C)alkoxy(1-4C)alkyl and hydroxy-(1-4C)alkyl; with the proviso that the compounds of formula I wherein X is O, $R^4$ is phenyl and $R^7$ is selected from H, (1-4C)alkylthio, (1-4C)alkylsulfonyl, di(1-4C) alkylamino, $R^{23}$-oxycarbonyl, $R^{23}$-carbonyl and $R^{23}R^{24}$-aminocarbonyl, and the compounds of formula I wherein X is O, $R^4$ is (2-5C)heteroaryl and $R^7$ is H or (di)(1-4C) alkylamino, are excluded.

The 4-phenyl-5-oxo-1,4,5,6,7,8-hexahydroquinoline derivatives according to the present invention are potent FSH receptor activators and can be used for the same clinical purposes as native FSH since they behave like agonists, with the advantage that they may be prepared synthetically, may display altered stability properties and may be administered differently.

Thus, the FSH-receptor agonists of the present invention may be used for the treatment of fertility disorders e.g. controlled ovarian hyperstimulation and IVF procedures.

The term (1-4C)alkyl as used in the definition means a branched or unbranched alkyl group having 1-4 carbon atoms, being methyl, ethyl, propyl, isopropyl, butyl, isobutyl, sec-butyl and tert-butyl.

The term (1-6C)alkyl means a branched or unbranched alkyl group having 1-6 carbon atoms, for example methyl, ethyl, propyl, isopropyl, butyl, tert-butyl, n-pentyl and n-hexyl. (1-5C)Alkyl groups are preferred, (1-4C)alkyl being the most preferred.

The term (5-8C)alkyl as used in the definition means a branched or unbranched alkyl group having 5-8 carbon atoms.

The term (2-6C)alkenyl means a branched or unbranched alkenyl group having 2-6 carbon atoms, such as ethenyl, 2-butenyl, and n-pentenyl.

The term (2-4C)alkenyl means a branched or unbranched alkenyl group having 2-4 carbon atoms, such as ethenyl, n-propenyl and 2-butenyl.

The term (2-6C)alkynyl means a branched or unbranched alkynyl group having 2-6 carbon atoms, such as ethynyl, propynyl and n-pentynyl.

The term (2-4C)alkynyl means an alkynyl group having 2-4 carbon atoms, such as ethynyl and propynyl.

The term (3-6C)cycloalkyl means a cycloalkyl group having 3-6 carbon atoms, being cyclopropyl, cyclobutyl, cyclopentyl and cyclohexyl.

The term (3-6C)cycloalkyl(1-4C)alkyl means a cycloalkylalkyl group, the cycloalkyl group of which has 3-6 carbon atoms with the same meaning as previously defined and the alkyl group having 1-4 carbon atoms with the same meaning as previously defined.

The term (3-6C)cycloalkyl(1-4C)alkylcarbonyl means a cycloalkyl moiety having 3-6 carbon atoms as previously defined, attached to the alkyl moiety, having 1-4 carbon atoms, of an alkylcarbonyl group.

The term (3-6C)cycloalkylcarbonyl means a cycloalkyl group having 3-6 carbon atoms as previously defined, attached to a carbonyl group.

The term (2-6C)heterocycloalkyl means a heterocycloalkyl group having 2-6 carbon atoms, preferably 3-5 carbon atoms, and at least including one heteroatom selected from N, O and/or S, which may be attached via a heteroatom if feasible, or a carbon atom. Preferred heteroatoms are N or O. Most preferred are piperidin-1-yl, morpholin-4-yl, pyrrolidin-1-yl and piperazin-1-yl.

The term (4-6C)heterocycloalkenyl means a heterocycloalkenyl group having 4-6 carbon atoms, preferably 3-5 carbon atoms, and at least including one heteroatom selected from N, O and/or S, which may be attached via a heteroatom if feasible, or a carbon atom. Preferred heteroatoms are N or O.

The term (2-6C)heterocycloalkyl(1-4C)alkyl means a heterocycloalkylalkyl group, the heterocycloalkyl group of which has 2-6 carbon atoms, preferably 3-5 carbon atoms, with the same meaning as previously defined and the alkyl group having 1-4 carbon atoms with the same meaning as previously defined.

The term (2-6C)heterocycloalkyl(2-4C)alkyl means a heterocycloalkylalkyl group, the heterocycloalkyl group of which has 2-6 carbon atoms, preferably 3-5 carbon atoms, with the same meaning as previously defined and the alkyl group having 2-4 carbon atoms.

The term (2-6C)heterocycloalkylcarbonyl means a heterocycloalkylcarbonyl group, the heterocycloalkyl group of which has 2-6 carbon atoms, preferably 3-5 carbon atoms, with the same meaning as defined previously.

The term (2-5C)heteroaryl means a substituted or unsubstituted aromatic group having 2-5 carbon atoms and at least including one heteroatom selected from N, O and S, like imidazolyl, thiadiazolyl, pyridinyl, thienyl or furyl. Preferred heteroaryl groups are thienyl, furyl and pyridinyl. The (2-5C) heteroaryl group may be attached via a carbon atom or a heteroatom, if feasible.

The term (2-5C)heteroaryl(1-4C)alkyl means a heteroarylalkyl group, the heteroaryl group of which contains 2-5 carbon atoms with the same meaning and preferences as previously defined and the alkyl group contains 1-4 carbon atoms with the same meaning as previously defined.

The term (2-5C)heteroarylaminocarbonyl(1-4C)alkyl means a heteroarylaminocarbonyl group, the heteroaryl group of which contains 2-5 carbon atoms with the same meaning and preferences as previously defined attached to an alkyl group containing 1-4 carbon atoms with the same meaning as previously defined.

The term (2-5C)heteroarylcarbonyl means a heteroarylcarbonyl group, the heteroaryl group of which contains 2-5 carbon atoms with the same meaning and preferences as previously defined.

The term (2-5C)heteroarylsulfonyl means a heteroarylsulfonyl group, the heteroaryl group of which contains 2-5 carbon atoms with the same meaning and preferences as previously defined.

The term (1-6C)alkylcarbonyl means an alkylcarbonyl group, the alkyl group of which contains 1-6 carbon atoms with the same meaning as previously defined.

The term (2-6C)alkenylcarbonyl means an alkenylcarbonyl group, the alkenyl group of which contains 2-6 carbon atoms with the same meaning as previously defined.

The term (2-6C)alkynylcarbonyl means an alkynylcarbonyl group, the alkyl group of which contains 2-6 carbon atoms with the same meaning as previously defined The term (1-4C)alkylsulfonyl means an alkylsulfonyl group, the alkyl group of which contains 1-4 carbon atoms with the same meaning as previously defined.

The term (1-4C)alkylthio means an alkylthio group having 1-4 carbon atoms, the alkyl moiety having the same meaning as previously defined.

The term (1-4C)alkoxy means an alkoxy group having 1-4 carbon atoms, the alkyl moiety having the same meaning as previously defined. (1-2C)Alkoxy groups are preferred.

The term (3-4C)alkenyloxy means an alkenyloxy group having 3-4 carbon atoms, the alkenyl moiety having the same meaning as previously defined.

The term (3-4C)alkynyloxy means an alkynyloxy group having 3-4 carbon atoms, the alkynyl moiety having the same meaning as previously defined.

The term (1-4C)alkoxycarbonyl means an alkoxycarbonyl group, the alkoxy group of which contains 1-4 carbon atoms with the same meaning as previously defined. (1-2C)Alkoxycarbonyl groups are preferred.

The term (3-4C)alkenyloxycarbonyl means an alkenyloxycarbonyl group, the alkenyl group of which contains 3-4 carbon atoms.

The term (3-4C)alkynyloxycarbonyl means an alkynyloxycarbonyl group, the alkynyl group of which contains 3-4 carbon atoms.

The term (1-4C)alkoxy(1-4C)alkyl means an alkoxy group, the alkyl group of which contains 1-4 carbon atoms which is attached to an alkyl group having 1-4 carbon atoms.

The term (1-4C)alkoxy(2-4C)alkyl means an alkoxy group, the alkyl group of which contains 1-4 carbon atoms which is attached to an alkyl group having 2-4 carbon atoms.

The term (1-4C)alkoxycarbonyl(1-4C)alkyl means an alkoxycarbonylalkyl group, the alkyl groups of which contain 1-4 carbon atoms with the same meaning as previously defined.

The term phenyl(1-4C)alkyl means a phenyl group attached to an alkyl group having 1-4 carbon atoms as defined previously.

The term phenyl(1-4C)alkoxy(1-4C)alkylcarbonyl means a phenylalkoxy moiety, the alkyl group of which contains 1-4 carbon atoms attached to the alkyl group of a alkylcarbonyl moiety, the alkyl group also containing 1-4 carbon atoms.

The term phenylaminocarbonyl(1-4C)alkyl means a phenylaminocarbonyl group attached to an alkyl group having 1-4 carbon atoms as defined previously.

The term hydroxy(2-4C)alkyl as used herein means an hydroxyalkyl group having 2-4 carbon atoms, the alkyl moiety having the same meaning as previously defined.

The term hydroxycarbonyl(1-4C)alkyl means a hydroxycarbonylalkyl group, the alkyl group of which contains 1-4 carbon atoms with the same meaning as previously defined.

The term (di)(1-4C)alkylamino as used herein means an amino group, monosubstituted or disubstituted with alkyl groups, each of which contains 1-4 carbon atoms and has the same meaning as previously defined.

The term (di)(1-4C)alkylaminocarbonyl means a (di)alkylaminocarbonyl group, the (di)alkylamino group of which is as defined previously.

The term (di)(1-4C)alkylaminocarbonyl(1-4C)alkyl means a (di)alkylaminocarbonylalkyl group, the alkyl groups of which contain 1-4 carbon atoms with the same meaning as previously defined.

The term aminocarbonyl(1-4C)alkoxy means an aminocarbonylalkoxy group, the alkyl group of which contains 1-4 carbon atoms with the same meaning as previously defined.

The term (di)(1-4C)alkylamino(2-4C)alkyl as used herein means an (di)alkylamino group having 1-4 carbon atoms, connected via the amino group to an alkyl group having 2-4 carbon atoms, the alkyl moieties having the same meaning as previously defined.

The term amino(1-4C)alkylcarbonylamino means an aminoalkylcarbonylamino group, the alkyl group of which contains 1-4 carbon atoms with the same meaning as previously defined.

The term amino(2-4C)alkyl as used herein means an aminoalkyl group having 2-4 carbon atoms, the alkyl moiety having the same meaning as previously defined.

The term (di)(1-4C)alkylaminoiminomethyl as used herein means an alkylaminoiminomethyl group, the amino group of which is monosubstituted or disubstituted with alkyl groups having 1-4 carbon atoms and having the same meaning as previously defined.

The term (2-6C)heterocycloalkyliminomethyl as used herein means a heterocycloalkyliminomethyl group, the heterocycloalkyl moiety of which is as previously defined.

The term halogen means fluorine, chlorine, bromine or iodine; chlorine, bromine or iodine being preferred.

The term pharmaceutically acceptable salt represents those salts which are, within the scope of medical judgement, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

The invention also relates to compounds of formula I, wherein $R^1$ is (1-6C)alkyl. More in particular, the invention relates to compounds wherein $R^1$ is (1-4C)alkyl.

Another aspect of the invention are compounds according to formula I wherein $R^2$, $R^3$ is halogen and/or (1-4C)alkoxy.

In yet another aspect, the invention concerns compounds of formula I, wherein Y is $CH_2$.

Another aspect of the invention is a compound wherein Z is CN.

In another aspect the invention concerns compounds wherein X=O.

The invention also relates to compounds according to general Formula I wherein $R^7$ is $R^8R^9$-amino, $R^{10}R^{11}$-aminocarbonyl, $R^{12}R^{13}$-amino(1-4C)alkylcarbonylamino, $R^{14}R^{15}$-amino(1-4C)alkyl or $R^{17}R^{18}$-aminocarbonyl(1-4C)alkoxy.

In another aspect the invention concerns compounds wherein $R^8$ is H, $R^9$ is (1-4C)alkylsulfonyl, (1-6C)alkylcarbonyl, (3-6C)cycloalkylcarbonyl, (1-4C)alkoxycarbonyl, (3-4C)alkenyloxycarbonyl, (di)(1-4C)alkylaminocarbonyl, (2-6C)heterocycloalkylcarbonyl, or phenylcarbonyl, phenyl(1-4C)alkoxy(1-4C)alkylcarbonyl, (2-5C)heteroarylcarbonyl, (2-5C)heteroarylsulfonyl or (2-5C)heteroaryl(1-4C)alkyl, optionally substituted on the (hetero)aromatic ring with one or more substituents selected from, halogen or (1-4C)alkoxy;

$R^{10}$ is H or (1-4C)alkyl;

$R^{11}$ is hydroxy(2-4C)alkyl, amino(2-4C)alkyl, (1-4C)alkoxy(2-4C)alkyl or (di)(1-4C)alkylamino(2-4C)alkyl; or $R^{10}$ and $R^{11}$ form together with the N to which they are bonded a (4-6C)heterocycloalkenyl ring or a (2-6C)heterocycloalkyl ring, optionally substituted with one or more substituents selected from (1-4C)alkyl;

$R^{12}$, $R^{13}$ are independently H, (1-6C)alkyl, (3-6C)cycloalkyl, hydroxy(2-4C)alkyl, (1-4C)alkoxy(2-4C)alkyl, (2-6C)heterocycloalkyl(1-4C)alkyl or (di)(1-4C)alkylamino(2-4C)alkyl or phenyl(1-4C)alkyl, (2-5C)heteroaryl(1-4C)alkyl, optionally substituted on the (hetero)aromatic ring with one or more substituents selected from halogen; or $R^{12}$ and $R^{13}$ form together with the N to which they are bonded a (4-6C)heterocycloalkenyl ring or a (2-6C)heterocycloalkyl ring, both optionally substituted with one or more substituents selected from (1-4C)alkyl or hydroxy(1-4C)alkyl;

$R^{14}$, $R^{15}$ are independently H, (1-6C)alkyl, hydroxy(2-4C)alkyl, (1-4C)alkoxycarbonyl(1-4C)alkyl, (1-6C)alkylcarbonyl, (3-6C)cycloalkylcarbonyl, (1-4C)alkoxycarbonyl or (2-5C)heteroaryl(1-4C)alkyl or (2-5C)heteroarylcarbonyl, phenylcarbonyl;

$R^{16}$ is (2-6C)heterocycloalkyl(1-4C)alkyl, (di)(1-4C)alkylamino(2-4C)alkyl, (2-4C)alkoxy(1-4C)alkyl, hydroxycarbonyl(1-4C)alkyl, (1-4C)alkoxycarbonyl(1-4C)alkyl; or phenyl(1-4C)alkyl or (2-5C)heteroaryl(1-4C)alkyl, optionally substituted on the (hetero)aromatic ring with one or more substituents selected from halogen or (1-4C)alkoxy;

$R^{17}$, $R^{18}$ are independently H, (1-6C)alkyl, (3-6C)cycloalkyl(1-4C)alkyl, (1-4C)alkoxy(2-4C)alkyl, (2-6C)heterocycloalkyl(2-4C)alkyl; or phenyl(1-4C)alkyl or (2-5C)heteroaryl(1-4C)alkyl, optionally substituted on the (hetero)aromatic ring with one or more substituents selected from halogen; or $R^{17}$ and $R^{18}$ form together with the N to which they are bonded a (4-6C)heterocycloalkenyl ring or a (2-6C)heterocycloalkyl ring, optionally substituted with one or more substituents selected from (1-4C)alkyl or hydroxy(1-4C)alkyl.

The invention also relates to compounds according to Formula I wherein $R^7$ is $R^8R^9$-amino.

Another aspect of the invention concerns compounds wherein $R^8$ is H and $R^9$ is (1-4C)alkylsulfonyl.

Still another aspect of the invention concerns compounds wherein one or more of the specific definitions of the groups $R^1$ through $R^{24}$ and X, Y and Z as defined here above are combined in the definition of the 4-phenyl-5-oxo-1,4,5,6,7,8-hexahydroquinoline derivatives of formula I.

The invention also concerns compounds selected from the group of N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-3,4,5-trimethoxy-benzamide;

N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-2-[(pyridin-4-ylmethyl)-amino]-acetamide;
N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-2-[4-(2-hydroxy-ethyl)-piperazin-1-yl]-acetamide;
4-{3-Bromo-4-[3-(3,6-dihydro-2H-pyridine-1-carbonyl)-benzyloxy]-5-ethoxy-phenyl}-2-methyl-5-oxo-7-propyl-1,4,5,6,7,8-hexahydro-quinoline-3-carbonitrile;
3-[Bis-(2-methoxy-ethyl)-amino]-N-{3-[2-bromo-4-(3-cyano-2-methyl-5-oxo-7-propyl-1,4,5,6,7,8-hexahydro-quinolin-4-yl)-6-ethoxy-phenoxymethyl]-phenyl}-propionamide;
2-{3-[2-Bromo-4-(3-cyano-2-methyl-5-oxo-7-propyl-1,4,5,6,7,8-hexahydro-quinolin-4-yl)-6-ethoxy-phenoxymethyl]-phenoxy}-N,N-dimethyl-acetamide;
4-{3-Bromo-5-ethoxy-4-[3-(2-morpholin-4-yl-2-oxoethoxy)-benzyloxy]-phenyl}-2-methyl-5-oxo-7-propyl-1,4,5,6,7,8-hexahydro-quinoline-3-carbonitrile;
Furan-2-carboxylic acid {2-[2-bromo-4-(3-cyano-2-methyl-5-oxo-7-propyl-1,4,5,6,7,8-hexahydro-quinolin-4-yl)-6-ethoxy-phenoxymethyl]-phenyl}-amide;
N-{2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-acrylamide;
Cyclopropanecarboxylic acid {2-[2-bromo-4-(3-cyano-2-methyl-5-oxo-7-propyl-1,4,5,6,7,8-hexahydro-quinolin-4-yl)-6-ethoxy-phenoxymethyl]-phenyl}-amide;
2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-carbamic acid methyl ester;
1-{2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-3-methyl-urea
{3-[2-Bromo-4-(3-cyano-2-methyl-5-oxo-7-propyl-1,4,5,6,7,8-hexahydro-quinolin-4-yl)-6-ethoxy-phenoxymethyl]-pyridin-2-yl}-carbamic acid methyl ester
4-(3-Bromo-5-ethoxy-4-{3-[(1H-imidazol-4-ylmethyl)-amino]-benzyloxy}-phenyl)-2-methyl-5-oxo-7-propyl-1,4,5,6,7,8-hexahydro-quinoline-3-carbonitrile;
N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-methanesulfonamide;
{4-[2-Bromo-4-(3-cyano-2-methyl-5-oxo-7-propyl-1,4,5,6,7,8-hexahydro-quinolin-4-yl)-6-ethoxy-phenoxymethyl]-phenyl}-carbamic acid allyl ester;
4-[3-Bromo-5-ethoxy-4-(1-methanesulfonyl-1H-pyrrol-2-ylmethoxy)-phenyl]-2-methyl-5-oxo-7-propyl-1,4,5,6,7,8-hexahydro-quinoline-3-carbonitrile;
4-[2-Bromo-4-(3-cyano-2-methyl-5-oxo-7-propyl-1,4,5,6,7,8-hexahydro-quinolin-4-yl)-6-ethoxy-phenoxymethyl]-N-methyl-benzamidine;
4-{3-Bromo-5-ethoxy-4-[(pyridin-3-ylmethyl)-amino]-phenyl}-2-methyl-5-oxo-7-propyl-1,4,5,6,7,8-hexahydro-quinoline-3-carbonitrile;
N-(2-{[2-Bromo-4-(3-cyano-2-methyl-5-oxo-7-propyl-1,4,5,6,7,8-hexahydro-quinolin-4-yl)-6-ethoxy-phenylamino]-methyl}-phenyl)-methanesulfonamide;
4-{3-Bromo-4-[2-(cyclopropylmethyl-amino)-benzyloxy]-5-ethoxy-phenyl}-2-methyl-5-oxo-7-propyl-1,4,5,6,7,8-hexahydro-quinoline-3-carbonitrile; or
N-{2-[2-Bromo-4-((4R,7S)-3-cyano-2-methyl-5-oxo-7-propyl-1,4,5,6,7,8-hexahydro-quinolin-4-yl)-6-ethoxy-phenoxymethyl]-4,5-difluoro-phenyl}-methanesulfonamide Suitable methods for the preparation of the 4-phenyl-5-oxo-1,4,5,6,7,8-hexahydroquinoline derivatives of the invention are outlined below.

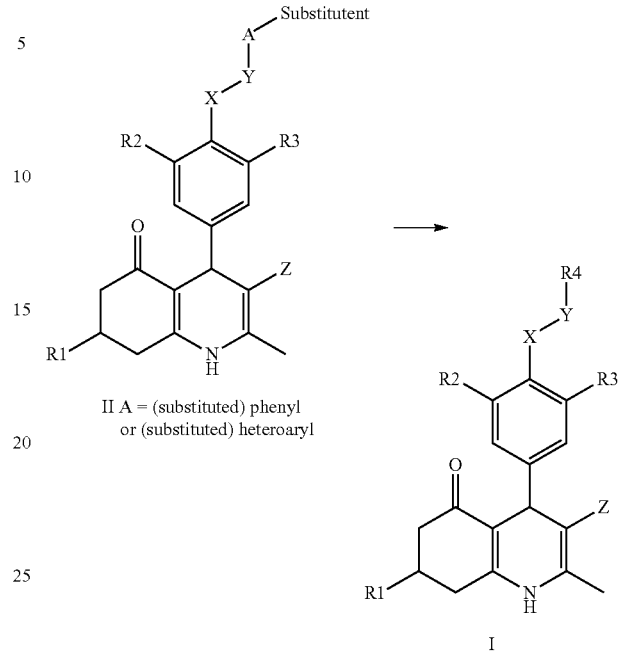

II A = (substituted) phenyl
or (substituted) heteroaryl

I

The 4-phenyl-5-oxo-1,4,5,6,7,8-hexahydroquinoline derivatives I of the present

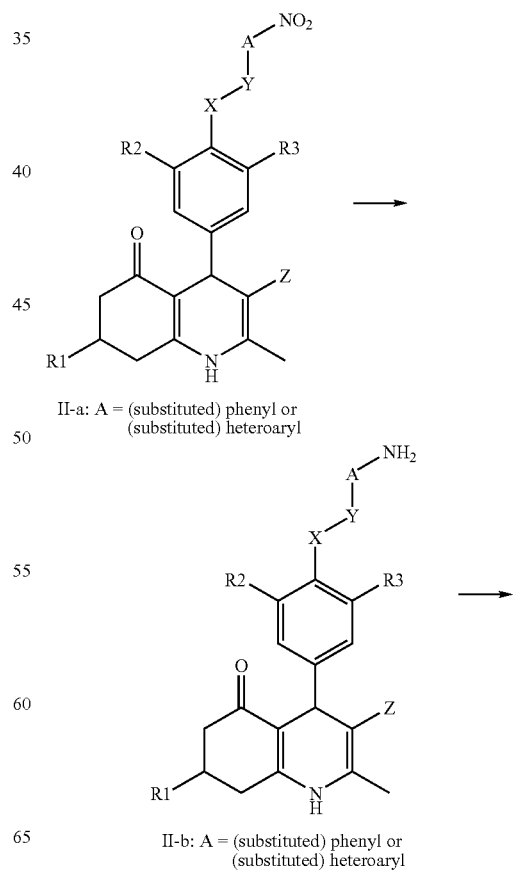

II-a: A = (substituted) phenyl or
(substituted) heteroaryl

II-b: A = (substituted) phenyl or
(substituted) heteroaryl

-continued

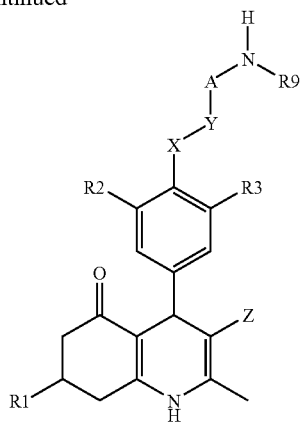

I-a: A = (substituted) phenyl or (substituted) heteroaryl
R⁹ = acyl or sulfonyl group invention can be prepared starting from appropriately functionalised 1,4-dihydropyridine derivatives of general structure II, wherein $R^1$, $R^2$, $R^3$, X, Y and Z are as previously defined and A is a phenyl or a heteroaryl ring.

For example, acylation or sulfonylation of compounds of general formula I-b yields compounds of general formula I-a, wherein $R^1$, $R^2$, $R^3$, X, Y and Z are as previously defined, $R^8$ is H, $R^9$ is an acyl or sulfonyl group and A is a (substituted) phenyl or a (substituted) heteroaryl ring.

In a typical experiment, compounds II-b are reacted in a solvent, such as dichloromethane, N,N-dimethylformamide, dimethyl sulfoxide, ethanol, tetrahydrofuran, 1,4-dioxane, toluene, 1-methyl-pyrrolidin-2-one or pyridine with an appropriately substituted acyl halide, acid anhydride or sulfonyl halide in the presence of a base such as triethylamine, N,N-diisopropylethylamine (DiPEA) or pyridine, to

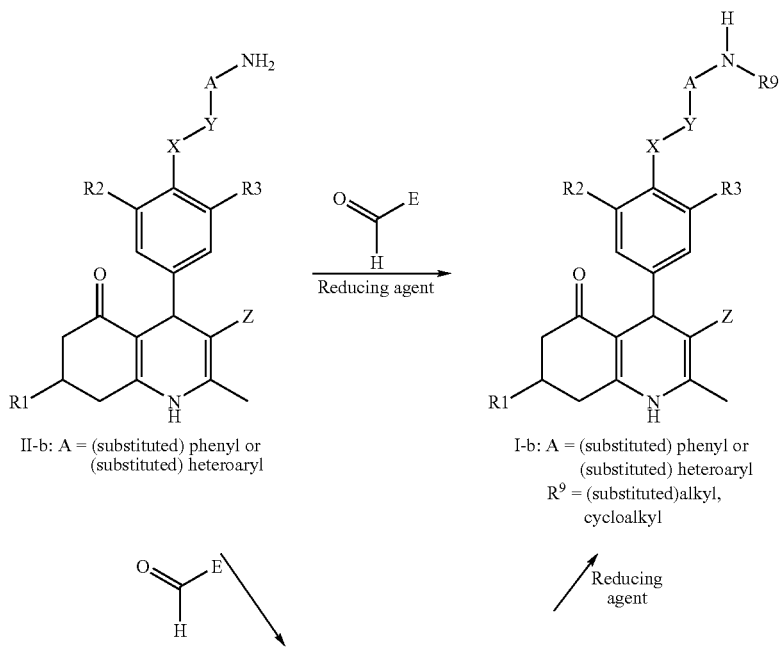

II-b: A = (substituted) phenyl or (substituted) heteroaryl

I-b: A = (substituted) phenyl or (substituted) heteroaryl
R⁹ = (substituted)alkyl, cycloalkyl

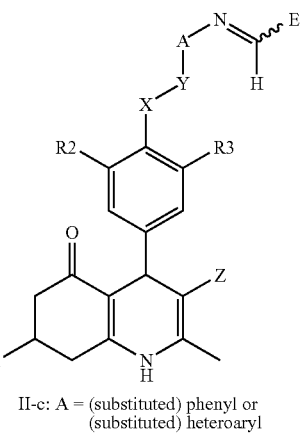

II-c: A = (substituted) phenyl or (substituted) heteroaryl give N-acylated or N-sulfonylated derivatives of formula I-a, respectively. Alternatively, N-acylated compounds of general formula I-a can be obtained by reaction of a (hetero)aromatic carboxylic acid in the presence of a coupling reagent such as diisopropyl carbodiimide (DIC), (3-dimethylaminopropyl)-ethyl-carbodiimide (EDCI), O-(benzotriazol-1-yl)-N,N,N',N'-tetramethyluronium tetrafluoroborate (TBTU) or O-(7-azabenzotriazol-1-yl)-N,N,N',N'-tetramethyluronium hexafluorophosphate (HATU) and a tertiary amine base (e.g. DiPEA) in a solvent such as N,N-dimethylformamide or dichloromethane at ambient or elevated temperature.

Compounds of general formula I-b, wherein $R^1$, $R^2$, $R^3$, X, Y and Z are as previously defined, $R^9$ is a (substituted) alkyl group and A is a (substituted) phenyl or a (substituted) heteroaryl ring, can be prepared by reductive alkylation of the amino group with appropriately substituted aldehydes of general formula E-C(O)H (E=alkyl, cycloalkyl, cycloalkylalkyl, (di)alkylaminoalkyl, heterocycloalkylalkyl, (hetero)aryl, (hetero)arylalkyl) and a suitable reducing agent such as sodium cyanoborohydride or sodium triacetoxyborohydride. Likewise, appropriately substituted ketones can be used in this procedure. Alternatively, compounds of general formula I-b can be converted to the corresponding (hetero)arylimine II-c upon reaction with appropriately substituted aldehydes of general formula E-C(O)H (see above) by methods known to those skilled in the art, followed by reduction with a reducing agent such as sodium borohydride to give compounds of general formula I-b. In this case, appropriately substituted ketones can be used as well.

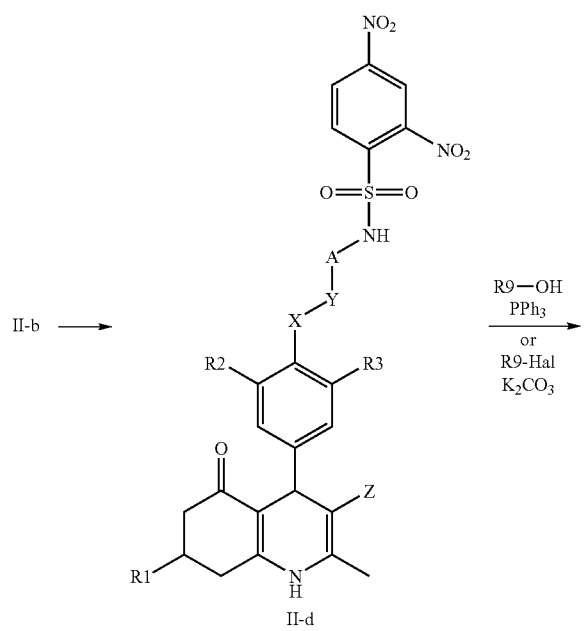

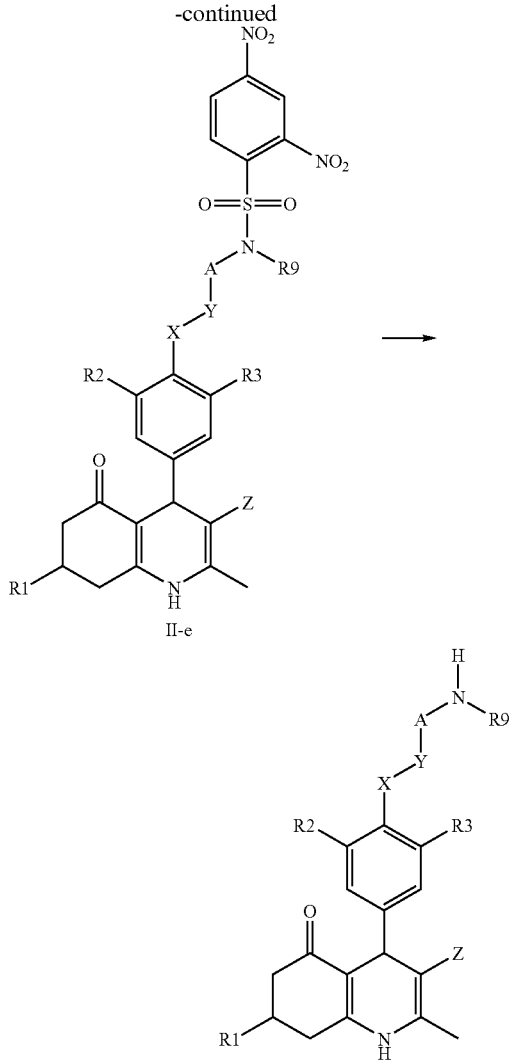

Alternatively, compounds of general formula II-b can be converted to 2,4-dinitrobenzenesulfonamide derivatives II-d by sulfonylation with 2,4-dinitrobenzenesulfonyl chloride. The sulfonamide can be alkylated to give compounds of general formula II-e by using art known Mitsunobu reactions with appropriately substituted primary or secondary alcohols of formula $R^9$—OH ($R^9$=alkyl, cycloalkyl, cycloalkylalkyl, (di)alkylaminoalkyl, heterocycloalkylalkyl or (hetero)arylalkyl), triphenylphosphine (optionally resin bound) and a dialkyl azodicarboxylate in appropriate solvents such as 1,4-dioxane, tetrahydrofuran or dichloromethane at elevated or ambient temperature. Alternatively, the sulfonamide can be alkylated using alkyl halides of formula $R^9$-Hal (Hal=Cl, Br, I) and a suitable base such as $K_2CO_3$ in a solvent such as N,N-dimethylformamide, tetrahydrofuran or 1,4-dioxane. Cleavage of the N—S sulfonamide bond with a primary amine such as propylamine in a suitable solvent such as dichloromethane then gives compounds of formula I-b. Alternatively, the N—S sulfonamide bond can be cleaved using mercaptoacetic acid and a tertiary amine base in a solvent such as dichloromethane. Precedence for these types of reactions can be found in literature. For example, see: Tetrahedron Lett. 38 (1997) 5831-5834, Bioorg. Med. Chem. Lett. 10 (2000) 835-838.

Compounds of general formula I-c, wherein $R^1$, $R^2$, $R^3$, $R^9$, X, Y and Z are as previously defined, $R^8$ is (1-4C)alkyl and A is a (substituted) (hetero)aryl group, can be prepared from compounds I-a, I-b or II-f Alkylation of compounds I-a with $R^8$-Hal (Hal=Cl, Br, I) or $R^8$—OH by the same methods described for the alkylations of compounds II-d yields the desired N,N-disubstituted aniline derivatives I-c. Additionally, alkylation of compounds of formula I-b by the same methods described for the reductive alkylation of compounds of formula II-b also yields N,N-disubstituted aniline derivatives of formula I-c.

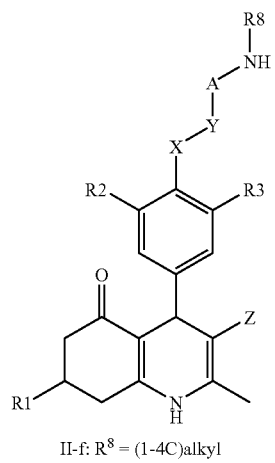

II-f: $R^8$ = (1-4C)alkyl

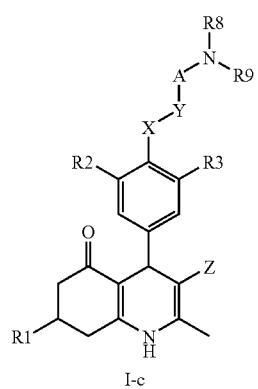

I-c ← I-a or I-b

Compounds of general formula II-f, prepared by the same methods described for the synthesis of compounds of formula I-b, can be acylated, sulfonylated or reductively alkylated as described for the preparation of I-a and I-b, respectively, to give compounds of general formula I-c.

The nitro group in compounds of general formula II-a can be reduced to the corresponding amino group to give compounds of general formula I-b. Typically, compounds II-a are treated with zinc and acetic acid in a suitable solvent such as THF or dioxane at temperatures between 0° C. and reflux temperature. Alternative methods include treatment with iron, $SnCl_2$ or hydrogen in the presence of a transition metal catalyst such palladium or platinum on charcoal, using methods and reagents well known to those skilled in the art. Alternatively, compounds of general formula II-b can be obtained by cleavage of known N-protecting groups such as an Allyloxycarbonyl (Alloc), Fluoren-9-yl-methoxycarbonyl (Fmoc) or tert-butoxycarbonyl (Boc) group in compounds of general formula II-g to give the corresponding derivatives II-b. Related protective group manipulations can be found in *Protective groups in Organic Synthesis*, T. W. Greene and P. G. M. Wuts, John Wiley & sons, Inc., New York, 1999.

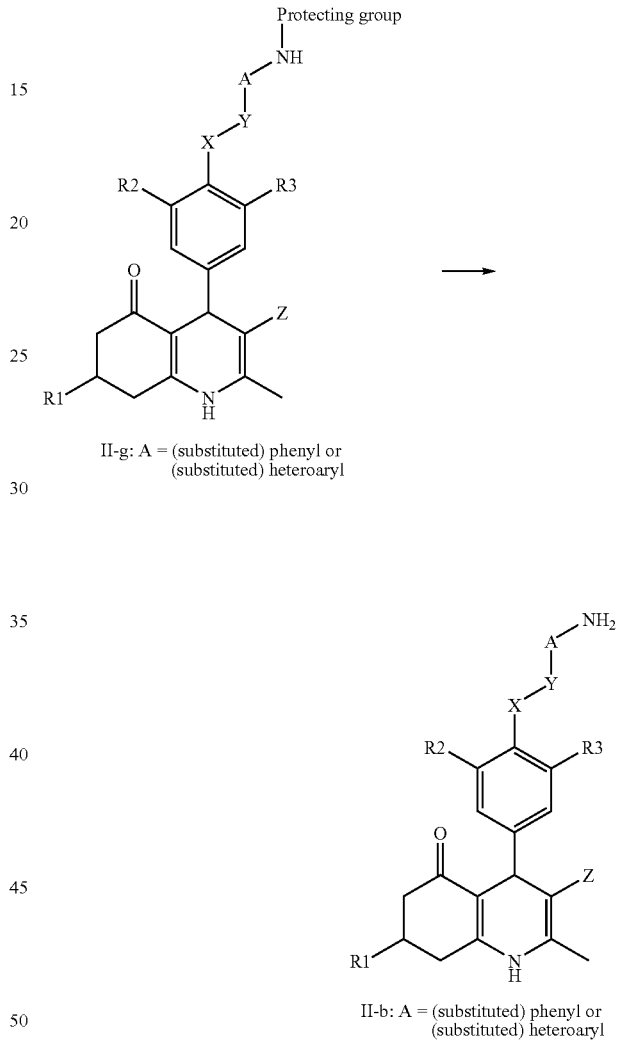

II-g: A = (substituted) phenyl or (substituted) heteroaryl

II-b: A = (substituted) phenyl or (substituted) heteroaryl

Carboxylic acid derivatives of general formula II-i, accessible by saponification of corresponding alkyl esters II-h, can be condensed with amines of general structure $R^{10}R^{11}NH$ using a coupling reagent as described before for the preparation of derivatives I-a to give compounds of formula I-d, wherein $R^1$, $R^2$, $R^3$, $R^{10}$, $R^{11}$, X, Y and Z are as previously defined and A is a (substituted) phenyl or a (substituted) heteroaryl ring. A similar coupling method has been described before for the preparation of derivatives I-a. Alternatively, compounds of general formula II-i can be converted to the corresponding acid chlorides II-j by art known methods. Treatment of carboxylic acids of general formula II-i with thionyl chloride or oxalyl chloride and DMF in a suitable solvent such as dichloromethane or toluene gives the corresponding

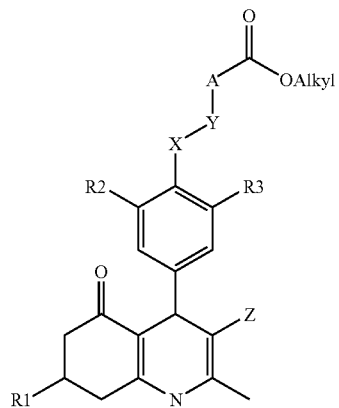
II-h: A = (substituted) phenyl or (substituted) heteroaryl

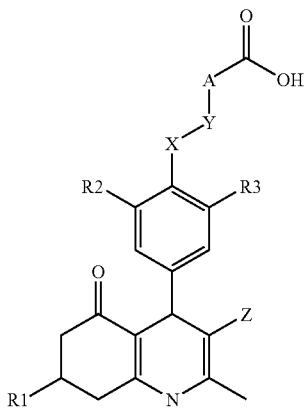
II-i: A = (substituted) phenyl or (substituted) heteroaryl

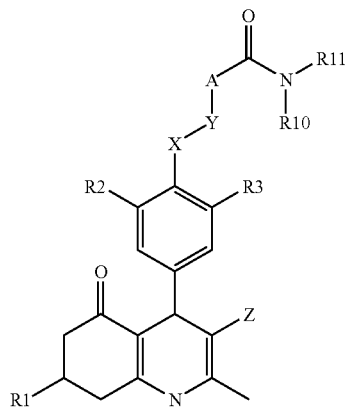
I-d: A = (substituted) phenyl or (substituted) heteroaryl

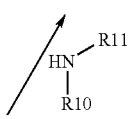

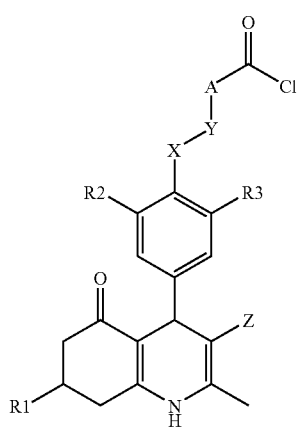
II-j: A = (substituted) phenyl or (substituted) heteroaryl

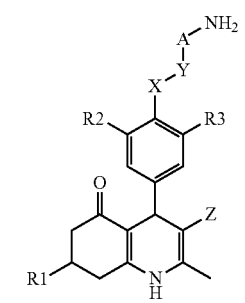
II-b: A = (substituted) phenyl or (substituted) heteroaryl

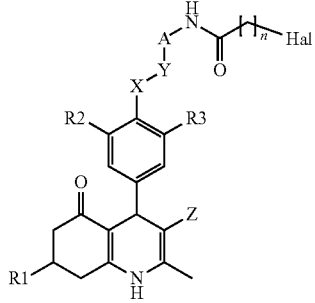
II-k: A = (substituted) phenyl or (substituted) heteroaryl
Hal = Br, Cl
n = 1-4

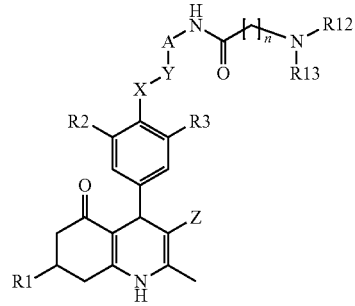
I-e: A = (substituted) phenyl or (substituted) heteroaryl
n = 1-4

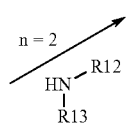

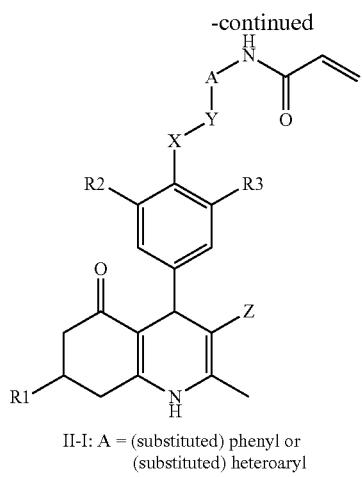

II-I: A = (substituted) phenyl or (substituted) heteroaryl acid chlorides II-j. Subsequent reaction with amines of general structure $R^{10}R^{11}NH$, optionally in the presence of a suitable tertiary amine base yields compounds of general formula I-d.

Compounds of general formula I-e, wherein $R^1$, $R^2$, $R^3$, $R^{12}$, $R^{13}$, X, Y and Z are as previously defined and A is a (substituted) phenyl or a (substituted) heteroaryl ring, can be obtained by acylation of compounds of general formula I-b with appropriate acyl halides to give compounds I-k, followed by standard substitution of the chloride or bromide with amines of general formula $R^{12}R^{13}NH$. Additionally, compounds of general formula I-e with a two-carbon spacer between the carbonyl and the $NR^{12}R^{13}$ group can be obtained by acylation of compounds of general formula II-b with α,β-unsaturated acyl chlorides to give compounds of general formula II-l, followed by art known Michael addition reactions with appropriately substituted amines of general formula $R^{12}R^{13}NH$.

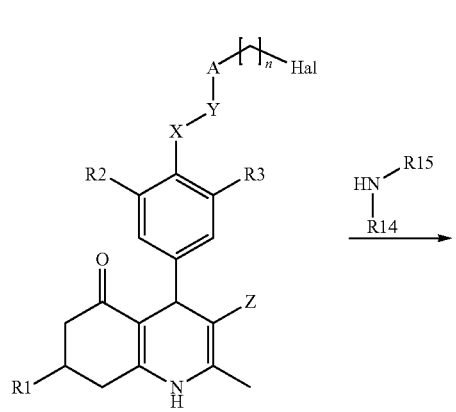

II-m: A = (substituted) phenyl or (substituted) heteroaryl
Hal = Br, Cl or I
n = 1-4

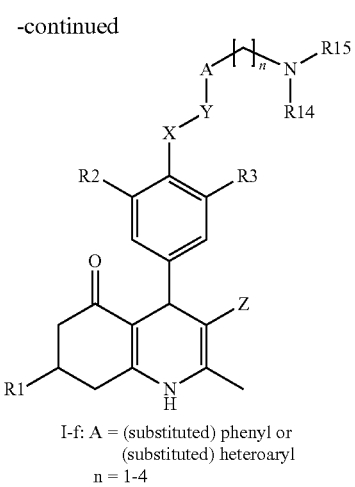

I-f: A = (substituted) phenyl or (substituted) heteroaryl
n = 1-4

Compounds of general formula I-f, wherein $R^1$, $R^2$, $R^3$, $R^{14}$, $R^{15}$, X, Y and Z are as previously defined and A is a (substituted) phenyl or a (substituted) heteroaryl ring, can be prepared by alkylation of amines of general formula $R^{14}R^{15}NH$ with halides of general formula II-m, under the agency of a tertiary base such as N,N-diisopropyl ethylamine or triethylamine in an appropriate solvent such as N,N-dimethylformamide, tetrahydrofuran or dichloromethane.

Derivatives of general formula I-g, wherein $R^1$, $R^2$, $R^3$, $R^{16}$, X, Y and Z are as previously defined and A is a (substituted) phenyl or a (substituted) heteroaryl ring, can be prepared by alkylation of the hydroxyl group in compounds of general formula II-o with an alkyl halide of general formula $R^{16}$—Hal, in which Hal may be Br, Cl or I. Typically, such a reaction is carried out in an aprotic solvent such as N,N-dimethylformamide, 1,4-dioxane or tetrahydrofuran in the presence of a base, such as sodium hydride, potassium carbonate, cesium carbonate or trietyl amine at ambient or elevated temperature. Alternatively, conversion of compounds of general formula II-o into aryl ethers of general formula I-g may be accomplished under Mitsunobu-type alkylation conditions. In such a transformation, alkylation of the hydroxyl group in compounds of formula II-o is effected with alcohols of general formula $R^{16}$—OH under the agency of (resin bound) triphenyl phosphine and diethyl azodicarboxylate or its derivatives in a suitable aprotic solvent such as tetrahydrofuran or dichloromethane.

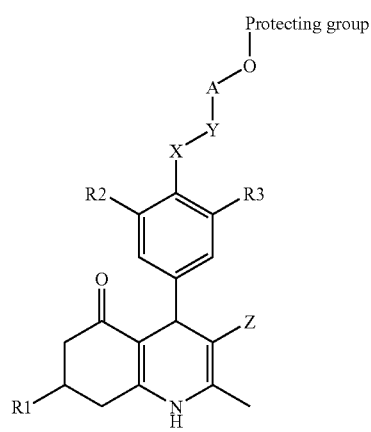

II-n: A = (substituted) phenyl or (substituted) heteroaryl

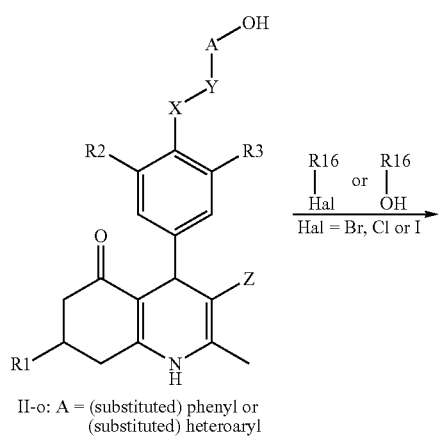

II-o: A = (substituted) phenyl or (substituted) heteroaryl

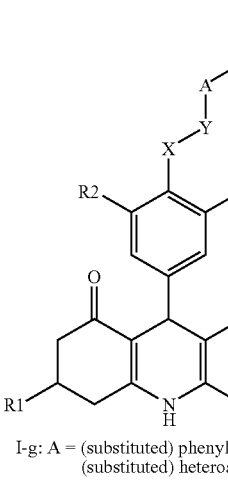

I-g: A = (substituted) phenyl or (substituted) heteroaryl

Derivatives of general formula II-o can be obtained by cleavage of the hydroxyl-protecting group in compounds of general formula I-n. Suitable protective groups, well-known to those skilled in the art, are the tetrahydropyranyl (THP) or tert-butyl dimethylsilyl (TBS) protective groups. Cleavage of the THP and TBS groups is generally accomplished by treatment with acids, such as hydrochloric acid, trifluoromethanesulfonic acid or trifluoroacetic acid in a suitable solvent, such as tetrahydrofuran or methanol. Alternatively, the TBS group can be removed by treatment with tetra-n-butylammonium fluoride in tetrahydrofuran. Related protective group manipulations can be found in *Protective groups in Organic Synthesis*, T. W. Greene and P. G. M. Wuts, John Wiley & sons, Inc., New York, 1999.

Compounds of the present invention with general formula I-h can be prepared by condensation of derivatives II-q with amines of general formula $R^{17}R^{18}NH$ under the agency of a coupling agent and a tertiary amine base, as described e.g for the

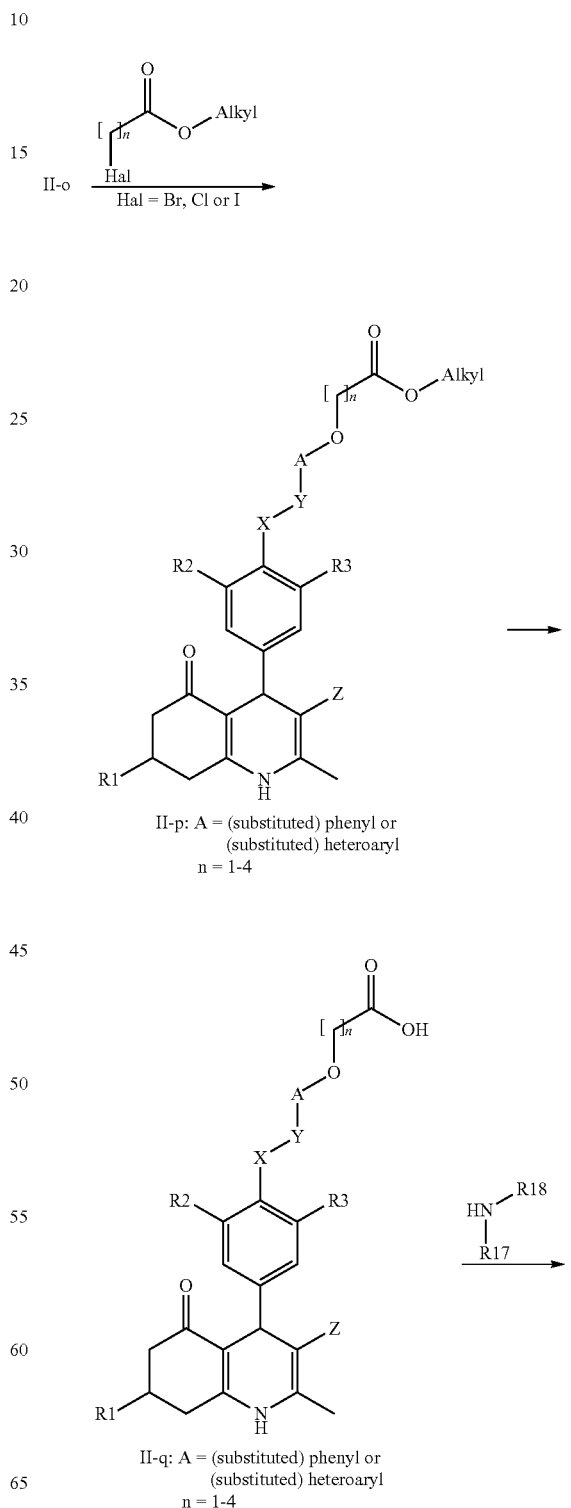

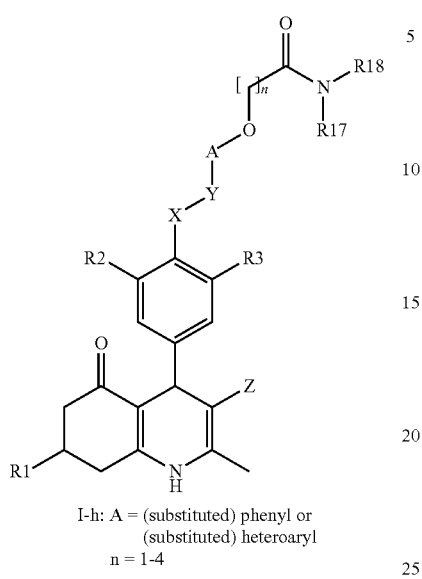

I-h: A = (substituted) phenyl or
(substituted) heteroaryl
n = 1-4

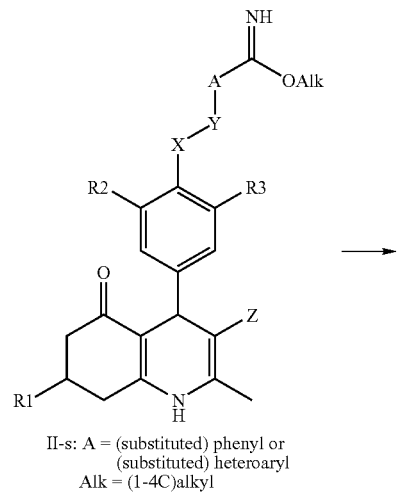

II-s: A = (substituted) phenyl or
(substituted) heteroaryl
Alk = (1-4C)alkyl preparation of derivatives of general formula I-d. The requisite derivatives of formula I-q are accessible in a two-step synthetic protocol from compounds of general formula II-o, i.e. alkylation of the phenolic moiety with an appropriate halogenated alkyl ester to obtain derivatives of formula II-p, followed by acid or base-mediated cleavage of the ester function, well known to those skilled in the art.

Derivatives of general formula I-i are accessible from nitrites of general formula II-r by the art known Pinner amidine synthesis. This synthetic procedure comprises the selective conversion of the nitrile function on the (hetero)aryl ring of derivatives II-r

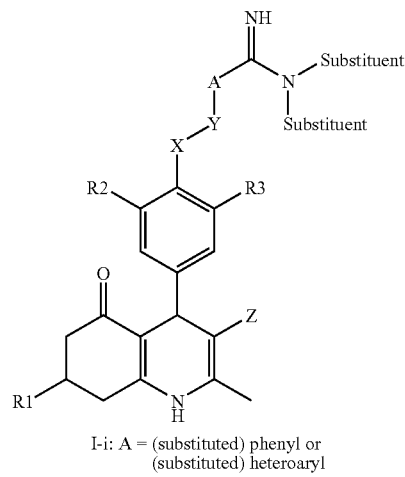

I-i: A = (substituted) phenyl or
(substituted) heteroaryl

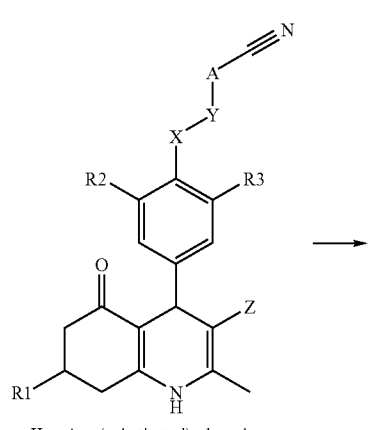

II-r: A = (substituted) phenyl or
(substituted) heteroaryl into imidates II-s by treatment with an appropriate acid such as hydrochloric acid, using a suitable alcohol as a solvent, optionally in the presence of cosolvents such as 1,4-dioxane or diethyl ether, at ambient or elevated temperature. Reaction with the appropriate acyclic or cyclic amine yields the amidine derivatives I-i. Related amidine formations are well known to those skilled in the art. For example, see: J. Med. Chem. 42 (1999) 5415-5425, Bioorg. Med. Chem. Lett. 13 (2003) 697-700, J. Org. Chem. 62 (1997), 8449-8454.

Compounds of general formula III-a wherein X is O can be used to prepare compounds I-j, wherein $R^1$, $R^2$, $R^3$, $R^4$, Y and Z are as previously defined and X is O, by O-alkylation, O-acylation or O-sulfonylation using standard conditions, well known to those skilled in the art. The substitution pattern of the (hetero)aryl ring in $R^4$ is as previously defined. In a typical experiment, compounds III-a are reacted in a solvent, such as dichloromethane, N,N-dimethylformamide, dimethyl sulfoxide, ethanol, tetrahydrofuran, 1,4-dioxane, toluene, 1-methyl-pyrrolidin-2-one or pyridine with an appropriately substituted (hetero)aromatic alkyl halide of formula IV, acyl chloride of formula V, or sulfonyl chloride of formula VII in the presence of a base such as triethylamine, N,N-diisopropylethylamine (DiPEA), potassium carbonate, cesium carbonate or sodium hydride, optionally in the presence of a catalytic amount of potassium iodide or tetrabutylammonium iodide, to give O-alkylated, O-acylated or O-sulfonylated derivatives of formula I-j, respectively.

Alternatively, O-alkylated compounds of general formula I-j in which Y is CH₂ can be obtained by using art known Mitsunobu reactions with alcohols of formula VIII, triphenylphosphine (optionally resin bound) and a dialkyl azodicarboxylate (e.g. diethyl azodicarboxylate) in appropriate solvents such as 1,4-dioxane, tetrahydrofuran or dichloromethane at elevated or ambient temperature.

Additionally, O-acylated compounds of general formula I-j, wherein Y is C(O) can be obtained by reaction of a (hetero) aromatic carboxylic acid of formula VI in the presence of a coupling reagent such as diisopropyl carbodiimide (DIC), (3-dimethylaminopropyl)-ethyl-carbodiimide (EDCI), O-(benzotriazol-1-yl)-N,N,N',N'-tetramethyluronium tetrafluoroborate (TBTU) or O-(7-azabenzotriazol-1-yl)-N,N,N',N'-tetramethyluronium hexafluorophosphate (HATU) and a tertiary amine base (e.g. DiPEA) in a solvent such as N,N-dimethylformamide or dichloromethane at ambient or elevated temperature.

Likewise, compounds of general formula I-k can be prepared from compounds II-b by N-alkylation, N-acylation or N-sulfonylation using the same methods described for the

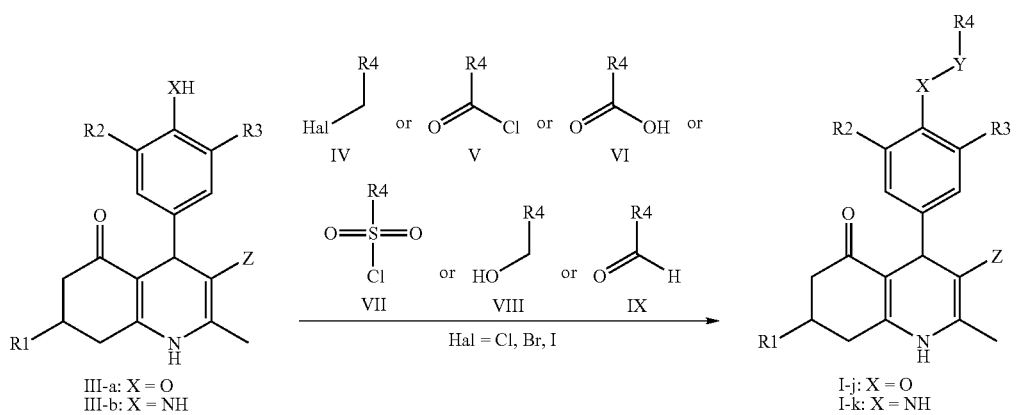

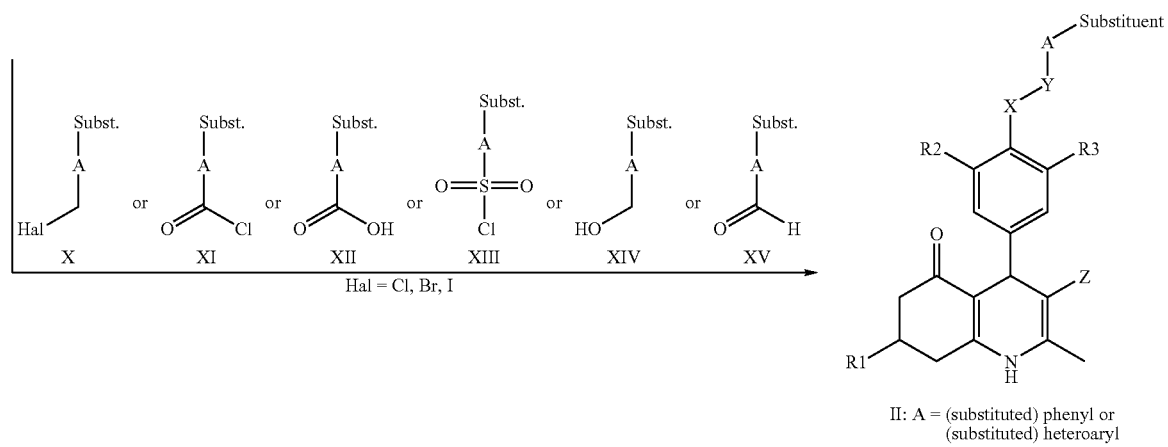

synthesis of compounds I-j using the reagents of formula IV-X. Additionally, compounds of general formula I-k in which Y is CH$_2$ can be prepared by reductive amination of (hetero)aromatic aldehydes of formula IX with compounds II-b and a suitable reducing agent such as sodium cyanoborohydride or sodium triacetoxyborohydride.

Alternatively, compounds of general formula III-b can be converted to the corresponding benzimine upon reaction with (hetero)aromatic aldehydes IX by methods known to those skilled in the art, followed by reduction with a reducing agent such as sodium borohydride to give compounds I-k in which Y=CH$_2$.

Compounds of general formula I-k wherein R$^1$, R$^2$, R$^3$, R$^4$ and Z are as previously defined and X is NH can be N-alkylated by the same methods as described for the preparation of derivatives I-b to afford compounds of general formula I-l, wherein R$^{22}$ is a (1-4C)alkyl group.

Compounds of general formula II are also accessible from derivatives of general formula III-a and III-b using the same methods as described for the preparation of compounds of general formula I-j and I-k using reagents of formula X-XV.

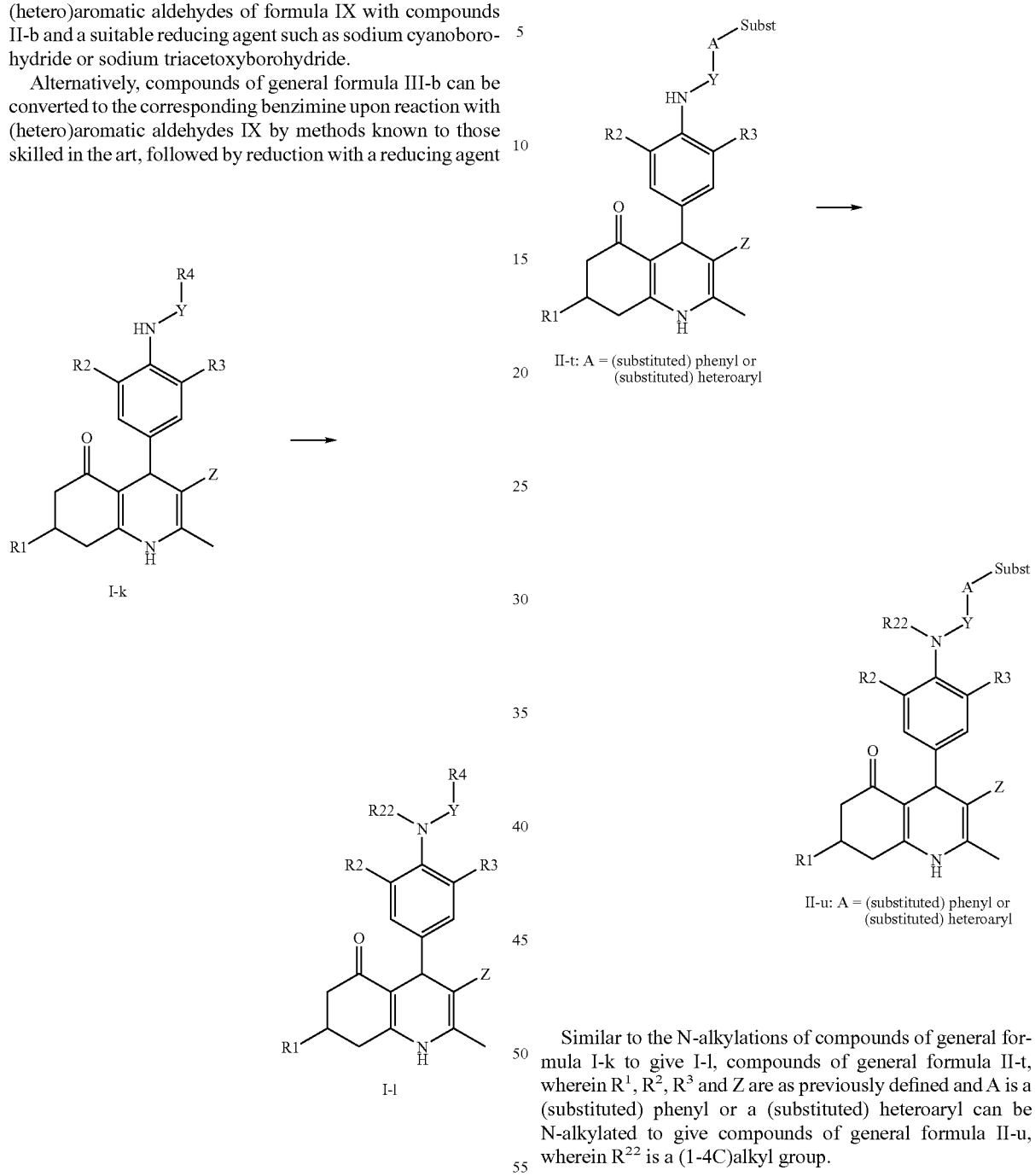

II-t: A = (substituted) phenyl or (substituted) heteroaryl

II-u: A = (substituted) phenyl or (substituted) heteroaryl

Similar to the N-alkylations of compounds of general formula I-k to give I-l, compounds of general formula II-t, wherein R$^1$, R$^2$, R$^3$ and Z are as previously defined and A is a (substituted) phenyl or a (substituted) heteroaryl can be N-alkylated to give compounds of general formula II-u, wherein R$^{22}$ is a (1-4C)alkyl group.

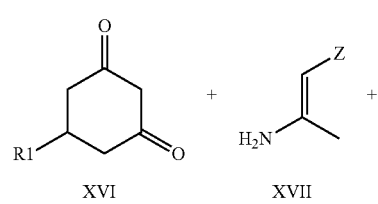

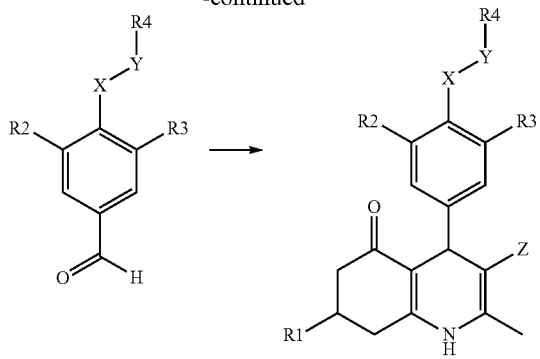

XVIII-a: X = O
XVIII-b: X = N-R22

Compounds of general formula I, wherein $R^1$, $R^2$, $R^3$, $R^4$, X, Y and Z are as previously defined, can also be prepared starting from cyclohexane-1,3-diones of general formula XVI, enamines of general formula XVII and benzaldehydes of general formula XVIII-a-b, by the well-documented three component Hantzsch-type cyclo-condensation reaction.

Related Hantzsch-type cyclo-condensation reactions can be found in: Bioorg. Med. Chem. Lett. 12 (2002) 1481-1484, J. Chem. Soc., Perkin Trans. 1 (2002) 1141-1156, Synlett (2002) 89-92, Drug Dev. Res. 51 (2000) 225-232, Drug Dev. Res. 51 (2000) 233-243, J. Med. Chem. 42 (1999) 1422-1427, ibid. 5266-5271, ibid. 41 (1998) 2643-2650, WO 9408966, Arzneim.-Forsch./Drug Res. 45 (1995) 1054-1056, J. Med. Chem. 34 (1991) 2248-2260, ibid. 17 (1974) 956-65, Indian J. Chem., Sect B (1994) 526-531, Chem. Rev. 72 (1972), 1-42. The above mentioned reaction is typically conducted at elevated temperature in suitable solvents such as acetic acid, (iso)propanol, ethanol, methanol or mixtures thereof.

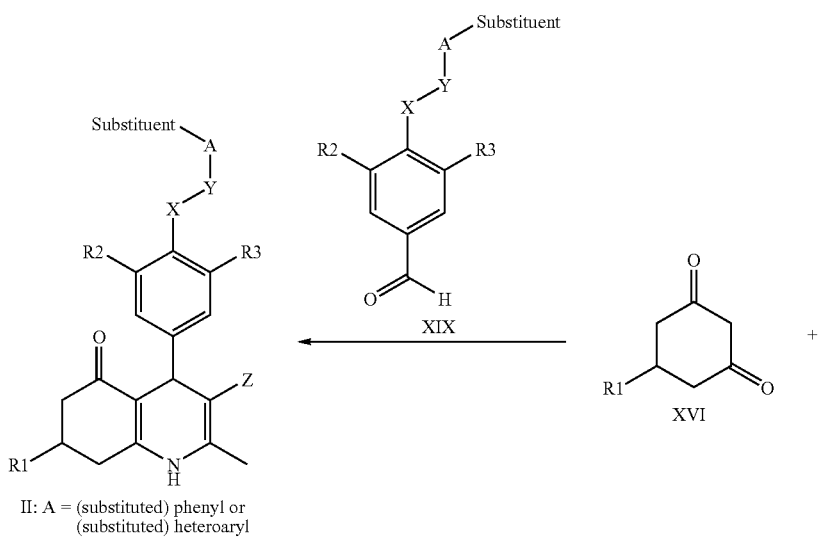

II: A = (substituted) phenyl or (substituted) heteroaryl

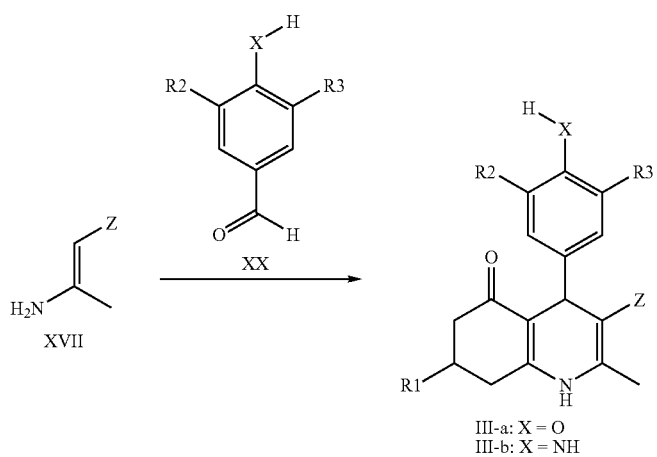

III-a: X = O
III-b: X = NH

Compounds of general formula II and III-a-b are also prepared by the previously mentioned Hantzsch-type cyclo-condensation, by using substituted benzaldehydes of general formula XIX or XX, respectively.

Compounds of general formula III-c-d in which $R^2$ is Br can also be obtained by ortho-bromination of phenols or anilines, which are well known to those skilled in the art. Thus, compounds of formula III-e-f afford compounds of formula III-c-d upon treatment with bromine in a suitable solvent such as acetic acid, ethanol or dichloromethane or mixtures thereof, optionally in the presence of sodium acetate. Alternatively, N-bromosuccinimide in N,N-dimethylformamide or acetonitrile can be used to achieve this conversion. For example, see: J. Chem. Soc. Perkin Trans. 2 6 (2000) 1113-1118, J. Org. Chem. 44 (1979), 4733-4735.

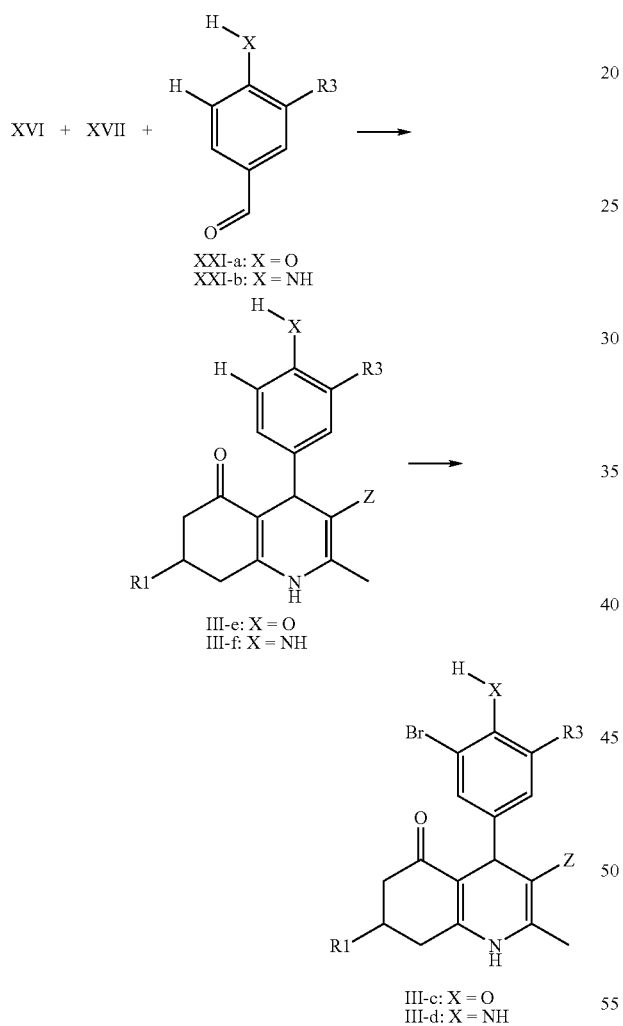

Compounds of general formula III-e-f are prepared by the aforementioned Hantzsch reaction using benzaldehydes of general formula XXI-a-b.

Compounds of general formula IV to XV are either commercially available, documented in literature or readily synthesized by those skilled in the art.

The substituted cyclohexane-1,3-diones of general formula XVI are commercially available or can be prepared by literature procedures. Relevant examples are found in: J. Med. Chem. 43 (2000) 4678-4693, Tetrahedron 56 (2000) 4753-4758, J. Med. Chem. 35 (1992) 3429-3447, ibid. 24 (1981) 1026-1034, Org. Synt. Coll. Vol. V (1973) 400, Chem. Ber. 88 (1955) 316-327, Justus Liebig Ann. Chem. 570 (1950) 15-31.

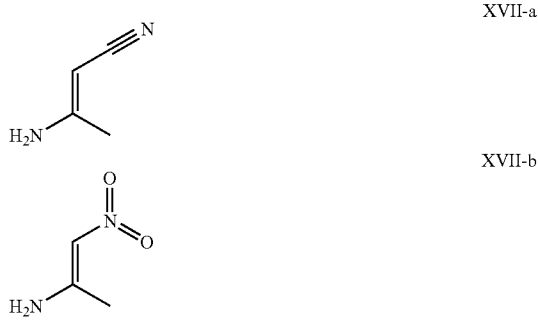

The compound of formula XVII-a is commercially available and compound XVII-b can be prepared by art-known methods, see for example: Drug Dev. Res. 51 (2000) 225-232.

Benzaldehydes of general formula XVIII-a, wherein $R^2$, $R^3$, $R^4$ and Y are as previously defined and X=O, are readily prepared from benzaldehydes of general formula XX-a using the same methods as described for the conversion of compounds of formula III-a to I-j. Likewise compounds of general formula XVIII-b are prepared from XX-b using the same methods as described for the conversion of compounds of formula III-b to I-k.

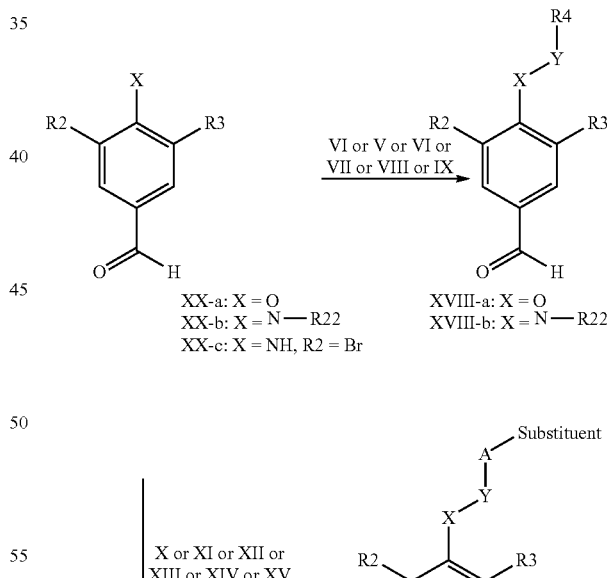

Benzaldehydes of general formula XX-a and XX-b are commercially available or can be prepared according to literature procedures: J. Chem. Soc., Perkin Trans. 2 (2000) 1119-1124, J. Chem. Soc., Chem. Commun. 4 (1993) 419-420, Synth. Commun. 20 (1990) 2659-2666, Chem. Pharm. Bull. 34 (1986) 121-129, Indian J. Chem. Sect. B 20 (1981) 1010-1013, Monatsh. Chem. 106 (1975) 1191-1201, DE 1070162, J. Org. Chem. 23 (1958) 120, Tetrahedron Lett. 25 (1984), 2901-2904, J. Org. Chem. 25 (1960), 2053-2055, J. Chem. Soc., Perkin Trans. 2 (1992), 2235-2242. Additionally, benzaldehydes of general formula XX-c wherein $R^2$ is bromide and X is N—H can be obtained by bromination of compounds of general formula XXI using the same procedures described for the conversion of compounds of general formula III-f to III-d.

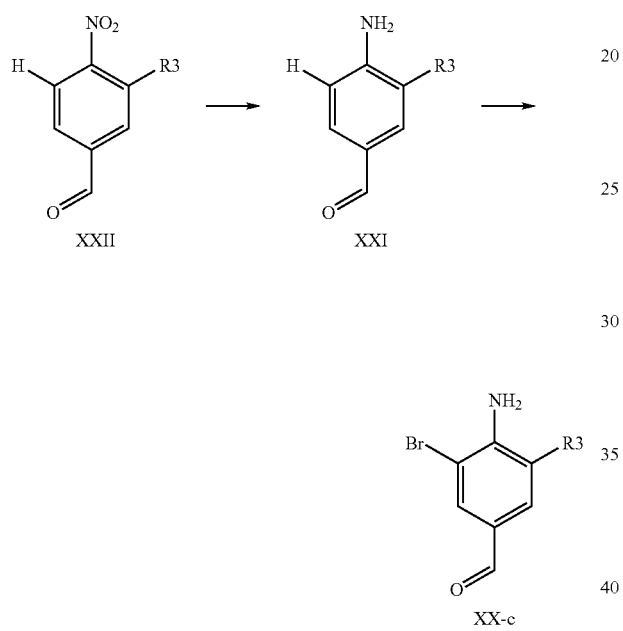

Compounds of general formula XXI are easily prepared from compounds of general formula XXII using the same reduction methods that were described for the preparation of compounds of general formula II-b from II-a. Compounds of general formula XXII are commercially available, reported in literature or can be readily be prepared by those skilled in the art.

Similarly, derivatives of general formula XIX-a-b are accessible from compounds XX-a-b upon reaction with compounds X to XV, as previously described for the preparation of derivatives XVIII-a-b.

The compounds of the present invention possess at least two chiral carbon atoms and may therefore be obtained as pure enantiomers, or as a mixture of enantiomers, or as a mixture of diastereomers. Methods for obtaining the pure enantiomers are well known in the art, e.g. crystallization of salts which are obtained from optically active acids and the racemic mixture, or chromatography using chiral columns. For separation of diastereomers, straight phase or reversed phase columns may be used.

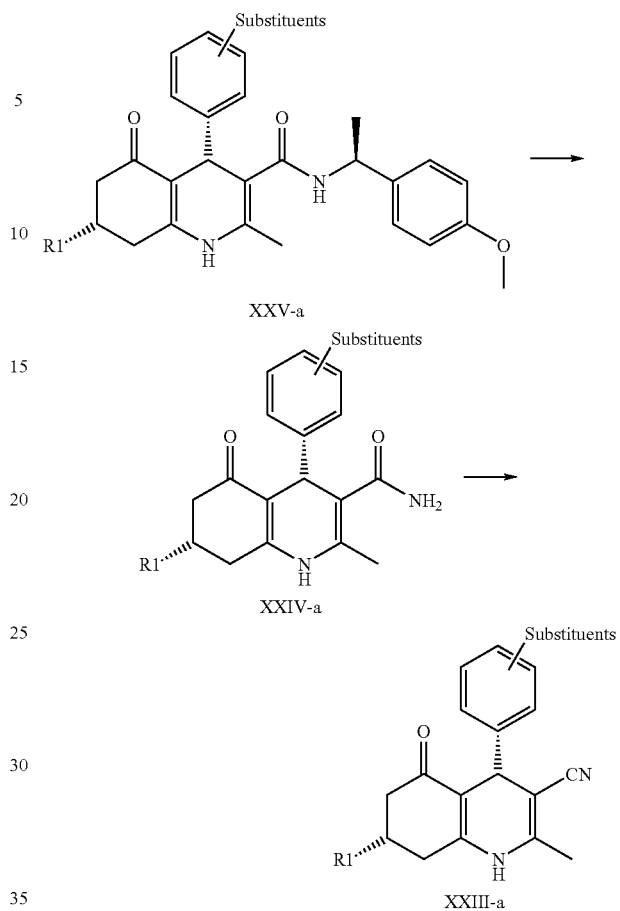

Additionally, enantiomerically pure hexahydroquinoline derivatives of general formula XXIII may be obtained in enantiomerically pure form by dehydration of enantiomerically pure amides XXIV with trifluoroacetic anhydride and a suitable base such as triethylamine or pyridine in a suitable solvent such as dichloromethane, 1,4-dioxane or tetrahydrofuran at 0° C. or ambient temperature. Related dehydrations of amides to give nitrites can be found in literature, for example, see: Org. Prep. Proced. Int. 26 (1994) 429-438, Acta Chem. Scand. 53 (1999) 714-720, J. Org. Chem. 57 (1992) 2700-2705. Compounds of general formula XXIII may then be converted—if necessary—to compounds of general formula I by the syntheses outlined above. Amides of general formula XXIV can be prepared by cleavage of the chiral benzyl group of amides of general formula XXV (indicated for XXV-a). This reaction can be effected by stirring with an acid such as trifluoroacetic acid in dichloromethane.

Compounds of general formula XXV are obtained by a Hantzsch-type cyclo-condensation as described previously, starting from XVI, enamine XXVI and an appropriately substituted benzaldehyde. This reaction gives a mixture of 4 stereoisomers of general formulas XXVa-d which may be separated by chromatographic techniques, such as flash column chromatography using silica gel and/or HPLC.

Enamine XXVI can be prepared by methods known to those of skill in the art in two steps from the commercially available (S)-1-(4-Methoxy-phenyl)-ethylamine and diketene or 2,2,6-trimethyl-1,3-dioxin-4-one.

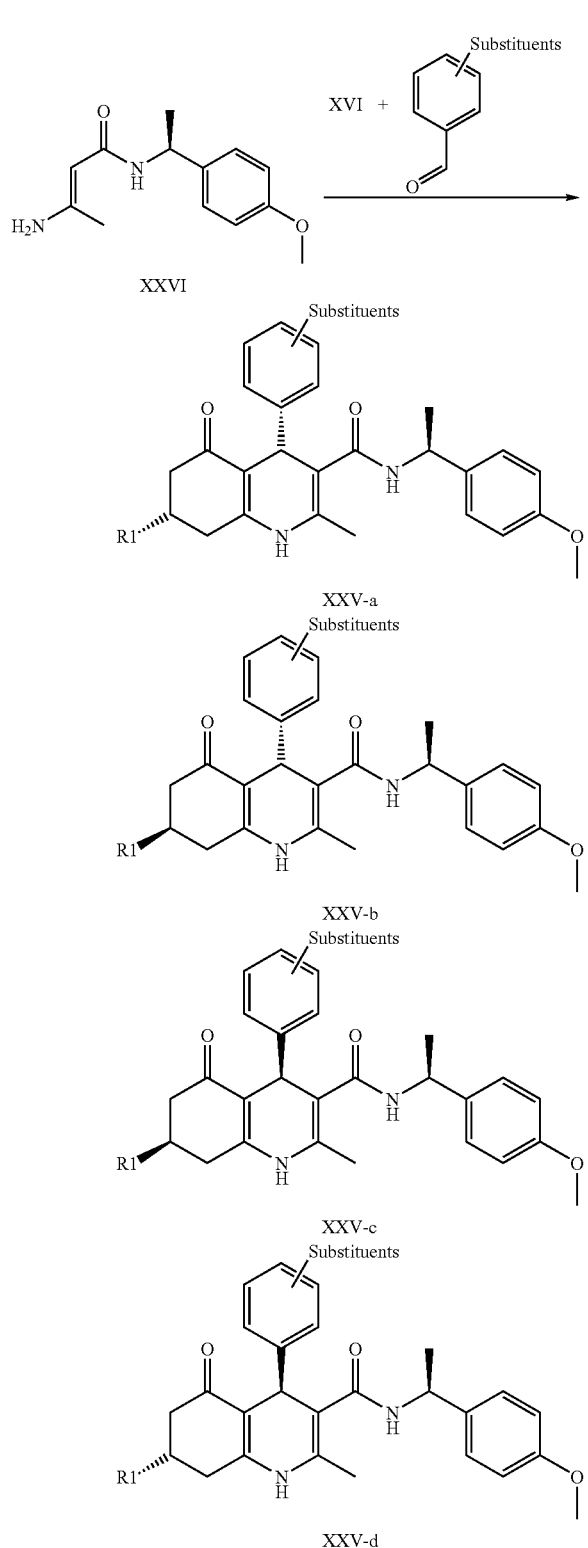

The compounds of the invention may form hydrates or solvates. It is known to those of skill in the art that charged compounds form hydrated species when lyophilized with water, or form solvated species when concentrated in a solution with an appropriate organic solvent. The compounds of this invention include the hydrates or solvates of the compounds listed.

The 4-phenyl-5-oxo-1,4,5,6,7,8-hexahydroquinoline derivatives of the invention were found to agonists of the FSH receptor. Methods to determine receptor binding, as well as in vitro and in vivo assays to determine biological activity, of gonadotropins are well known. In general, expressed receptor is contacted with the compound to be tested and binding or stimulation or inhibition of a functional response is measured.

To measure a functional response, isolated DNA encoding the FSH receptor gene, preferably the human receptor, is expressed in suitable host cells. Such a cell might be the Chinese Hamster Ovary cell, but other cells are also suitable. Preferably the cells are of mammalian origin (Jia et al, Mol. Endocrin., 5:759-776, 1991).

Methods to construct recombinant FSH expressing cell lines are well known in the art (Sambrook et al., Molecular Cloning: a Laboratory Manual, Cold Spring Harbor Laboratory Press, Cold Spring Harbor, latest edition). Expression of receptor is attained by expression of the DNA encoding the desired protein. Techniques for site directed mutagenesis, ligation of additional sequences, PCR, and construction of suitable expression systems are all, by now, well known in the art. Portions, or all, of the DNA encoding the desired protein can be constructed synthetically using standard solid phase techniques, preferably to include restriction sites for ease of ligation. Suitable control elements for transcription and translation of the included coding sequence can be provided to the DNA coding sequences. As is well known, expression systems are now available which are compatible with a wide variety of hosts, including prokaryotic hosts such as bacteria and eukaryotic hosts such as yeast, plant cells, insect cells, mammalian cells, avian cells and the like.

Cells expressing the receptor are then contacted with the test compound to observe binding, or stimulation or inhibition of a functional response.

Alternatively, isolated cell membranes containing the expressed receptor may be used to measure binding of the test compound.

For measurement of binding, radioactive or fluorescent compounds may be used. As reference compound human recombinant FSH can be used.

In the alternative also competition binding assays may be performed.

Another assay involves screening for FSH receptor agonist compounds by determining stimulation of receptor mediated cAMP accumulation. Thus, such a method involves expression of the receptor on the cell surface of a host cell and exposing the cell to the test compound. The amount of cAMP is then measured. The level of cAMP will be increased, by the stimulating effect of the test compound upon binding to the receptor.

In addition to direct measurement of e.g. cAMP levels in the exposed cell, cells lines can be used which in addition to transfection with receptor encoding DNA are also transfected with a second DNA encoding a reporter gene the expression of which responds to the level of cAMP. Such reporter genes might be cAMP inducible or might be constructed in such a way that they are connected to novel cAMP responsive elements. In general, reporter gene expression might be controlled by any response element reacting to changing levels of cAMP. Suitable reporter genes are e.g. LacZ, alkaline phosphatase, firefly luciferase and green fluorescence protein. The principles of such transactivation assays are well known in the art and are described e.g. in Stratowa, Ch., Himmler, A. and Czernilofsky, A. P., (1995) Curr. Opin. Biotechnol. 6:574.

The present invention also relates to a pharmaceutical composition comprising a 4-phenyl-5-oxo-1,4,5,6,7,8-hexahydroquinoline derivative or pharmaceutically acceptable salts thereof having the general formula I in admixture with pharmaceutically acceptable auxiliaries and optionally other therapeutic agents. The auxiliaries must be "acceptable" in the sense of being compatible with the other ingredients of the composition and not deleterious to the recipients thereof.

Compositions include e.g. those suitable for oral, sublingual, subcutaneous, intravenous, intramuscular, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable auxiliaries, e.g. as described in the standard reference, Gennaro, A. R. et al., Remington: *The Science and Practice of Pharmacy* (20th Edition., Lippincott Williams & Wilkins, 2000, see especially Part 5: Pharmaceutical Manufacturing), the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a suitable dosage for humans may be 0.05-25 mg per kg body weight. The desired dose may be presented as one dose or as multiple subdoses administered at appropriate intervals throughout the day, or, in case of female recipients, as doses to be administered at appropriate daily intervals throughout the menstrual cycle. The dosage as well as the regimen of administration may differ between a female and a male recipient.

Thus, the compounds according to the invention can be used in therapy.

A further aspect of the invention resides in the use of a 4-phenyl-5-oxo-1,4,5,6,7,8-hexahydroquinoline derivative having the general formula I for the manufacture of a medicament to be used for the treatment of disorders responsive to FSH receptor mediated pathways, preferably for the treatment of fertility disorders. Thus, patients in need thereof can be administered with suitable amounts of the compounds according to the invention.

In yet another aspect the invention resides in the use of a 4-phenyl-5-oxo-1,4,5,6,7,8-hexahydroquinoline derivative having the general formula I for the manufacture of a medicament to be used for the treatment of infertility.

The invention is illustrated by the following examples.

General Comments:

The following abbreviations are used in the examples: DMA=N,N-dimethylaniline, DIPEA=N,N-diisopropylethylamine, TFA=trifluoroacetic acid, HATU=O-(7-azabenzotriazole-1-yl)-N,N,N',N'-tetramethyluronium hexafluorophosphate, Fmoc=9-fluorenylmethoxycarbonyl, Fmoc-Cl=9-fluorenylmethoxycarbonylchloride, Alloc=allyloxycarbonyl, DMF=N,N-dimethylformamide, THF=tetrahydrofuran.

Unless stated otherwise, all final products of the examples below were lyophilized from water/1,4-dioxane mixtures, water/tert-butanol or water/acetonitrile mixtures. If the compound was prepared as a TFA salt, the acid was added in an appropriate amount to the solvent mixture before lyophilization.

The names of the final products described in the examples were generated using the Beilstein Autonom program (version: 2.02.304).

The following analytical HPLC methods were used for determination of retention times:

Method 1: Column: 5 μm Luna C-18(2) 150×4.6 mm; flow: 1 ml/min; detection: 210 nm; column temperature: 40° C.; solvent A: $CH_3CN/H_2O=1/9$ (v/v); solvent B: $CH_3CN$; solvent C, 0.1 M aqueous trifluoroacetic acid; gradient: solvent A/B/C=65/30/5 to 10/85/5 (v/v/v) in 30.00 min, then constant for an additional 10.00 min at A/B/C=10/85/5 (v/v/v).

Method 2: Identical to method 1, except for the gradient used: Gradient: solvent A/B/C=75/20/5 to 15/80/5 (v/v/v) in 30.00 min, then constant for an additional 10.00 min at A/B/C=15/80/5 (v/v/v).

Method 3: Identical to method 1, except for the gradient used: Gradient: solvent A/B/C=35/60/5 to 10/85/5 (v/v/v) in 30.00 min, then constant for an additional 10.00 min at A/B/C=10/85/5 (v/v/v).

Method 4: Identical to method 1, except for the gradient used: Gradient: solvent A/B/C=95/0/5 to 15/80/5 (v/v/v) in 30.00 min, then constant for an additional 10.00 min at A/B/C=15/80/5 (v/v/v).

Method 5: Identical to method 1, except for the gradient used: Gradient: solvent A/B/C=75/25/0 to 0/100/0 (v/v/v) in 20.00 min, then constant for an additional 10.00 min at A/B/C=0/100/0 (v/v/v).

Method 6: Identical to method 1, except for the gradient used: Gradient: solvent A/B/C=60/40/0 to 0/100/0 (v/v/v) in 20.00 min, then constant for an additional 10.00 min at A/B/C=0/100/0 (v/v/v).

Method 7: Identical to method 1, except for the gradient used: Gradient: solvent A/B/C=70/30/3 to 40/60/3 (v/v/v) in 30.00 min, then constant for an additional 10.00 min at A/B/C=0/100/3 (v/v/v).

Method 8: Column: 3 μm Luna C-18(2) 100×2 mm (Phenomenex); flow: 0.25 ml/min; detection: 210 nm; column temperature: 40° C.; solvent A: $CH_3CN/H_2O=1/9$ (v/v); solvent B: $CH_3CN$; gradient: solvent A/B=65/35 to 10/90 (v/v) in 30.00 min, in 2.00 minutes to A/B=0/100 (v/v), then constant for an additional 8.00 min at A/B=0/100 (v/v), then in 1.00 minute to A/B=65/35 (v/v) and finally constant for an additional 15.00 min at A/B=65/35 (v/v).

Method 9: Column: Chiralpak AD-H 25×0.46 cm; detection: Chirality (+/−) and 210 nm; Conditions: isocratic heptane/isopropylalcohol 80/20 (v/v).

The diastereomeric ratio (Diast. ratio:) was determined if baseline separation of the individual diastereomers was observed using the appropriate analytical HPLC method. Alternatively, the diastereomeric ratio was determined by $^1$H NMR analysis when distinct signals corresponding to the diastereomers were identified.

Preparative HPLC-purifications were performed on a Luna C-18(2) column (5 µm) (150×21.2 mm) with water/acetonitrile mixtures, optionally in the presence of 0.1% aqueous TFA, using the indicated gradient: Flow: 20 ml/min: Detection: 210 nm:

EXAMPLE 1

N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-3,4,5-trimethoxy-benzamide (a). 3-Bromo-5-ethoxy-4-(3-nitro-benzyloxy)-benzaldehyde A mixture of 3-nitrobenzylbromide (2 g), 3-bromo-5-ethoxy-4-hydroxy benzaldehyde (2.06 g), K$_2$CO$_3$ (2.55 g) and Bu$_4$NI (186 mg) in DMF (50 ml) was stirred at 60° C. for 2 h. The reaction mixture was diluted with ethyl acetate and washed with water and brine. The organic layer was dried (MgSO$_4$), filtered and concentrated in vacuo. The residue was recrystallized from heptane.

Yield: 2.98 g. MS-ESI: [M+H]$^+$=380/382

(b). 4-[4-(3-Nitro-benzyloxy)-3-bromo-5-ethoxy-phenyl]-2-methyl-5-oxo-7-propyl-1,4,5,6,7,8-hexahydro-quinoline-3-carbonitrile A mixture of the product of example 1a (2 g), 3-aminocrotonitrile (431 mg) and 5-propylcyclohexane-1,3-dione (810 mg) in ethanol (20 ml) was stirred at 80° C. for 4 h. The reaction mixture was concentrated in vacuo and the residue was chromatographed on silica gel in heptane/ethyl acetate=1/1 (v/v) as eluent.

Yield: 2.7 g. MS-ESI: [M+H]$^+$=580/582

(c). 4-[4-(3-Amino-benzyloxy)-3-bromo-5-ethoxy-phenyl]-2-methyl-5-oxo-7-propyl-1,4,5,6,7,8-hexahydro-quinoline-3-carbonitrile SnCl$_2$ (1.62 g) was added to a solution of the product of example 1b (500 mg) in ethanol (10 ml). After stirring for 18 h, the reaction mixture was poured in water and extracted with ethyl acetate. The organic layer was separated and washed with 0.5N NaOH and water, dried (MgSO$_4$), filtered and concentrated in vacuo.

Yield: 440 mg. MS-ESI: [M+H]$^+$=550/552

(d). N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-3,4,5-trimethoxy-benzamide A mixture of the product of example 1c (44 mg), 3,4,5-trimethoxybenzoylchloride (39 mg) and DIPEA (70 µl) in dichloromethane (10 ml) was stirred for 18 h. The reaction mixture was diluted with dichloromethane and washed with water and brine. The organic layer was separated, dried (MgSO$_4$), filtered and concentrated in vacuo. The residue was purified by preparative HPLC (0→90% acetonitrile). Yield: 39 mg. MS-ESI: [M+H]$^+$=744.4/746.4; anal. HPLC: Rt=20.73 min 1 (method 1)

EXAMPLE 2

N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-3,3-dimethyl-butyramide Acylation of the product described in example 1c (44 mg) with 3,3-dimethyl-butyryl chloride (16 mg) was performed according to the method described in example 1d.

Yield: 36 mg. MS-ESI: [M+H]$^+$=648/650; anal. HPLC: Rt=22.58 min (method 1)

EXAMPLE 3

N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-2-[(pyridin-4-ylmethyl)-amino]-acetamide (a). 2-Bromo-N-{3-[2-bromo-4-(3-cyano-2-methyl-5-oxo-7-propyl-1,4,5,6,7,8-hexahydro-quinolin-4-yl)-6-ethoxy-phenoxymethyl]-phenyl}-acetamide Bromoacetyl chloride (600 µl) in dichloromethane (5 ml) was added dropwise to a solution of the product of example 1c (1.32 g) and DIPEA (2.1 ml) in dichloromethane (25 ml). After stirring for 4 h, the reaction mixture was washed with water. The organic layer was separated, dried (MgSO$_4$), filtered and concentrated in vacuo. Yield: 900 mg. MS-ESI: [M+H]$^+$=670/672/674

(b). N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-2-[(pyridin-4-ylmethyl)-amino]-acetamide A mixture of the product of example 3a (50 mg) and 4-picolylamine (81 mg) in dichloromethane/THF=4:1 (v/v) (2.5 ml) was stirred for 18 h. The reaction mixture was diluted with dichloromethane and washed with water and brine. The organic layer was separated, dried (MgSO$_4$), filtered and concentrated in vacuo. The residue was purified by preparative HPLC (0→90% acetonitrile, 0.1% TFA). Yield: 17.9 mg (as TFA salt). MS-ESI: [M+H]$^+$=698.4/700.4; anal. HPLC: Rt=8.85 min (diast1), Rt=9.07 min (diast2) (method 2)

EXAMPLE 4

N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-2-(cyclopentyl-methyl-amino)-acetamide Reaction of the product described in example 3a (50 mg) with cyclopentyl-methylamine (74 mg) was performed according to the method described in example 3b.

Yield: 53 mg (as TFA salt). MS-ESI: [M+H]$^+$=689/691; anal. HPLC: Rt=13.45 min (diast1), Rt=13.72 min (diast2) (method 2).

41

EXAMPLE 5

N-{3-[2-Bromo-4-(3-cyano-2-methyl-5-oxo-7-pro-pyl-1,4,5,6,7,8-hexahydro-quinolin-4-yl)-6-ethoxy-phenoxymethyl]-phenyl}-2-[4-(2-hydroxy-ethyl)-piperazin-1-yl]-acetamide Reaction of the product described in example 3a (50 mg) with 2-piperazin-1-yl-ethanol (98 mg) was performed according to the method described in example 3b. Yield: 41 mg (as TFA salt). MS-ESI: [M+H]$^+$=720/721; anal. HPLC: Rt=10.40 min (diast1) Rt=10.67 min (diast2) (method 2).

EXAMPLE 6

3-[2-Bromo-4-(3-cyano-2-methyl-5-oxo-7-propyl-1,4,5,6,7,8-hexahydro-quinolin-4-yl)-6-ethoxy-phenoxymethyl]-N-ethyl-N-(2-hydroxy-ethyl)-benzamide (a). 3-(2-Bromo-6-ethoxy-4-formyl-phenoxymethyl)-benzoic acid methyl ester Alkylation of 3-bromo-5-ethoxy-4-hydroxy benzaldehyde (2 g) with 3-bromomethyl-benzoic acid methyl ester (2.06 g) was performed according to the method described in example 1a. The residue was chromatographed on silica gel in heptane/ethyl acetate=7/3 (v/v) as eluent. Yield: 2.42 g. MS-ESI: [M+H]$^+$=393/395

(b). 3-[2-Bromo-4-(3-cyano-2-methyl-5-oxo-7-propyl-1,4,5,6,7,8-hexahydro-quinolin-4-yl)-6-ethoxy-phenoxymethyl]-benzoic acid methyl ester The title compound was prepared according to the method described in example 1b starting from the product of example 6a (2.4 g), 3-aminocrotonitrile (504 mg) and 5-propylcyclohexane-1,3-dione (947 mg). Yield: 2.96 g. MS-ESI: [M+H]$^+$=593/595

(c). 3-[2-Bromo-4-(3-cyano-2-methyl-5-oxo-7-propyl-1,4,5,6,7,8-hexahydro-quinolin-4-yl)-6-ethoxy-phenoxymethyl]-benzoic acid A mixture of the product of example 6b (2.96 g) and 2N NaOH (5 ml) in dioxane (100 ml) was stirred for 3 days. The reaction mixture was poured in water followed by addition of 4N HCl until pH 2 and extraction with ethyl acetate. The organic layer was washed with brine, dried (MgSO$_4$), filtered and concentrated in vacuo. Yield: 3.0 g. MS-ESI: [M+H]$^+$=579/581

(d). 3-[2-Bromo-4-(3-cyano-2-methyl-5-oxo-7-propyl-1,4,5,6,7,8-hexahydro-quinolin-4-yl)-6-ethoxy-phenoxymethyl]-N-ethyl-N-(2-hydroxy-ethyl)-benzamide A mixture of the product of example 6c (90 mg), 2-ethylamino-ethanol (49 µl) and TBTU (82 mg) in dichloromethane (5 ml) was stirred for 4 h. The reaction mixture was washed with sat. NaHCO$_3$, dried (MgSO$_4$) and concentrated in vacuo. The residue was purified by preparative HPLC (0→90% acetonitrile, 0.1% TFA). Yield: 43 mg. MS-ESI: [M+H]$^+$=650/652; anal. HPLC: Rt=19.96 min (diast 1), Rt=20.22 min (diast 2) (method 2). Diast. ratio: 3:1

42

EXAMPLE 7

4-{3-Bromo-4-[3-(3,6-dihydro-2H-pyridine-1-carbonyl)-benzyloxy]-5-ethoxy-phenyl}-2-methyl-5-oxo-7-propyl-1,4,5,6,7,8-hexahydro-quinoline-3-carbonitrile Coupling of the compound described in example 6c with 1,2,3,6-tetrahydro-pyridine (47 µl) and TBTU (82 mg) was performed according to the method described in example 6d. Yield: 61 mg. MS-ESI: [M+H]$^+$=644/646; anal. HPLC: Rt=23.48 min (diast 1), Rt=23.75 min (diast 2) (method 2) Diast. ratio: 3:1

EXAMPLE 8

{3-[2-Bromo-4-(3-cyano-2-methyl-5-oxo-7-propyl-1,4,5,6,7,8-hexahydro-quinolin-4-yl)-6-ethoxy-phenoxymethyl]-phenoxy}-acetic acid tert-butyl ester (a). 3-Bromomethyl-phenol At 0° C. and under a nitrogen atmosphere carbontetrabromide (28.05 g) was added over a period of 20 min to a suspension of 3-hydroxybenzylalcohol (7 g) and triphenylphosphine (22.18 g) in dichloromethane (250 ml). After stirring for 1 h at 0° C., the reaction mixture was concentrated in vacuo. The residue was chromatographed on silica gel in heptane/ethyl acetate=2/1 (v/v) as eluent. Yield: 10 g. MS-ESI: [M−H]−=184.8/186.8

(b). 2-(3-Bromomethyl-phenoxy)-tetrahydro-pyran

At 0° C. 3,4-dihydro-2H-pyran (9.8 ml) and a catalytic amount of pyridinium-p-toluenesulfonate were added to a solution of the product of example 8a (10 g) in dichloromethane (300 ml). After stirring for 1.5 h at room temperature, the reaction mixture was diluted with dichloromethane and washed with sat. NaHCO$_3$ and brine. The organic layer was separated, dried (MgSO$_4$), filtered and concentrated in vacuo. The residue was chromatographed on silica gel in heptane/ethyl acetate=4/1 (v/v).
Yield: 13.6 g.

(c). 3-Bromo-5-ethoxy-4-[3-(tetrahydro-pyran-2-yloxy)-benzyloxy]-benzaldehyde

Alkylation of 3-ethoxy-4-hydroxy-5-bromo-benzaldehyde (11.19 g) with the product of example 8b (13.6 g) was performed according to the method described in example 1a. The residue was chromatographed on silica gel in heptane/ethyl acetate=3/1 (v/v) as eluent. Yield: 17.8 g. MS-ESI: [M+H]$^+$=435/437

(d). 4-{3-Bromo-5-ethoxy-4-[3-(tetrahydro-pyran-2-yloxy-benzyloxy]-phenyl}-2-methyl-5-oxo-7-propyl-1,4,5,6,7,8-hexahydro-quinoline-3-carbonitrile The title compound was prepared according to the method described in example 1b, using the product of example 8c (5.5 g), 3-aminocrotonitrile (1 g) and 5-propylcyclohexane-1,3-dione (1.95 g). Yield: 6.4 g. MS-ESI: [M+H]$^+$=635.4/637.4

(e). 4-[3-Bromo-5-ethoxy-4-(3-hydroxy-benzyloxy)-phenyl]-2-methyl-5-oxo-7-propyl-1,4,5,6,7,8-hexahydro-quinoline-3-carbonitrile Oxalic acid was added to a solution of the product of example 8d (6.4 g) in methanol (135 ml) and water (15 ml) to pH 2. After stirring at 55° C. for 2 h, the reaction mixture was concentrated in vacuo. The residue was dissolved in ethyl acetate and washed with water, sat. NaHCO$_3$ and brine. The organic layer was separated, dried (MgSO$_4$), filtered and concentrated in vacuo. Yield: 5.5 g. MS-ESI: [M+H]$^+$=551.2/553.2

(f). {3-[2-Bromo-4-(3-cyano-2-methyl-5-oxo-7-propyl-1,4,5,6,7,8-hexahydro-quinolin-4-yl)-6-ethoxy-phenoxymethyl]-phenoxy}-acetic acid tert-butyl ester A mixture of the product of example 8e (100 mg), tert-butyl bromoacetate (105 mg) and CsCO$_3$ (355 mg) in dioxane (7 ml) was stirred at 80° C. under a nitrogen atmosphere for 18 h. The reaction mixture was diluted with ethyl acetate and washed with water, sat. NaHCO$_3$ and brine. The organic layer was separated, dried (MgSO$_4$), filtered and concentrated in vacuo. The residue was purified by preparative HPLC (50→100% acetonitrile). Yield: 34.5 mg. MS-ESI: [M+H]$^+$=665.4/667.4; anal. HPLC: Rt=10.16 min (diast1), 10.55 min (diast2) (method 3) Diast. ratio: 5:1

EXAMPLE 9

N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-2-(3-pyrrolidin-1-yl-propylamino)-acetamide Reaction of the product described in example 3a (100 mg) with 3-pyrrolidin-1-yl-propylamine (191 mg) was performed according to the method described in example 3b. Yield: 32 mg (as TFA salt). MS-ESI: [M+H]$^+$=718.6/720.6; anal. HPLC: Rt=7.24 min (method 2).

EXAMPLE 10

{3-(Benzyl-methyl-amino)-N-{3-[2-bromo-4-(3-cyano-2-methyl-5-oxo-7-propyl-1,4,5,6,7,8-hexahydro-quinolin-4-yl)-6-ethoxy-phenoxymethyl]-phenyl}-propionamide (a). N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-acrylamide To a solution of the product of example 1c (1.5 g) in dichloromethane was added acryloylchloride (222 µl) and DIPEA (2.38 ml). After stirring for 18 h, the reaction mixture was washed with water. The organic layer was separated, dried (MgSO$_4$), filtered and concentrated in vacuo. Yield: 1.65 g. ESI-MS: [M+H]$^+$=604.2/606.2

(b). {3-(Benzyl-methyl-amino)-N-{3-[2-bromo-4-(3-cyano-2-methyl-5-oxo-7-propyl-1,4,5,6,7,8-hexahydro-quinolin-4-yl)-6-ethoxy-phenoxymethyl]-phenyl}-propionamide A mixture of the product of example 10a (150 mg) and N-methyl-benzylamine (300 mg) in THF (2.5 ml) was stirred for 18 h. The reaction mixture was concentrated in vacuo. The residue was dissolved in ethyl acetate and washed with water. The organic layer was separated, dried (MgSO$_4$), filtered and concentrated in vacuo. The residue was purified by preparative HPLC (10→90% acetonitrile, 0.1% TFA). Yield: 34 mg (as TFA salt). MS-ESI: [M+H]$^+$=725.4/727.4; anal. HPLC: Rt=14.32 min (diast1), Rt=14.58 min (diast2) (method 2)

EXAMPLE 11

3-[Bis-(2-methoxy-ethyl)-amino]-N-{3-[2-bromo-4-(3-cyano-2-methyl-5-oxo-7-propyl-1,4,5,6,7,8-hexahydro-quinolin-4-yl)-6-ethoxy-phenoxymethyl]-phenyl}-propionamide The title compound was obtained according to the method described for example 10b, starting from Bis-(2-methoxy-ethyl)-amine (319 mg) and the product of example 10a (150 mg). Yield: 30 mg (as TFA salt). MS-ESI: [M+H]$^+$=737.4/739.4; anal. HPLC: Rt=13.24 min (method 2).

EXAMPLE 12

4-{3-Bromo-5-ethoxy-4-[3-(pyridin-2-ylmethoxy)-benzyloxy]-phenyl}-2-methyl-5-oxo-7-propyl-1,4,5,6,7,8-hexahydro-quinoline-3-carbonitrile A mixture of the product of example 8e (100 mg), 2-picolylchloride hydrochloride (31.2 mg) and CsCO$_3$ (124 mg) in DMF (7 ml) was stirred at 60° C. under a nitrogen atmosphere for 18 h. The reaction mixture was diluted with ethyl acetate and washed with water, sat. NaHCO$_3$ and brine. The organic layer was separated, dried (MgSO$_4$), filtered and concentrated in vacuo. The residue was purified by preparative HPLC (0→100% acetonitrile, 0.1% TFA). Yield: 19.6 mg (as TFA salt). MS-ESI: [M+H]$^+$=642.1/644.1; anal. HPLC: Rt=17.24 min (method 2).

EXAMPLE 13

4-{3-Bromo-5-ethoxy-4-[3-(4-fluoro-benzyloxy)-benzyloxy]-phenyl}-2-methyl-5-oxo-7-propyl-1,4,5,6,7,8-hexahydro-quinoline-3-carbonitrile The title compound was obtained according to the method described for example 12, starting from 4-fluoro-benzylbromide (23.7 µl) and the product of example 8e (100 mg). The residue was purified by preparative HPLC (50→100% acetonitrile). Yield: 58.9 mg. MS-ESI: [M+H]$^+$=659.2/661.2; anal. HPLC: Rt=14.38 min (diast1), Rt=14.90 min (diast2) (method 3). Diast. ratio: 5:1

EXAMPLE 14

4-{3-Bromo-4-[3-(2-diethylamino-ethoxy)-benzyloxy]-5-ethoxy-phenyl}-2-methyl-5-oxo-7-propyl-1,4,5,6,7,8-hexahydro-quinoline-3-carbonitrile The title compound was obtained according to the method described for example 12, starting from 2-diethylaminoethylchloride hydrochloride (32.7 mg) and the product of example 8e (100 mg). The residue was purified by preparative HPLC (0→100% acetonitrile, 0.1% TFA). Yield: 62.9 mg (as TFA salt). MS-ESI: [M+H]$^+$=650.4/652.4; anal. HPLC: Rt=13.35 min (diast 1), Rt=13.70 (diast 2) (method 2).

EXAMPLE 15

2-{3-[2-Bromo-4-(3-cyano-2-methyl-5-oxo-7-propyl-1,4,5,6,7,8-hexahydro-quinolin-4-yl)-6-ethoxy-phenoxymethyl]-phenoxy}-N,N-dimethyl-acetamide The title compound was obtained according to the method described for example 12, starting from 2-chloro-N,N-dimethylacetamide (19.6 µl) and the product of example 8e (100 mg). The residue was purified by preparative HPLC (0→100% acetonitrile).

Yield: 53.8 mg. MS-ESI: [M+H]$^+$=636.4/638.4; anal. HPLC: Rt=20.44 min (diast1), Rt=20.77 min (diast2) (method 2). Diast. ratio: 5:1

EXAMPLE 16

4-{3-Bromo-5-ethoxy-4-[3-(2-methoxy-ethoxy)-benzyloxy]-phenyl}-2-methyl-5-oxo-7-propyl-1,4,5,6,7,8-hexahydro-quinoline-3-carbonitrile A mixture of the product of example 8e (100 mg), 2-methoxyethanol (29 µl), diethylazodicarboxylate (57 µl) and triphenylphosphine polymer bound (122 mg) in dichloromethane (6 ml) was stirred under a nitrogen atmosphere for 54 h. The reaction mixture was filtered and concentrated in vacuo. The residue was purified by preparative HPLC (50→100% acetonitrile). Yield: 15 mg. MS-ESI: [M+H]$^+$=609.2/611.2; anal. HPLC: Rt=7.66 min (method 3).

EXAMPLE 17

4-{3-Bromo-5-ethoxy-4-[3-(2-morpholin-4-yl-2-oxo-ethoxy)-benzyloxy]-phenyl}-2-methyl-5-oxo-7-propyl-1,4,5,6,7,8-hexahydro-quinoline-3-carbonitrile (a). {3-[2-Bromo-4-(3-cyano-2-methyl-5-oxo-7-propyl-1,4,5,6,7,8-hexahydro-quinolin-4-yl)-6-ethoxy-phenoxymethyl]-phenoxy}-acetic acid A mixture of the compound of example 8f (620 mg) in dichloromethane (45 ml) and trifluoracetic acid (5 ml) was stirred for 4 h. The reaction mixture was diluted with dichloromethane, washed with water and brine. The organic layer was separated, dried (MgSO$_4$), filtered and concentrated in vacuo. Yield: 553 mg. MS-ESI: [M+H]$^+$=609.2/611.2

(b). 4-{3-Bromo-5-ethoxy-4-[3-(2-morpholin-4-yl-2-oxo-ethoxy)-benzyloxy]-phenyl}-2-methyl-5-oxo-7-propyl-1,4,5,6,7,8-hexahydro-quinoline-3-carbonitrile Coupling of the compound described in example 17a (79 mg) with morpholine (34 µl) and TBTU (62 mg) was performed according to the method described in example 6d.

Yield: 50.5 mg. MS-ESI: [M+H]$^+$=678.4/680.4; anal. HPLC: Rt=16.29 min (diast1), Rt=16.65 (diast2) (method 1). Diast. ratio: 5:1

EXAMPLE 18

2-{3-[2-Bromo-4-(3-cyano-2-methyl-5-oxo-7-propyl-1,4,5,6,7,8-hexahydro-quinolin-4-yl)-6-ethoxy-phenoxymethyl]-phenoxy}-N-thiophen-2-ylmethyl-acetamide Coupling of the compound described in example 17a (75 mg) with 2-thiophenemethylamine (38 µl) and TBTU (59 mg) was performed according to the method described in example 6d. The residue was purified by preparative HPLC (40→100% acetonitrile). Yield: 45.7 mg. MS-ESI: [M+H]$^+$=704.4/706.4; anal. HPLC: Rt=6.96 min (method 3).

EXAMPLE 19

N-{2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-2-pyrrolidin-1-yl-acetamide (a). 3-Bromo-5-ethoxy-4-(2-nitro-benzyloxy)-benzaldehyde Alkylation of 3-bromo-5-ethoxy-4-hydroxybenzaldehyde (5 g) with 2-nitrobenzylbromide (4.85 g) was performed according to the method described in example 1a. Yield: 7.88 g. MS-ESI: [M+H]$^+$=380/382

(b). 4-[3-Bromo-5-ethoxy-4-(2-nitro-benzyloxy)-phenyl]-2-methyl-5-oxo-7-propyl-1,4,5,6,7,8-hexahydro-quinoline-3-carbonitrile The title compound was prepared according to the method described in example 1b starting from the product of example 19a (7.88 g), 3-aminocrotonitrile (1.7 g) and 5-propylcyclohexane-1,3-dione (3.2 g). Yield: 8.54 g. MS-ESI: [M+H]$^+$=580.2/582.2

(c). 4-[4-(2-Amino-benzyloxy)-3-bromo-5-ethoxy-phenyl]-2-methyl-5-oxo-7-propyl-1,4,5,6,7,8-hexahydro-quinoline-3-carbonitrile At 0° C. Zinc dust (9.01 g) was added portion wise to a solution of the product of example 19c (6.9 g) and acetic acid (5.9 ml) in THF (150 ml). After stirring at 0° C. for 1 h and at room temperature for 2 h, the reaction mixture was filtered, diluted with dichloromethane and washed with sat. NaHCO$_3$ and brine. The organic layer was separated, dried (MgSO$_4$), filtered and concentrated in vacuo. Yield: 3.66 g. MS-ESI: [M+H]$^+$=550.2/552.2

(d). 2-Bromo-N-{2-[2-bromo-4-(3-cyano-2-methyl-5-oxo-7-propyl-1,4,5,6,7,8-hexahydro-quinolin-4-yl)-6-ethoxy-phenoxymethyl]-phenyl}-acetamide Reaction of bromoacetyl chloride (0.546 ml) with the product of example 19c (1.2 g) was preformed according to the method described for example 3a. Yield: 1.36 g. MS-ESI: [M+H]$^+$=626.2/628.2

(e). N-{2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-2-pyrrolidin-1-yl-acetamide A mixture of the product of example 19d (136 mg) and pyrrolidine (181 µl) in THF (5 ml) was stirred for 54 h. The reaction mixture was diluted with ethyl acetate and washed with water, sat. NaHCO$_3$ and brine. The organic layer was dried (MgSO$_4$), filtered and concentrated in vacuo. The residue was purified by preparative HPLC (10→100% acetonitrile, 0.1% TFA). Yield: 51.8 mg (as TFA salt). MS-ESI: [M+H]$^+$=661.4/663.4; anal. HPLC: Rt=13.58 (method 2)

EXAMPLE 20

N-{2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-2-[(2-dimethylamino-ethyl)-methyl-amino]-acetamide The title compound was prepared according to the method described in example 19e starting from the product of example 19d (136 mg) and N,N,N'-trimethyl-ethane-1,2-diamine (277 µl). Yield: 41 mg (as TFA salt). MS-ESI: [M+H]$^+$= 690.4/692.4; anal. HPLC: Rt=12.14 min (diast 1), Rt=12.46 (diast 2) (method 2). Diast. ratio: 7:1

EXAMPLE 21

4-[3-Bromo-5-ethoxy-4-(2-methylsulfanyl-pyrimidin-4-ylmethoxy)-phenyl]-2-methyl-5-oxo-7-propyl-1,4,5,6,7,8-hexahydro-quinoline-3-carbonitrile (a). 5-Bromo-2-methylsulfanyl-pyrimidine-4-carboxylic acid At 5° C. triethylamine (16.9 ml) was added dropwise to a solution of mucobromic acid (10.31 g) and 2-methyl-isothiourea (11.13 g) in water (200 ml). After stirring at 5° C. for 3 h, the reaction mixture was allowed to warm up (room temperature) and stirring was continued for another 54 h. The reaction mixture was acidified with conc. HCl (33%). The title product was obtained by filtration. Yield: 4.1 g. MS-ESI: [M+H]$^+$= 249/251

(b). 2-Methylsulfanyl-pyrimidine-4-carboxylic acid

The product of example 21a (517 mg) in methanol (25 ml) was hydrogenated in a PARR apparatus in the presence of KOH (260 mg) and 10% Pd on BaSO$_4$ (260 mg) for 4 h. The reaction mixture was filtered over decalite and washed with methanol (warm). The filtrate was concentrated to 50% of its volume followed by addition of conc. HCl (33%) to pH 1. The precipitate (KBr) was filtered off and the mother liquor was concentrated in vacuo. The residue was recrystallized from dioxane. Yield: 200 mg. MS-ESI: [M+H]$^+$=170

(c). 2-Methylsulfanyl-pyrimidin-4-yl)-methanol

At 0° C. oxalyl chloride (295 µl) was added to a solution of DMF (91.2 µl) in dichloromethane (2 ml). After stirring at 0° C. for 1 h, the reaction mixture was concentrated in vacuo. The residue was dissolved in acetonitrile (2 ml) and THF (3 ml), followed by portion wise addition of the product of example 21b (200 mg) at 0° C. in a nitrogen atmosphere. After stirring at 0° C. for 15 min, the reaction mixture was cooled (−78° C.) and 2M NaBH$_4$ in DMF (590 µl) was added. After stirring at −20° C. for 3 h, the reaction mixture was quenched with 2N HCl and concentrated in vacuo. The residue was dissolved in water and the remaining solution was adjusted to pH 11 with 2N NaOH, followed by extraction with dichloromethane. The organic layer was separated, dried (MgSO$_4$), filtered and concentrated in vacuo. Yield: 180 mg. MS-ESI: [M+H]$^+$=156

(d). 3-Bromo-5-ethoxy-4-(2-methylsulfanyl-pyrimidin-4-ylmethoxy)-benzaldehyde

A mixture of the product of example 21c (180 mg), 3-bromo-5-ethoxy-4-hydroxy benzaldehyde (289 mg), triphenylphosphine polymer bound (393 mg) and diethylazodicarboxylate (186 µl) in dichloromethane (25 ml) was stirred for 18 h. The reaction mixture was filtered off and the filtrate concentrated in vacuo. The residue was chromatographed on silica gel in heptane/ethyl acetate=3/2 (v/v) as eluent. Yield: 98 mg. MS-ESI: [M+H]$^+$=383/385

(e). 4-[3-Bromo-5-ethoxy-4-(2-methylsulfanyl-pyrimidin-4-ylmethoxy)-phenyl]-2-methyl-5-oxo-7-propyl-1,4,5,6,7,8-hexahydro-quinoline-3-carbonitrile The title compound was prepared according to the method described in example 1b starting from the product of example 22d (49 mg), 3-aminocrotonitrile (11 mg) and 5-propylcyclohexane-1,3-dione (20 mg). The residue was purified by preparative HPLC (0→100% acetonitrile, 0.1% TFA). Yield: 24 mg (as TFA salt). MS-ESI: [M+H]$^+$=583.2/585.2; anal. HPLC: Rt=25.06 min (diast1), Rt=25.51 min (diast2) (method 2). Diast. ratio: 4:1

EXAMPLE 22

Furan-2-carboxylic acid {2-[2-bromo-4-(3-cyano-2-methyl-5-oxo-7-propyl-1,4,5,6,7,8-hexahydro-quinolin-4-yl)-6-ethoxy-phenoxymethyl]-phenyl}-amide A mixture of the product of example 19c (100 mg), 2-furoylchloride (36 pJ) and DIPEA (159 µl) in dichloromethane (5 ml) was stirred for 16 h. The reaction mixture was diluted with dichloromethane and washed with sat. NaHCO$_3$. The organic layer was separated, dried (MgSO$_4$), filtered and concentrated in vacuo. The residue was purified by preparative HPLC (20→100% acetonitrile). Yield: 67 mg. MS-ESI: [M+H]$^+$=644.4/646.4; anal. HPLC: Rt=20.19 min (method 1).

EXAMPLE 23

N-{2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-acrylamide Reaction of the product of example 19c (100 mg) with acryloylchloride (29 µl) in the presence of DIPEA (159 µl) was performed according to the method described in example 22. Yield: 51.1 mg. MS-ESI: [M+H]$^+$=604.4/606.4; anal. HPLC: Rt=19.01 min (diast1), Rt=19.42 min (diast2) (method 1). Diast. ratio: 9:1

EXAMPLE 24

Cyclopropanecarboxylic acid {2-[2-bromo-4-(3-cyano-2-methyl-5-oxo-7-propyl-1,4,5,6,7,8-hexahydro-quinolin-4-yl)-6-ethoxy-phenoxymethyl]-phenyl}-amide Reaction of the product of example 19c (100 mg) with cyclopropanecarbonylchloride (33 µl) in the presence of DIPEA (159 µl) was performed according to the method described in example 22. Yield: 52.1 mg. MS-ESI: [M+H]$^+$= 618.2/620.2; anal. HPLC: Rt=20.30 min (diast1), Rt=20.71 min (diast2) (method 1). Diast. ratio: 7:1

EXAMPLE 25

2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-carbamic acid methyl ester Reaction of the product of example 19c (100 mg) with methylchloroformate (28 µl) in the presence of DIPEA (159 µl) was performed according to the method described in example 22. Yield: 65.9 mg. MS-ESI: [M+H]$^+$=608.2/610.2; anal. HPLC: Rt=21.37 min (diast1), Rt=21.87 min (diast2) (method 1). Diast. ratio: 11:1

EXAMPLE 26

2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-carbamic acid isobutyl ester Reaction of the product of example 19c (100 mg) with isobutyl chloroformate (47 µl) in the presence of DIPEA (159 µl) was performed according to the method described in example 22. Yield: 70 mg. MS-ESI: [M+H]$^+$=650.4/652.4; anal. HPLC: Rt=26.84 min (diast), Rt=27.26 min (diast2) (method 1). Diast. ratio: 7:1

EXAMPLE 27

2-[2-Bromo-4-(3-cyano-2-methyl-5-oxo-7-propyl-1,4,5,6,7,8-hexahydro-quinolin-4-yl)-6-ethoxy-phenoxymethyl]-furan-3-carboxylic acid methyl ester (a). 2-(2-Bromo-6-ethoxy-4-formyl-phenoxymethyl)-furan-3-carboxylic acid methyl ester Alkylation of 3-bromo-5-ethoxy-4-hydroxy benzaldehyde (123 mg) with 2-bromomethyl-furan-3-carboxylic acid methyl ester (109 mg) was performed according to the method described in example 1a. Yield: 191 mg. MS-ESI: [M+H]$^+$=383/385

(b). 2-[2-Bromo-4-(3-cyano-2-methyl-5-oxo-7-propyl-1,4,5,6,7,8-hexahydro-quinolin-4-yl)-6-ethoxy-phenoxymethyl]-furan-3-carboxylic acid methyl ester The title compound was prepared according to the method described in example 1b starting from the product of example 27a (191 mg), 3-aminocrotonitrile (41 mg) and 5-propylcyclohexane-1,3-dione (77 mg). The residue was purified by preparative HPLC (10→90% acetonitrile). Yield: 168 mg. MS-ESI: [M+H]$^+$=583/585; anal. HPLC: Rt=23.06 min (diast1), Rt=23.43 min (diast2) (method 2). Diast. ratio: 4:1

EXAMPLE 28

Propane-1-sulfonic acid {2-[2-bromo-4-(3-cyano-2-methyl-5-oxo-7-propyl-1,4,5,6,7,8-hexahydro-quinolin-4-yl)-6-ethoxy-phenoxymethyl]-phenyl}-amide Propane-1-sulfonyl chloride (31 µl) and pyridine (44 µl) were added to a solution of the product of example 19c (100 mg) in dichloromethane (3 ml). After stirring for 18 h, the reaction mixture was diluted with dichloromethane and washed with sat. NaHCO$_3$. The organic layer was separated, dried (MgSO$_4$), filtered and concentrated in vacuo. The residue was purified by preparative HPLC (20→100% acetonitrile). Yield: 52.7 mg. MS-ESI: [M+H]$^+$=656.4/658.4; anal. HPLC: Rt=22.36 min (diast1), Rt=22.72 min (diast2) (method 1). Diast. ratio: 7:1

EXAMPLE 29

4-[2-Bromo-4-(3-cyano-2-methyl-5-oxo-7-propyl-1,4,5,6,7,8-hexahydro-quinolin-4-yl)-6-ethoxy-phenoxymethyl]-N-(2-methoxy-ethyl)-benzamide (a). 4-(2-Bromo-6-ethoxy-4-formyl-phenoxymethyl)-benzoic acid methyl ester Alkylation of 3-bromo-5-ethoxy-4-hydroxy benzaldehyde (4 g) with 4-bromomethylbenzoic acid methyl ester (3.73 g) was performed according to the method described in example 1a. Yield: 6.4 g. MS-ESI: [M+H]$^+$=393/395

(b). 4-[2-Bromo-4-(3-cyano-2-methyl-5-oxo-7-propyl-1,4,5,6,7,8-hexahydro-quinolin-4-yl)-6-ethoxy-phenoxymethyl]-benzoic acid methyl ester The title compound was prepared according to the method described in example 1b starting from the product of example 29a (6.4 g), 3-aminocrotonitrile (1.34 g) and 5-propylcyclohexane-1,3-dione (2.51 g). Yield: 6.74 g. MS-ESI: [M+H]$^+$=593/595

(c). 4-[2-Bromo-4-(3-cyano-2-methyl-5-oxo-7-propyl-1,4,5,6,7,8-hexahydro-quinolin-4-yl)-6-ethoxy-phenoxymethyl]-benzoic acid A mixture of the product of example 29b (6.5 g) and 2N NaOH (11.3 ml) in dioxane (400 ml) was stirred at 50° C. for 18 h. The reaction mixture was poured in water and in addition 4N HCl was added until pH 2, followed by extraction with ethyl acetate. The organic layer was washed with brine, dried (MgSO$_4$), filtered and concentrated in vacuo. Yield: 6.4 g. MS-ESI: [M+H]$^+$=579/581

(d). 4-[2-Bromo-4-(3-cyano-2-methyl-5-oxo-7-propyl-1,4,5,6,7,8-hexahydro-quinolin-4-yl)-6-ethoxy-phenoxymethyl]-N-(2-methoxy-ethyl)-benzamide Coupling of the compound described in example 29c (100 mg) with 2-methoxy-ethylamine (44 µl) and TBTU (82 mg) was performed according to the method described in example 6d. Yield: 70 mg. MS-ESI: [M+H]$^+$=636.4/638.4; anal. HPLC: Rt=19.25 min (diast1), 19.55 min (diast2) (method 2). Diast. ratio: 4:1 (HPLC)

EXAMPLE 30

4-{3-Bromo-5-ethoxy-4-[3-(isobutylamino-methyl)-benzyloxy]-phenyl}-2-methyl-5-oxo-7-propyl-1,4,5,6,7,8-hexahydro-quinoline-3-carbonitrile (a). 4-(3-Bromo-5-ethoxy-4-hydroxy-phenyl)-2-methyl-5-oxo-7-propyl-1,4,5,6,7,8-hexahydro-quinoline-3-carbonitrile The title compound was prepared according to the method described in example 1b starting from 3-bromo-5-ethoxy-4-hydroxy-benzaldehyde (6 g), 3-aminocrotonitrile (2.01 g) and 5-propylcyclohexane-1,3-dione (3.8 g). The reaction mixture was cooled (0° C.) and the title compound was filtered off and washed with ethanol (cold). Yield: 6.3 g. MS-ESI: [M+H]$^+$=445/447

(b). 4-[3-Bromo-4-(3-bromomethyl-benzyloxy)-5-ethoxy-phenyl]-2-methyl-5-oxo-7-propyl-1,4,5,6,7,8-hexahydro-quinoline-3-carbonitrile A mixture of the product of example 30a (1.96 g), α,α,-dibromo-m-xylene (9.31 g) and K$_2$CO$_3$ (1.22 g) in DMF (100 ml) was stirred at 60° C. under a nitrogen atmosphere for 2 h. The reaction mixture was diluted with ethyl acetate and washed with water, sat. NaHCO$_3$ and brine. The organic layer was dried (MgSO$_4$), filtered and concentrated in vacuo. The residue was chromatographed on silica gel in heptane/ethyl acetate=1/2 (v/v). Yield: 2.52 g MS-ESI: [M+H]$^+$=627.4/

629.4/631.4; anal. HPLC: Rt=17.71 min (diast1), 18.07 min (diast2) (method 6). Diast. ratio: 4:1

(c). 4-{3-Bromo-5-ethoxy-4-[3-(isobutylamino-methyl)-benzyloxy]-phenyl}-2-methyl-5-oxo-7-propyl-1,4,5,6,7,8-hexahydro-quinoline-3-carbonitrile A mixture of the product of example 30b (100 mg) and iso-butylamine (79 µl) in acetonitrile (5 ml) was stirred for 18 h. The reaction mixture was concentrated in vacuo; the residue was dissolved in dichloromethane and washed with sat. NaHCO$_3$. The organic layer was separated, dried (MgSO$_4$), filtered and concentrated in vacuo. The residue was purified by preparative HPLC (0→100% acetonitrile, 0.1% TFA).
Yield: 76 mg (as TFA salt). MS-ESI: [M+H]$^+$=620.4/622.4; anal. HPLC: Rt=13.56 min (diast1), Rt=13.85 min (diast2) (method 2). Diast. ratio: 3:1

EXAMPLE 31

4-[3-Bromo-5-ethoxy-4-(3-{[(pyridin-4-ylmethyl)-amino]-methyl}-benzyloxy)phenyl]-2-methyl-5-oxo-7-propyl-1,4,5,6,7,8-hexahydro-quinoline-3-carbonitrile The title compound was prepared according to the method described in example 30c starting from the product of example 30b (100 mg) and 4-(aminomethyl)pyridine (81 µl) in acetonitrile (5 ml). Yield: 41 mg (as TFA salt). MS-ESI: [M+H]$^+$=655.2/657.2; anal. HPLC: Rt=8.08 min (method 2). Diast. ratio: 3:1

EXAMPLE 32

4-[4-(3-Aminomethyl-benzyloxy)-3-bromo-5-ethoxy-phenyl]-2-methyl-5-oxo-7-propyl-1,4,5,6,7,8-hexahydro-quinoline-3-carbonitrile (a). 4-[4-(3-Azidomethyl-benzyloxy)-3-bromo-5-ethoxy-phenyl]-2-methyl-5-oxo-7-propyl-1,4,5,6,7,8-hexahydro-quinoline-3-carbonitrile A mixture of the product of example 30b (250 mg) and NaN$_3$ (78 mg) in DMF (10 ml) was stirred for 2 h. The reaction mixture was poured in water and the precipitate was filtered off, washed with water and dried in vacuo (50° C.). Yield: 197 mg. MS-ESI: [M+H]$^+$=590.4/592.4; anal. HPLC: Rt=23.72 min (diast1), Ry=24.12 min (diast2) (method 1). Diast. ratio: 3.5:1

(b). 4-[4-(3-Aminomethyl-benzyloxy)-3-bromo-5-ethoxy-phenyl]-2-methyl-5-oxo-7-propyl-1,4,5,6,7,8-hexahydro-quinoline-3-carbonitrile A mixture of the product of example 32a (133 mg), triphenylphosphine polymer bound (150 mg) and 10 drops of water in THF/dichloromethane=2:1 (v/v) was stirred at 40° C. for 18 h. The reaction mixture was filtered and concentrated in vacuo. The residue was purified by preparative HPLC (0→100% acetonitrile, 0.1% TFA). Yield: 197 mg (as TFA salt). MS-ESI: [M+H]$^+$=564.2/566.2; anal. HPLC: Rt=10.31 min (diast1), Rt=10.58 min (diast2) (method 2). Diast. ratio: 3:1

EXAMPLE 33

4-[3-Bromo-5-ethoxy-4-(3-hydroxymethyl-benzyloxy)-phenyl]-2-methyl-5-oxo-7-propyl-1,4,5,6,7,8-hexahydro-quinoline-3-carbonitrile A mixture of the product of example 30b (100 mg) and CaCO$_3$ (80 mg) in dioxane/water=1/1 (v/v) was stirred at 100° C. for 18 h. The reaction mixture was diluted with dichloromethane followed by addition of 2N HCl. The organic layer was separated, washed with sat. NaHCO$_3$, dried (MgSO$_4$), filtered and concentrated in vacuo. The residue was purified by preparative HPLC (20→100% acetonitrile). Yield: 44 mg. MS-ESI: [M+H]$^+$=565.2/567.2; anal. HPLC: Rt=15.96 min (diast1), Rt=16.33 min (diast2) (method 1). Diast. ratio: 4:1

EXAMPLE 34

1-{2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-3-methyl-urea A mixture of the compound of example 19c and 4-nitrophenyl chloroformate (55 mg) in dichloromethane (4 ml) was stirred for 2 h. Methylamine (2.7 ml, 2M in THF) was added and stirring was continued for another 3 h. The reaction mixture was diluted with dichloromethane and washed with sat. NaHCO$_3$. The organic layer was separated, dried (MgSO$_4$), filtered and concentrated in vacuo. The residue was purified by preparative HPLC (20→100% acetonitrile). Yield: 54 mg. MS-ESI: [M+H]$^+$=607.2/609.2; anal. HPLC: Rt=15.88 min (diast1), Rt=16.18 min (diast2) (method 1). Diast. ratio: 8:1

EXAMPLE 35

Piperazine-1-carboxylic acid {2-[2-bromo-4-(3-cyano-2-methyl-5-oxo-7-propyl-1,4,5,6,7,8-hexahydro-quinolin-4-yl)-6-ethoxy-phenoxymethyl]-phenyl}-amide The title compound was prepared according to the method described in example 34 starting from the product of example 19c (150 mg), 4-nitrophenyl chloroformate (55 mg) and piperazine (469 mg). The residue was purified by preparative HPLC (0→100% acetonitrile, 0.1% TFA). Yield: 69 mg (as TFA salt). MS-ESI: [M+H]$^+$=662.2/664.2; anal. HPLC: Rt=11.70 min (diast1), Rt=12.04 min (diast2) (method 1). Diast. ratio: 5:1

EXAMPLE 36

N-{3-[2-Bromo-4-(3-cyano-2-methyl-5-oxo-7-propyl-1,4,5,6,7,8-hexahydro-quinolin-4-yl)-6-ethoxy-phenoxymethyl]-benzyl}-3,3-dimethyl-butyramide Acylation of the product of example 32b (100 mg) with tert-butylacetyl chloride (27 µl) was performed according to the method described in example 1d. Yield: 33.5 mg. MS-ESI: [M+H]$^+$=662.4/664.4; anal. HPLC: Rt=21.26 min (diast1), Rt=21.54 min (diast2) (method 1).

EXAMPLE 37

{3-[2-Bromo-4-(3-cyano-2-methyl-5-oxo-7-propyl-1,4,5,6,7,8-hexahydro-quinolin-4-yl)-6-ethoxy-phenoxymethyl]-benzyl}-carbamic acid ethyl ester Reaction of the product of example 32b (100 mg) with ethylchloroformate (19 µl) in the presence of DIPEA (93 µl) was performed according to the method described in example 22. Yield: 37 mg. MS-ESI: [M+H]$^+$=636.2/638.2; anal. HPLC: Rt=19.81 min (diast1), Rt=20.14 min (diast2) (method 1). Diast. ratio: 4.5:1

EXAMPLE 38

{3-[2-Bromo-4-(3-cyano-2-methyl-5-oxo-7-propyl-1,4,5,6,7,8-hexahydro-quinolin-4-yl)-6-ethoxy-phenoxymethyl]-pyridin-2-yl}-carbamic acid methyl ester (a). 4-(2-Amino-pyridin-3-ylmethoxy)-3-bromo-5-ethoxy-benzaldehyde Mitsunobu reaction of 3-bromo-5-ethoxy-4-hydroxy benzaldehyde (490 mg) with (2-amino-pyridin-3-yl)-methanol (250 mg) was preformed according to the method described for example 21d. The residue was chromatographed on silica gel in dichloromethane/methanol=99/1 (v/v) as eluent. Yield: 500 mg. MS-ESI: [M+H]$^+$=351/353.

(b). 4-[4-(2-Amino-pyridin-3-ylmethoxy)-3-bromo-5-ethoxy-phenyl]-2-methyl-5-oxo-7-propyl-1,4,5,6,7,8-hexahydro-quinoline-3-carbonitrile The title compound was prepared according to the method described in example 1b starting from the product of example 38a (500 mg), 3-aminocrotonitrile (116 mg) and 5-propylcyclohexane-1,3-dione (218 mg). Yield: 290 mg. MS-ESI: [M+H]$^+$=551/553

(c). {3-[2-Bromo-4-(3-cyano-2-methyl-5-oxo-7-propyl-1,4,5,6,7,8-hexahydro-quinolin-4-yl)-6-ethoxy-phenoxymethyl]-pyridin-2-yl}-carbamic acid methyl ester Reaction of the product of example 38b (50 mg) with methylchloroformate (8 µl) in the presence of DIPEA (47 µl) was performed according to the method described in example 22. The residue was purified by preparative HPLC (10→90% acetonitrile).
Yield: 17 mg. MS-ESI: [M+H]$^+$=609/611; anal. HPLC: Rt=13.82 min (diast1), Rt=14.08 min (diast2) (method 5). Diast. ratio: 7:2

EXAMPLE 39

4-(3-Bromo-5-ethoxy-4-{3-[(1H-imidazol-4-ylmethyl)-amino]-benzyloxy}-phenyl)-2-methyl-5-oxo-7-propyl-1,4,5,6,7,8-hexahydro-quinoline-3-carbonitrile A mixture of the product of example 1c (100 mg), 1H-imidazol-4-carbaldehyde (21 mg), NaCNBH$_4$ (25 mg) and acetic acid (114 µl) in methanol (3 ml) was stirred for 18 h. The reaction mixture was diluted with ethyl acetate, washed with sat. NaHCO$_3$ and brine. The organic layer was separated, dried (MgSO$_4$), filtered and concentrated in vacuo. The residue was purified by preparative HPLC (40→100% acetonitrile).
Yield: 13 mg. MS-ESI: [M+H]$^+$=550.2/552.2; anal. HPLC: Rt=7.27 min (method 1). Diast. ratio: 4:1.

EXAMPLE 40

4-[2-Bromo-4-(3-cyano-2-methyl-5-oxo-7-propyl-1,4,5,6,7,8-hexahydro-quinolin-4-yl)-6-ethoxy-phenoxymethyl]-N-(2-methoxy-ethyl)-benzenesulfonamide (a). 4-bromomethyl-benzenesulfonyl chloride At 20° C. benzoyl peroxide (600 mg) was added to a suspension of 4-methyl-benzenesulfonyl chloride (9.5 g) and N-bromosuccinimide (8.9 g) in 1,2-dichloropropane (60 ml). The reaction mixture was stirred at 80° C. for 2 h. The reaction mixture was concentrated and the title compound was obtained as a white solid after recrystallization from heptane. Yield: 2.26 g.

(b). 4-Bromomethyl-N-(2-methoxy-ethyl)-benzenesulfonamide

At 20° C. triethylamine (61 mg) was added to a solution of the product of example 40a (135 mg) in diethyl ether (2 ml). After 5 minutes, 2-methoxy-ethylamine (37 mg) was added. The reaction mixture was stirred at 20° C. for 3 h and concentrated in vacuo. The residue was dissolved in dichloromethane (20 ml) and washed several times with sat. NaHCO$_3$. The organic phase was separated, dried (MgSO$_4$) and concentrated in vacuo. The title product was obtained as brown oil. Yield: 120 mg. MS-ESI: [M+H]$^+$=308/310.

(c). 4-[2-Bromo-4-(3-cyano-2-methyl-5-oxo-7-propyl-1,4,5,6,7,8-hexahydro-quinolin-4-yl)-6-ethoxy-phenoxymethyl]-N-(2-methoxy-ethyl)-benzenesulfonamide At 20° C. a solution of the product of example 40b (120 mg) in DMF (3 ml) was added to a suspension of the product of 30a (222 mg), K$_2$CO$_3$ (200 mg) and KI (10 mg) in DMF (7 ml). The reaction mixture was stirred at 20° C. for 16 h and poured into 10 ml sat. NaHCO$_3$ and extracted with ethyl acetate. The organic layer was concentrated, dissolved in dichloromethane and washed with water, dried (MgSO$_4$) and concentrated in vacuo. The title product was obtained via preparative HPLC (0→90% CH$_3$CN, 0.1% TFA). Yield: 22 mg. MS-ESI: [M+H]$^+$=672/674; anal. HPLC: Rt=21.31 min (method 2). Diast. ratio: 4:1

EXAMPLE 41

4-[2-Bromo-4-(3-cyano-2-methyl-5-oxo-7-propyl-1,4,5,6,7,8-hexahydro-quinolin-4-yl)-6-ethoxy-phenoxymethyl]-N,N-diethyl-benzenesulfonamide (a). 4-Bromomethyl-N,N-diethyl-benzenesulfonamide The title compound was obtained analogously to example 40b, starting from diethylamine (37 mg) and the product of example 40a (135 mg). Yield: 122 mg. R$_f$ (heptane/ethyl acetate (1/1, v/v))=0.45. MS-ESI: [M+H]$^+$=306/308.

(b). 4-[2-Bromo-4-(3-cyano-2-methyl-5-oxo-7-propyl-1,4,5,6,7,8-hexahydro-quinolin-4-yl)-6-ethoxy-phenoxymethyl]-N,N-diethyl-benzenesulfonamide The title compound was obtained analogously to example 40c, starting from product of example 41a (122 mg) and the product of example 30a (222 mg). Yield: 79 mg. MS-ESI: [M+H]$^+$=670/672; anal. HPLC: Rt=26.63 min (diast1), 26.93 min (diast2) (method 2). Diast. ratio: 4:1

EXAMPLE 42

N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-methanesulfonamide Sulfonylation of the product of example 1c (100 mg) with methanesulfonyl chloride (15 μl) was preformed according to the method described in example 28. Yield: 46 mg. MS-ESI: [M+H]$^+$=628/630; anal. HPLC: Rt=20.76 min (diast1), Rt=21.01 min (diast2) (method 2). Diast. ratio: 4:1

EXAMPLE 43

Thiophene-2-sulfonic acid {3-[2-bromo-4-(3-cyano-2-methyl-5-oxo-7-propyl-1,4,5,6,7,8-hexahydro-quinolin-4-yl)-6-ethoxy-phenoxymethyl]-phenyl}-amide Sulfonylation of the product of example 1c (100 mg) with thiophene-2-sulfonyl chloride (36 μl) was preformed according to the method described in example 28.

Yield: 70 mg. MS-ESI: [M+H]$^+$=696.2/698.2; anal. HPLC: Rt=23.75 min (method 2). Diast. ratio: 4:1

EXAMPLE 44

4-[2-Bromo-4-(3-cyano-2-methyl-5-oxo-7-propyl-1,4,5,6,7,8-hexahydro-quinolin-4-yl)-6-ethoxy-phenoxymethyl]-benzenesulfonic acid isopropyl ester (a). Toluene-4-sulfonic acid isopropyl ester At 0° C., 4-methyl-benzenesulfonyl chloride (3.8 g) was added to a solution of 2-propanol (6.12 ml) in pyridine (6.6 ml). The reaction mixture was stirred at 0° C. for 2 h and then at 20° C. for 16 h. The reaction mixture was poured into water (150 ml) and extracted with dichloromethane. The combined organic phases were washed with 3M aqueous HCl and sat. NaHCO$_3$. After drying (MgSO$_4$) and concentrating in vacuo, the title product was obtained as a pale yellow oil. Yield: 2.89 g. MS-ESI: [M+H]$^+$=215.

(b). 4-Bromomethyl-benzenesulfonic acid isopropyl ester

At 20° C. benzoyl peroxide (48 mg) was added to a solution of the product of example 44a (956 mg) and N-bromosuccinimide (712 mg) in deuterochloroform (5 ml). The reaction mixture was stirred at 80° C. for 3 h. The reaction mixture was poured into 20 ml of sat. NaHCO$_3$ and extracted several times with dichloromethane. The combined organic layers were dried (MgSO$_4$) and concentrated in vacuo. The title product was obtained as pale yellow oil. Yield: 1.06 g.

(c). 4-[2-Bromo-4-(3-cyano-2-methyl-5-oxo-7-propyl-1,4,5,6,7,8-hexahydro-quinolin-4-yl)-6-ethoxy-phenoxymethyl]-benzenesulfonic acid isopropyl ester The title compound was obtained analogously to example 40c, starting from the product of example 44b (293 mg) and product of example 30a (400 mg). Yield: 38 mg. MS-ESI: [M+H]$^+$=657/659; anal. HPLC: Rt=22.64 min (diast1), Rt=22.64 min (diast 2) (method 2). Diast. ratio: 10:1

EXAMPLE 45

3-[2-Bromo-4-(3-cyano-2-methyl-5-oxo-7-propyl-1,4,5,6,7,8-hexahydro-quinolin-4-yl)-6-ethoxy-phenoxymethyl]-N-methyl-benzenesulfonamide (a). 3-bromomethyl-benzenesulfonyl chloride The title compound was obtained analogously to example 40a, starting from 3-methyl-benzenesulfonyl chloride (8.5 g), N-bromosuccinimide (8.9 g) and benzoylperoxide (600 mg) in deuterochloroform (20 ml) as solvent. Yield: 3.1 g.

(b). 3-Bromomethyl-N-methyl-benzenesulfonamide

The title compound was obtained analogously to example 40b, starting from methylamine (105 mg) and the product of example 45a (269 mg) and the product of example 30a (200 mg). Yield: 220 mg. MS-ESI: [M-Me]$^-$=250/252

(c). 3-[2-Bromo-4-(3-cyano-2-methyl-5-oxo-7-propyl-1,4,5,6,7,8-hexahydro-quinolin-4-yl)-6-ethoxy-phenoxymethyl]-N-methyl-benzenesulfonamide The title compound was obtained analogously to example 40c, starting from the product of example 45b (220 mg) and the product of example 30a (200 mg). Yield: 17 mg. MS-ESI: [M+H]$^+$=628/630; anal. HPLC: Rt=20.7 min (diast1), Rt=20.7 min (diast2) (method 2). Diast. ratio: 10:1

EXAMPLE 46

4-{3-Bromo-5-ethoxy-4-[3-(morpholine-4-sulfonyl)-benzyloxy]-phenyl}-2-methyl-5-oxo-7-propyl-1,4,5,6,7,8-hexahydro-quinoline-3-carbonitrile (a). 4-(3-Bromomethyl-benzenesulfonyl)-morpholine The title compound was obtained analogously to example 40b, starting from morpholine (137 μl), and the product of example 45a (269 mg). Yield: 280 mg.

(b). 4-{3-Bromo-5-ethoxy-4-[3-(morpholine-4-sulfonyl)-benzyloxy]-phenyl}-2-methyl-5-oxo-7-propyl-1,4,5,6,7,8-hexahydro-quinoline-3-carbonitrile The title compound was obtained analogously to example 40c, starting from the product of example 46a (280 mg) and the product of example 30a (200 mg). Yield: 63 mg. MS-ESI: [M+H]$^+$=684/686; anal. HPLC: Rt=22.84 min (method 2). Diast. ratio: 10:1

EXAMPLE 47

4-[2-Bromo-4-(3-cyano-2-methyl-5-oxo-7-propyl-1,4,5,6,7,8-hexahydro-quinolin-4-yl)-6-ethoxy-phenoxymethyl]-benzenesulfonic acid At 20° C. a solution of KI (91 mg) in water (0.5 ml) was added to a solution of the product of example 44c (37 mg) in acetone (0.5 ml). The reaction mixture was stirred at 60° C. for 16 h and poured into water (15 ml). After evaporation of acetone, the reaction mixture was extracted several times with dichloromethane. The organic phases were combined dried (MgSO$_4$) and concentrated. The title product was obtained via preparative HPLC (0→90% CH$_3$CN, 1% TFA). Yield: 7 mg. MS-ESI: [M+H]$^+$=617/615; anal. HPLC: Rt=14.31 min (diast1), Rt=14.65 min (diast2) (method 2). Diast. ratio: 6:4 (HPLC)

EXAMPLE 48

N-{4-[2-Bromo-4-(3-cyano-2-methyl-5-oxo-7-propyl-1,4,5,6,7,8-hexahydro-quinolin-4-yl)-6-ethoxy-phenoxymethyl]-phenyl}-methanesulfonamide (a). (4-Hydroxymethyl-phenyl)-carbamic acid 9H-fluoren-9-ylmethyl ester A mixture of (4-amino-phenyl)-methanol (500 mg), Fmoc-Cl (1.2 g) and pyridine (1 ml) in THF (15 ml) was stirred for 1 h. The reaction mixture was diluted with ethyl acetate and washed with water. The organic layer was separated, dried (MgSO$_4$), filtered and concentrated in vacuo. The residue was recrystallized from dichloromethane. Yield: 470 mg. MS-ESI: [M+H]$^+$=346.

(b). (4-Chloromethyl-phenyl)-carbamic acid 9H-fluoren-9-ylmethyl ester

Thionyl chloride (1.03 ml) in dichloromethane (5 ml) was added dropwise to a solution of the product of example 48a (460 mg) in dichloromethane (10 ml). After stirring for 2 h, the reaction mixture was concentrated in vacuo. Yield: 476 mg. Rf=0.75 (heptane/ethyl acetate=1/2 (v/v)

(c). {4-[2-Bromo-4-(3-cyano-2-methyl-5-oxo-7-propyl-1,4,5,6,7,8-hexahydro-quinolin-4-yl)-6-ethoxy-phenoxymethyl]-phenyl}-carbamic acid 9H-fluoren-9-ylmethyl ester A mixture of the product of example 48b (100 mg), the product of example 30a (122 mg) and K$_2$CO$_3$ (114 mg) in DMF (5 ml) was stirred for 4 h. The reaction mixture was diluted with ethyl acetate and washed with water and brine. The organic layer was separated, dried (MgSO$_4$), filtered and concentrated in vacuo. Yield: 233 mg MS-ESI: [M+H]$^+$=772.4/774.4

(d). 4-[4-(4-Amino-benzyloxy)-3-bromo-5-ethoxy-phenyl]-2-methyl-5-oxo-7-propyl-1,4,5,6,7,8-hexahydro-quinoline-3-carbonitrile Piperidine (335 µl) in dichloromethane (5 ml) was added dropwise to a solution of the product of example 48c (223 mg) in dichloromethane (5 ml). After stirring for 2 h, the reaction mixture was concentrated in vacuo. The residue was chromatographed on silica gel in heptane/ethyl acetate=1/4 (v/v) as eluent. Yield: 55 mg. MS-ESI: [M+H]$^+$=550.2/552.2

(e). N-{4-[2-Bromo-4-(3-cyano-2-methyl-5-oxo-7-propyl-1,4,5,6,7,8-hexahydro-quinolin-4-yl)-6-ethoxy-phenoxymethyl]-phenyl}-methanesulfonamide Methanesulfonyl chloride (8 µl) and pyridine (21 µl) were added to a solution of the product of example 48d (50 mg) in dichloromethane (2 ml). After stirring for 2 h, the reaction mixture was diluted with ethyl acetate and washed with water. The organic layer was separated, dried (MgSO$_4$), filtered and concentrated in vacuo. The residue was purified by preparative HPLC (10→100% acetonitrile). Yield: 11 mg. MS-ESI: [M+H]$^+$=628/630; anal. HPLC: Rt=19.78 min. Diast. ratio: 8:1

EXAMPLE 49

N-{2-[2-Bromo-4-(3-cyano-2-methyl-5-oxo-7-propyl-1,4,5,6,7,8-hexahydro-quinolin-4-yl)-6-methoxy-phenoxymethyl]-phenyl}-methanesulfonamide (a). 4-(3-Bromo-4-hydroxy-5-methoxy-phenyl)-2-methyl-5-oxo-7-propyl-1,4,5,6,7,8-hexahydro-quinoline-3-carbonitrile The title compound was obtained analogously to example 1b, starting from 3-Bromo-4-hydroxy-5-methoxy-benzaldehyde (3.0 g). 3-aminocrotonitrile (1.08 g) and 5-propylcyclohexane-1,3-dione (1.98 g). Yield: 4.8 g. MS-ESI: [M+H]$^+$=431/433.

(b). 4-[3-Bromo-5-methoxy-4-(2-nitro-benzyloxy)-phenyl]-2-methyl-5-oxo-7-propyl-1,4,5,6,7,8-hexahydro-quinoline-3-carbonitrile The title compound was obtained analogously to example 30b, starting from 1-bromomethyl-2-nitro-benzene (200 mg) and the product of example 49a (400 mg).
Yield: 384 mg. MS-ESI: [M+H]$^+$=566/568; anal. HPLC: Rt=24.50 min (diast1), Rt=24.95 min (diast2) (method 2). Diast. ratio: 10:1

(c). 4-[4-(2-Amino-benzyloxy)-3-bromo-5-methoxy-phenyl]-2-methyl-5-oxo-7-propyl-1,4,5,6,7,8-hexahydro-quinoline-3-carbonitrile The title compound was obtained analogously to example 19c, starting from the product of example 49b (300 mg). Yield: 289 mg. MS-ESI: [M+H]$^+$=536/538; anal. HPLC: Rt=17.45 min (diast1), Rt=17.91 min (diast2) (method 2). Diast. ratio: 10:1

(d). N-{2-[2-Bromo-4-(3-cyano-2-methyl-5-oxo-7-propyl-1,4,5,6,7,8-hexahydro-quinolin-4-yl)-6-methoxy-phenoxymethyl]-phenyl}-methanesulfonamide The title compound was obtained analogously to example 28, starting from the product of example 49c (100 mg) and methanesulfonyl chloride (20 µl). Yield: 61 mg. MS-ESI: [M+H]$^+$=614/616; anal. HPLC: Rt=22.20 min (method 2). Diast. ratio: 15:1

EXAMPLE 50

{4-[2-Bromo-4-(3-cyano-2-methyl-5-oxo-7-propyl-1,4,5,6,7,8-hexahydro-quinolin-4-yl)-6-ethoxy-phenoxymethyl]-phenyl}-carbamic acid allyl ester (a). (4-Hydroxymethyl-phenyl)-carbamic acid allyl ester Alloc-Cl (537 g) in dichloromethane (5 ml) was added dropwise to a solution of (4-amino-phenyl)-methanol (500 mg) and pyridine (5 ml) in dichloromethane (5 ml). After stirring for 2 h, the reaction mixture was diluted with dichloromethane and washed with water. The organic layer was separated, dried ($MgSO_4$), filtered and concentrated in vacuo. The title compound (243 mg) was obtained by recrystallization from dichloromethane. The mother liquor was chromatographed on silica gel in heptane/ethyl acetate=1/1 (v/v) as eluent which yielded another 245 mg of the title compound. Yield: 488 mg.

(b). (4-Chloromethyl-phenyl)-carbamic acid allyl ester

The title compound was prepared analogously to example 48b starting from the product of example 50a (480 mg) and thionyl chloride (1.7 ml). The residue was chromatographed on silica gel in heptane/ethyl acetate=1/1 (v/v) as eluent. Yield: 310 mg.

(c). {4-[2-Bromo-4-(3-cyano-2-methyl-5-oxo-7-propyl-1,4,5,6,7,8-hexahydro-quinolin-4-yl)-6-ethoxy-phenoxymethyl]-phenyl}-carbamic acid allyl ester The title compound was prepared analogously to example 48c starting from the product of example 50b (300 mg) and the product of example 30a (593 mg). Yield: 333 mg. MS-ESI: $[M+H]^+$=634.4/636.4; anal. HPLC: Rt=24.99 min (method 2).

EXAMPLE 51

4-[3-Bromo-5-ethoxy-4-(1-methanesulfonyl-1H-pyrrol-2-ylmethoxy)-phenyl]-2-methyl-5-oxo-7-propyl-1,4,5,6,7,8-hexahydro-quinoline-3-carbonitrile (a). 1-Methanesulfonyl-1H-pyrrole-2-carbaldehyde A solution of pyrrole-2-carboxyaldehyde (500 mg) in THF (5 ml) was added to a suspension of NaH (252 mg, 60% dispersion on oil) in THF (15 ml). After stirring for 15 min, a solution of methanesulfonyl chloride (570 μl) in THF (5 ml) was added dropwise. After stirring for 1 h, water (25 ml) was added and the THF was evaporated. The residue was diluted with dichloromethane and washed with water, sat. $NaHCO_3$ and brine. The organic layer was separated, dried ($MgSO_4$), filtered and concentrated in vacuo. The residue was chromatographed on silica gel in heptane/ethyl acetate=1/1 (v/v) as eluent. Yield: 265 mg.

(b). (1-Methanesulfonyl-1H-pyrrol-2-yl)-methanol

At 0° C. $LiBH_4$ (1.15 ml, 2.0M in THF) was added dropwise to a solution of the product of example 51a (265 mg) in diethylether (10 ml). After stirring at 0° C. for 30 min, water (2 ml) and acetic acid (2 ml, 10% in water) were added. The water layer was separated and extracted with dichloromethane. The organic layer was washed with water and brine, separated, dried ($MgSO_4$), filtered and concentrated in vacuo. Yield: 205 mg.

(c). 2-Chloromethyl-1-methanesulfonyl-1H-pyrrole

At 0° C. methanesulfonyl chloride (136 μl) was added dropwise to a solution of the product of example 51b (205 mg) and DIPEA (307 μl) in dichloromethane (6 ml). After stirring for 30 min, the reaction mixture was diluted with dichloromethane (30 ml) and washed with ice water (30 ml), 10% HCl (30 ml) and sat. $NaHCO_3$. The organic layer was separated, dried ($MgSO_4$), filtered and concentrated in vacuo. Yield: 252 mg.

(d). 4-[3-Bromo-5-ethoxy-4-(1-methanesulfonyl-1H-pyrrol-2-ylmethoxy)-phenyl]-2-methyl-5-oxo-7-propyl-1,4,5,6,7,8-hexahydro-quinoline-3-carbonitrile Alkylation of the product of example 30a (539 mg) with the product of example 51c (252 mg) was performed according to the method described in example 1a. The residue was purified by preparative HPLC (40→100% acetonitrile). Yield: 363 mg. MS-ESI: $[M+H]^+$=602.4/604.4; anal. HPLC: Rt=15.53 min (diast1), Rt=15.99 min (diast2) (method 1). Diast. ratio: 11:1

EXAMPLE 52

N-[2-Bromo-4-(3-cyano-2-methyl-5-oxo-7-propyl-1,4,5,6,7,8-hexahydro-quinolin-4-yl)-6-ethoxy-phenyl]-2-nitro-benzamide (a). 3-Ethoxy-4-nitro-benzaldehyde At 20° C. iodoethane (3.78 g) was added to a suspension of $K_2CO_3$ (1.09 g) and 3-hydroxy-4-nitro-benzaldehyde (1.0 g) in DMF (5 ml). The reaction mixture was stirred at 70° C. for 18 h, poured into water and then extracted with ethyl acetate. The organic phases were combined, dried ($MgSO_4$) and concentrated in vacuo. The title product was obtained as a yellow solid. Yield: 1.17 g. MS-ESI: $[M+H]^+$=196.

(b). 4-(3-Ethoxy-4-nitro-phenyl)-2-methyl-5-oxo-7-propyl-1,4,5,6,7,8-hexahydro-quinoline-3-carbonitrile The title compound was obtained analogously to example 1b, starting from the product of example 52a (1.16 g), 3-aminocrotonitrile (502 mg) and 5-propylcyclohexane-1,3-dione (920 mg). Yield: 1.24 g. MS-ESI: $[M+H]^+$=396.

(c). 4-(4-Amino-3-ethoxy-phenyl)-2-methyl-5-oxo-7-propyl-1,4,5,6,7,8-hexahydro-quinoline-3-carbonitrile The title compound was obtained analogously to example 19c starting from the product of example 52b (1.2 g). Yield: 1.1 g. MS-ESI: $[M+H]^+$=366.

(d). 4-(4-Amino-3-bromo-5-ethoxy-phenyl)-2-methyl-5-oxo-7-propyl-1,4,5,6,7,8-hexahydro-quinoline-3-carbonitrile At 0° C. a solution of bromine (56 μl) in dichloromethane (5 ml) was added slowly to a mixture of the product example 52c (365 mg) and sodium acetate (89 mg) in acetic acid (10 ml) and dichloromethane (5 ml). The reaction mixture was stirred at 0° C. for 1 h, poured into water and then extracted with dichloromethane. The organic phases were combined, dried (MgSO$_4$) and concentrated in vacuo. The title compound was obtained after flash column chromatography (silica gel, heptane/ethyl acetate (1/4, v/v), R$_f$=0.55). Yield: 1.17 g. MS-ESI: [M+H]$^+$=444/446.

(e). N-[2-Bromo-4-(3-cyano-2-methyl-5-oxo-7-propyl-1,4,5,6,7,8-hexahydro-quinolin-4-yl)-6-ethoxy-phenyl]-2-nitro-benzamide At 20° C., 2-nitro-benzoyl chloride (125 mg) was slowly added to a solution of the product of example 52d (200 mg) and N,N-dimethylaniline (172 µl) in THF (5 ml). The reaction mixture was stirred at 20° C. until total conversion and then poured in sat. NaHCO$_3$ and extracted with ethyl acetate. The organic phases were combined, dried (MgSO$_4$) and concentrated in a vacuo. The title compound was obtained by recrystallization from acetonitrile. Yield: 37 mg. MS-ESI: [M+H]$^+$=593/595; anal. HPLC: Rt=17.98 min (method 2).

EXAMPLE 53

4-[3-Bromo-5-ethoxy-4-(1-trifluoromethanesulfonyl-1H-pyrrol-2-ylmethoxy)-phenyl]-2-methyl-5-oxo-7-propyl-1,4,5,6,7,8-hexahydro-quinoline-3-carbonitrile

(a). 1-Trifluoromethanesulfonyl-1H-pyrrole-2-carbaldehyde

At −78° C. and under a nitrogen atmosphere, trifluoromethanesulfonic anhydride (3.2 ml) was added dropwise to a solution of pyrrole-2-carboxyaldehyde (1 g) and DIPEA (3.67 ml) in dichloromethane (100 ml). After stirring for 5 min at −78° C., the reaction mixture was poured into sat. NaHCO$_3$ (200 ml) and extracted with dichloromethane. The organic layer was separated, washed with water, dried (MgSO$_4$), filtered and concentrated in vacuo. The residue was chromatographed on silica gel in heptane/ethyl acetate=2/1 (v/v) as eluent. Yield: 675 mg.

(b). (1-Trifluoromethanesulfonyl-1H-pyrrol-2-yl)-methanol

The title compound was obtained analogously to example 51b starting from the product of example 53a (300 mg). Yield: 361 mg

(c). 2-Chloromethyl-1-trifluoromethanesulfonyl-1H-pyrrole

The title compound was obtained analogously to example 51c starting from the product of example 53b (361 mg). Yield: 391 mg

(d). 3-Bromo-5-ethoxy-4-(1-trifluoromethanesulfonyl-1H-pyrrol-2-ylmethoxy)-benzaldehyde Alkylation of 3-bromo-5-ethoxy-4-hydroxy benzaldehyde (387 mg) with the product of example 53c (391 mg) was performed according to the method described in example 1a. The residue was chromatographed on silica gel in heptane/ethyl acetate=3/1 (v/v) as eluent. Yield: 208 mg. MS-ESI: [M+H]$^+$=456.2/458.2

(e). 4-[3-Bromo-5-ethoxy-4-(1-trifluoromethanesulfonyl-1H-pyrrol-2-ylmethoxy)phenyl]-2-methyl-5-oxo-7-propyl-1,4,5,6,7,8-hexahydro-quinoline-3-carbonitrile The title compound was obtained analogously to example 1b starting from the product of example 53d (208 mg). The residue was purified by preparative HPLC (20→100% acetonitrile). Yield: 166 mg. MS-ESI: [M+H]$^+$=656.2/658.2; anal. HPLC: Rt=23.99 min (diast1), Rt=24.47 (diast.2) (method 1). Diast. ratio: 5:1.

EXAMPLE 54

4-[2-Bromo-4-(3-cyano-2-methyl-5-oxo-7-propyl-1,4,5,6,7,8-hexahydro-quinolin-4-yl)-6-ethoxy-phenoxymethyl]-N-methyl-benzamidine

(a). 4-[3-Bromo-4-(4-cyano-benzyloxy)-5-ethoxy-phenyl]-2-methyl-5-oxo-7-propyl-1,4,5,6,7,8-hexahydro-quinoline-3-carbonitrile Alkylation of the product of example 30a (2.5 g) with α-bromo-p-tolunitrile (1.21 g) was performed according to the method described in example 30b. The reaction mixture was poured in water and filtered over decalite. The residue was washed with water en dichloromethane. The organic layer was separated, washed with water and brine, dried (MgSO$_4$), filtered and concentrated in vacuo. The residue was chromatographed on silica gel in heptane/ethyl acetate=3/1 (v/v) as eluent. Yield: 2.6 g. MS-ESI: [M+H]$^+$=560/562

(b). 4-[2-Bromo-4-(3-cyano-2-methyl-5-oxo-7-propyl-1,4,5,6,7,8-hexahydro-quinolin-4-yl)-6-ethoxy-phenoxymethyl]-benzimidic acid ethyl ester HCl (g) was bubbled through a solution of the product of example 54a (1.5 g) in ethanol (10 ml) for 2 h. After additional stirring for 2 h, the reaction mixture was concentrated in vacuo. Yield: 1.62 g.

(c). 4-[2-Bromo-4-(3-cyano-2-methyl-5-oxo-7-propyl-1,4,5,6,7,8-hexahydro-quinolin-4-yl)-6-ethoxy-phenoxymethyl]-N-methyl-benzamidine A mixture of the product of example 54b (180 mg), methylamine (126 µl, 8 M in EtOH) and triethylamine (126 µl) in ethanol (1 ml) was stirred for 54 h. The reaction mixture was concentrated in vacuo. The residue was purified by preparative HPLC (10→90% acetonitrile. 0.1% TFA). Yield: 56.5 mg (as TFA salt). MS-ESI: [M+H]$^+$=591/593; anal. HPLC: Rt=17.8 min (method 4).

EXAMPLE 55

2-[2-Bromo-4-(3-cyano-2-methyl-5-oxo-7-propyl-1,4,5,6,7,8-hexahydro-quinolin-4-yl)-6-ethoxy-phenoxymethyl]-pyrrole-1-carboxylic acid tert-butyl ester

(a). 2-Formyl-pyrrole-1-carboxylic acid tert-butyl ester

Bocylation of pyrrole-2-carboxyaldehyde (750 mg) in the presence of NaH (410 mg, 60% dispersion on oil) and Boc-On (2.72 g) was performed according to the method described in example 51a. The residue was chromatographed on silica gel in heptane/ethyl acetate=2/1 (v/v) as eluent. Yield: 196.2 mg.

(b). 2-Hydroxymethyl-pyrrole-1-carboxylic acid tert-butyl ester

Reduction of the product of example 55a (500 mg) with LiBH$_4$ was performed according to the method described in example 51b. The residue was chromatographed on silica gel in heptane/ethyl acetate=2/1 (v/v) as eluent. Yield: 350 mg.

(c). 2-Methanesulfonyloxymethyl-pyrrole-1-carboxylic acid tert-butyl ester

Sulfonylation of the product of example 55b (350 mg) with methanesulfonyl chloride (210 µl) was performed according to the method described in example 51c. The reaction mixture was washed with water, sat. NaHCO$_3$ and brine. The organic layer was separated, dried (MgSO$_4$), filtered and concentrated in vacuo. Yield: 487 mg.

(d). 2-[2-Bromo-4-(3-cyano-2-methyl-5-oxo-7-propyl-1,4,5,6,7,8-hexahydro-quinolin-4-yl)-6-ethoxy-phenoxymethyl]-pyrrole-1-carboxylic acid tert-butyl ester Alkylation of the product of example 30a (787 mg) with the product of example 55c (487 mg) was performed according to the method described in example 1a. The residue was purified by preparative HPLC (20→100% acetonitrile). Yield: 61 mg. MS-ESI: [M+H]$^+$=624.2/626.2; anal. HPLC: Rt=29.35 min (diast1), Rt=29.70 min (diast2) (method 2). Diast. ratio: 4:1.

EXAMPLE 56

4-{3-Bromo-5-ethoxy-4-[(pyridin-3-ylmethyl)-amino]-phenyl}-2-methyl-5-oxo-7-propyl-1,4,5,6,7,8-hexahydro-quinoline-3-carbonitrile At 20° C. pyridine-3-carbaldehyde (210 µl) was added to a solution of the product of example 52d (100 mg) and acetic acid (127 µl) in methanol (4 ml). The reaction mixture was stirred at 20° C. for 16 h and then NaCNBH$_4$ (142 mg) was added. The reaction was stirred at 20° C. for 24 h, poured in water and extracted with ethyl acetate. The title product was obtained via preparative HPLC (0→90% CH$_3$CN, 0.1% TFA).

Yield: 27 mg (as TFA salt). MS-ESI: [M+H]$^+$=535/537; anal. HPLC: Rt=8.56 min (method 2).

EXAMPLE 57

4-[3-Bromo-5-ethoxy-4-(2-nitro-benzylamino)-phenyl]-2-methyl-5-oxo-7-propyl-1,4,5,6,7,8-hexahydro-quinoline-3-carbonitrile The title compound was obtained analogously to example 56, starting from 2-nitro-benzaldehyde (1.93 g) and the product of example 52d (570 mg). The residue was purified by preparative HPLC (0→90% CH$_3$CN). Yield: 610 mg. MS-ESI: [M+H]$^+$=579/581: HPLC: Rt=24.35 min (diast1), Rt=24.85 min (diast2) (method 2). Diast. ratio: 9:1 (HPLC)

EXAMPLE 58

N-(2-{[2-Bromo-4-(3-cyano-2-methyl-5-oxo-7-propyl-1,4,5,6,7,8-hexahydro-quinolin-4-yl)-6-ethoxy-phenylamino]-methyl}-phenyl)-methanesulfonamide (a). 4-[4-(2-Amino-benzylamino)-3-bromo-5-ethoxy-phenyl]-2-methyl-5-oxo-7-propyl-1,4,5,6,7,8-hexahydro-quinoline-3-carbonitrile The title compound was obtained analogously to example 19c, starting from the product of example 57 (550 mg). Yield: 510 mg. [M+H]$^+$=549/551.

(b). N-(2-{[2-Bromo-4-(3-cyano-2-methyl-5-oxo-7-propyl-1,4,5,6,7,8-hexahydro-quinolin-4-yl)-6-ethoxy-phenylamino]-methyl}-phenyl)-methanesulfonamide The title compound was obtained analogously to example 28, starting from the product of example 58a (130 mg) and methanesulfonyl chloride (20 µl). Yield: 31 mg. MS-ESI: [M+H]$^+$=627/629; anal. HPLC: Rt=20.82 min (diast1), Rt=21.35 min (diast2) (method 2). Diast. ratio: 4:1 (HPLC)

EXAMPLE 59

(3-{[2-Bromo-4-(3-cyano-2-methyl-5-oxo-7-propyl-1,4,5,6,7,8-hexahydro-quinolin-4-yl)-6-ethoxy-phenylamino]-methyl}-phenyl)-carbamic acid methyl ester (a). 4-[3-Bromo-5-ethoxy-4-(3-nitro-benzylamino)-phenyl]-2-methyl-5-oxo-7-propyl-1,4,5,6,7,8-hexahydro-quinoline-3-carbonitrile The title compound was obtained analogously to example 56, starting from 3-nitro-benzaldehyde (1.93 g) and the product of example 52d (570 mg). Yield: 630 mg. MS-ESI: [M+H]$^+$=579/581; anal. HPLC: Rt=23.91 min (diast1), Rt=24.32 min (diast2) (method 2). Diast. ratio: 6:1 (HPLC)

(b). 4-[4-(3-Amino-benzylamino)-3-bromo-5-ethoxy-phenyl]-2-methyl-5-oxo-7-propyl-1,4,5,6,7,8-hexahydro-quinoline-3-carbonitrile The title compound was obtained analogously to example 19c, starting from the product of example 59a (570 mg). Yield: 510 mg. [M+H]$^+$=549/551.

(c). (3-{[2-Bromo-4-(3-cyano-2-methyl-5-oxo-7-propyl-1,4,5,6,7,8-hexahydro-quinolin-4-yl)-6-ethoxy-phenylamino]-methyl}-phenyl)-carbamic acid methyl ester The title compound was obtained analogously to example 25, starting from the product of example 59b (130 mg) and methylchloroformate (24 µl). Yield: 29 mg. MS-ESI: [M+H]$^+$= 607/609; anal. HPLC: Rt=17.89 min (method 2).

EXAMPLE 60

2-[2-Bromo-4-(3-cyano-2-methyl-5-oxo-7-propyl-1,
4,5,6,7,8-hexahydro-quinolin-4-yl)-6-ethoxy-phenoxymethyl]-benzamidine; compound with hydrochloric acid (a). 4-[3-Bromo-4-(2-cyano-benzyloxy)-5-ethoxyphenyl]-2-methyl-5-oxo-7-propyl-1,4,5,6,7,8-hexahydro-quinoline-3-carbonitrile Alkylation of the product of example 30a (2.5 g) with α-bromo-o-tolunitrile (1.21 g) was performed according to the method described in example 54a. Yield: 2.44 g. MS-ESI: [M+H]$^+$=560/562

(b.) 2-[2-Bromo-4-(3-cyano-2-methyl-5-oxo-7-propyl-1,4,5,6,7,8-hexahydro-quinolin-4-yl)-6-ethoxy-phenoxymethyl]-benzamidine; compound with hydrochloric acid HCl (g) was bubbled through a solution of the product of example 60a (200 mg) in ethanol (1 ml) for 1 h. After additional stirring for 2 weeks, the reaction mixture was concentrated in vacuo. The residue was dissolved in ethanol and NH$_4$OAc (83 mg) was added. After stirring for 18 h, the reaction mixture was concentrated in vacuo. The residue was chromatographed on silica gel in heptane/ethyl acetate=1/1 (v/v) as eluent. Yield: 17.4 mg (HCl-salt). MS-ESI: [M+H]$^+$= 577/579; anal. HPLC: Rt=16.8 min (diast1) (method 4).

EXAMPLE 61

4-{3-Bromo-5-ethoxy-4-[3-(imino-morpholin-4-ylmethyl)-benzyloxy]-phenyl}-2-methyl-5-oxo-7-propyl-1,4,5,6,7,8-hexahydro-quinoline-3-carbonitrile (a). 4-[3-Bromo-4-(3-cyano-benzyloxy)-5-ethoxyphenyl]-2-methyl-5-oxo-7-propyl-1,4,5,6,7,8-hexahydro-quinoline-3-carbonitrile Alkylation of the product of example 30a (2.5 g) with α-bromo-m-tolunitrile (1.21 g) was performed according to the method described in example 54a. Yield: 2.6 g. MS-ESI: [M+H]$^+$=560/562

(b). 3-[2-Bromo-4-(3-cyano-2-methyl-5-oxo-7-propyl-1,4,5,6,7,8-hexahydro-quinolin-4-yl)-6-ethoxy-phenoxymethyl]-benzimidic acid ethyl ester The title compound was prepared analogously to example 54b, starting from the product of example 61a (1.5 g). Yield: 1.62 g.

(c). 4-{3-Bromo-5-ethoxy-4-[3-(imino-morpholin-4-yl-methyl)-benzyloxy]-phenyl}-2-methyl-5-oxo-7-propyl-1,4,5,6,7,8-hexahydro-quinoline-3-carbonitrile The title compound was prepared analogously to example 54c, starting from the product of example 61b (180 mg) and morpholine (77.8 mg). Yield: 86.7 mg (as TFA salt). MS-ESI: [M+H]$^+$=647/649; anal. HPLC: Rt=17.7 min (method 4).

EXAMPLE 62

4-{3-Bromo-4-[2-(cyclopropylmethyl-amino)-benzyloxy]-5-ethoxy-phenyl}-2-methyl-5-oxo-7-propyl-1,4,5,6,7,8-hexahydro-quinoline-3-carbonitrile (a). N-{2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-2,4-dinitro-benzenesulfonamide 2,4-Dinitro-benzenesulfonyl chloride (3.2 g) and pyridine (3.8 ml) were added to a solution of the product of example 19c (5 g) in dichloromethane (30 ml). After stirring for 3 h, the reaction mixture was poured in water and acidified with 2N HCl. The organic layer was separated and washed with sat. NaHCO$_3$ and brine. The organic layer was separated, dried (MgSO$_4$), filtered and concentrated in vacuo. The residue was chromatographed on silica gel in heptane/ethyl acetate=1/2 (v/v) as eluent. Yield: 5 g. MS-ESI: [M+H]$^+$=780.2/782.2

(b). N-{2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-N-cyclopropylmethyl-2,4-dinitro-benzenesulfonamide Diisopropylazodicarboxylate (102 µl) was added dropwise to a solution of the product of example 62a (200 mg), cyclopropanemethanol (38.2 mg) and triphenylphosphine (134 mg) in THF (6 ml). After stirring for 10 min, the reaction mixture was concentrated in vacuo. The residue was chromatographed on silica gel in heptane/ethyl acetate=1/2 (v/v) as eluent. Yield: 158 mg. ESI-MS: [M+H]$^+$=834.4/836.4

(c). 4-{3-Bromo-4-[2-(cyclopropylmethyl-amino)-benzyloxy]-5-ethoxy-phenyl}-2-methyl-5-oxo-7-propyl-1,4,5,6,7,8-hexahydro-quinoline-3-carbonitrile A mixture of the product of example 62b (158 mg) and propylamine (200 µl) in dichloromethane (10 ml) was stirred for 1 h. The reaction mixture was concentrated in vacuo and the residue was purified by preparative HPLC (10-90% CH$_3$CN). Yield: 72 mg. MS-ESI: [M+H]$^+$=604.4/606.4; anal. HPLC: Rt=21.8 min (diast1), Rt=22.39 min (diast2) (method 1). Diast. ratio: 6:1

EXAMPLE 63

4-{3-Bromo-5-ethoxy-4-[2-(3-methyl-butylamino)-benzyloxy]-phenyl}-2-methyl-5-oxo-7-propyl-1,4,5,6,7,8-hexahydro-quinoline-3-carbonitrile (a). N-{2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-N-(3-methyl-butyl)-2,4-dinitro-benzenesulfonamide The title compound was obtained analogously to example 62b, starting from the product of example 62a (200 mg) and isoamylalcohol (56 µl). Yield: 205 mg. MS-ESI: [M+H]$^+$= 850.4/852.4

(b). 4-{3-Bromo-5-ethoxy-4-[2-(3-methyl-butylamino)-benzyloxy]-phenyl}-2-methyl-5-oxo-7-propyl-1,4,5,6,7,8-hexahydro-quinoline-3-carbonitrile The title compound was prepared analogously to example 62c, starting from the product of compound 63a (205 mg).

Yield: 66.7 mg. MS-ESI: [M+H]$^+$=620.4/622.4; anal. HPLC: Rt=23.61 min (diast1), Rt=24.05 min (diast2) (method 5). Diast. ratio: 5:1

EXAMPLE 64

{2-[2-Bromo-6-ethoxy-4-(2-methyl-3-nitro-5-oxo-7-propyl-1,4,5,6,7,8-hexahydro-quinolin-4-yl)-phenoxymethyl]-phenyl}-carbamic acid methyl ester (a). 1-Nitro-propan-2-one At 0° C. sodium hydride (60% dispersion on oil) (1.28 g) was added to a solution of nitromethane (1.95 g) in THF (25 ml). The reaction mixture was stirred at 20° C. for 30 minutes and then added to a solution of 1-pyrazol-1-yl-ethanone (2.72 g) in THF (25 ml). The reaction mixture was stirred at 60° C. for 18 h. The solid formed was filtered, dissolved in water (50 ml), acidified to pH=3 with 1 M HCl and then extracted several times with ethyl acetate. The organic phases were combined dried (MgSO$_4$) and concentrated. The title product was obtained as a yellow oil. Yield: 2.47 g.

(b). 1-Methyl-2-nitro-vinylamine

A mixture of the product of example 64a (1.6 g) and NH$_4$OAc (1.3 g) in toluene (25 ml) was heated under reflux for 18 h with azeotropic removal of water using a DeanStark apparatus. The reaction mixture was concentrated in vacuo and chromatographed on silica gel in heptane/ethyl acetate=2/1 as eluent. Yield: 10.7 g (c). (2-Hydroxymethyl-phenyl)-carbamic acid methyl ester Reaction of aminobenzylalcohol (3 g) with methylchloroformate (1.9 ml) in the presence of DIPEA (12.8 ml) was performed according to the method described in example 22. The residue was chromatographed on silica gel in dichloromethane/ethyl acetate=25/1 as eluent. Yield: 4.19 g.

(d). (2-Chloromethyl-phenyl)-carbamic acid methyl ester

The title compound was prepared analogously to example 48b starting from the product of example 64c (4.19 g) and thionyl chloride (10 ml). Yield: 1.98 g.

(e). [2-(2-Bromo-6-ethoxy-4-formyl-phenoxymethyl)-phenyl]-carbamic acid methyl ester Alkylation of 3-bromo-5-ethoxy-4-hydroxy benzaldehyde (614 mg) with the product of example 64d (500 mg) was preformed according to the method described in example 1b. Yield: 845 mg.

(f). {2-[2-Bromo-6-ethoxy-4-(2-methyl-3-nitro-5-oxo-7-propyl-1,4,5,6,7,8-hexahydro-quinolin-4-yl)-phenoxymethyl]-phenyl}-carbamic acid methyl ester Reaction of the product of example 64e (100 mg) with the product of example 64b (28 mg) and 5-propylcyclohexane-1,3-dione (41 g) was performed according to the method described in example 1b. The residue was purified by preparative HPLC (10→90% acetonitrile). Yield: 75 mg. MS-ESI: [M+H]$^+$=628/630; anal. HPLC: Rt=26.22 min (diast1), Rt=26.67 min (diast2) (method 2). Diast. ratio: 4:1

EXAMPLE 65

4-[3-Bromo-5-ethoxy-4-(3-methoxy-benzyloxy)-phenyl]-2-methyl-3-nitro-7-propyl-4,6,7,8-tetrahydro-1H-quinolin-5-one (a). 4-(3-Bromo-5-ethoxy-4-hydroxy-phenyl)-2-methyl-3-nitro-7-propyl-4,6,7,8-tetrahydro-1H-quinolin-5-one Reaction of the product of example 64b (1 g) with 3-bromo-5-ethoxy-4-hydroxy benzaldehyde (2.57 g) and 5-propylcyclohexane-1,3-dione (1.61 g) was performed according to the method described in example 1b. The residue was recrystallized from dichloromethane. Yield: 2.8 g. MS-ESI: [M+H]$^+$=465/467

(b). 4-[3-Bromo-5-ethoxy-4-(3-methoxy-benzyloxy)-phenyl]-2-methyl-3-nitro-7-propyl-4,6,7,8-tetrahydro-1H-quinolin-5-one The title compound was obtained analogously to example 30b, starting from the product of example 65a (100 mg) and 1-bromomethyl-3-methoxy-benzene (50 mg).
Yield: 36 mg. MS-ESI: [M+H]$^+$=554/556; anal. HPLC: Rt=27.18 min (diast1), Rt=27.61 min (diast2) (method 2). Diast. ratio: 1:1

EXAMPLE 66

4-[3-Bromo-5-ethoxy-4-(2-methyl-thiazol-4-yl-methoxy)-phenyl]-2-methyl-3-nitro-7-propyl-4,6,7,8-tetrahydro-1H-quinolin-5-one The title compound was obtained analogously to example 30b, starting from 4-chloromethyl-2-methyl-thiazole (37 mg) and the product of example 65a (100 mg).
Yield: 27 mg. MS-ESI: [M+H]$^+$=574/576; anal. HPLC: Rt=22.01 min (diast), Rt=22.50 min (diast2) (method 2). Diast. ratio: 1:1

EXAMPLE 67

{4-[2-Bromo-4-(3-cyano-2-methyl-5-oxo-7-propyl-1,4,5,6,7,8-hexahydro-quinolin-4-yl)-6-ethoxy-phenoxymethyl]-phenyl}-acetic acid methyl ester Alkylation of the product of example 30a (196 mg) with (4-bromomethyl-phenyl)acetic acid methyl ester (107 mg) was performed according to the method described in example 30b. The residue was purified by preparative HPLC (10-90% acetonitrile).
Yield: 116 mg. MS-ESI: [M+H]$^+$=607/609; anal. HPLC: Rt=28.41 min (method 4).

EXAMPLE 68

{4-[2-Bromo-4-(3-cyano-2-methyl-5-oxo-7-propyl-1,4,5,6,7,8-hexahydro-quinolin-4-yl)-6-ethoxy-phenoxymethyl]-phenoxy}-acetic acid (a). 14-[2-Bromo-4-(3-cyano-2-methyl-5-oxo-7-propyl-1,4,5,6,7,8-hexahydro-quinolin-4-yl)-6-ethoxy-phenoxymethyl]-phenoxy-acetic acid methyl ester Alkylation of the product of example 30a (445 mg) with (4-bromomethyl-phenoxy)acetic acid methyl ester (259 mg)

was performed according to the method described in example 67. Yield: 308 mg. MS-ESI: [M+H]$^+$=623/625; anal. HPLC: Rt=23.67 min (method 2).

(b). {4-[2-Bromo-4-(3-cyano-2-methyl-5-oxo-7-propyl-1,4,5,6,7,8-hexahydro-quinolin-4-yl)-6-ethoxy-phenoxymethyl]-phenoxy}-acetic acid Saponification of the product of example 68a (230 mg) was performed according to the method described in example 6c. Yield: 166 mg. MS-ESI: [M+H]$^+$=609/611; anal. HPLC: Rt=19.32 min.

EXAMPLE 69

N-(3-{[2-Bromo-4-(3-cyano-2-methyl-5-oxo-7-propyl-1,4,5,6,7,8-hexahydro-quinolin-4-yl)-6-ethoxy-phenylamino]-methyl}-pyridin-2-yl)-methanesulfonamide (a). N-(3-Cyano-pyridin-2-yl)-methanesulfonamide A mixture of 2-chloro-nicotinonitrile (2 g), H$_2$NSO$_2$Me (1.73 g) and K$_2$CO$_3$ (4.44 g) in DMF (100 ml) was stirred at 100° C. for 18 h. The reaction mixture was concentrated in vacuo. The residue was dissolved in ethyl acetate and washed with water and brine. The organic layer was separated, dried (MgSO$_4$), filtered and concentrated in vacuo. The residue was chromatographed on silica gel in dichloromethane/methanol=98/2 (v/v) as eluent. Yield: 1.32 g. MS-ESI: [M+H]$^+$= 198.2

(b). N-(3-Formyl-pyridin-2-yl)-methanesulfonamide

Raney nickel (2.64 ml, 50% suspension in water) was added to a solution of the product of example 69a (1.32 g) in formic acid (55 ml). After stirring at 100° C. for 3 h, the reaction mixture was filtered over decalite and washed with formic acid. After concentration of the filtrate, the residue was dissolved in ethyl acetate and washed with sat. NaHCO$_3$ and brine. The organic layer was separated, dried (MgSO$_4$), filtered and concentrated in vacuo. The residue was chromatographed on silica gel in heptane/ethyl acetate=2/1 (v/v) as eluent. Yield: 461 mg. MS-ESI: [M+H]$^+$=201.2

(c). N-(3-{[2-Bromo-4-(3-cyano-2-methyl-5-oxo-7-propyl-1,4,5,6,7,8-hexahydro-quinolin-4-yl)-6-ethoxy-phenylamino]-methyl}-pyridin-2-yl)-methanesulfonamide A mixture of the product of example 52d (200 mg), the product of example 69b (99 mg) and acetic acid (129 µl) in methanol (8 ml) was stirred for 18 h followed by addition of NaCNBH$_3$ (141 mg). Stirring was continued for another 4 h. The reaction mixture was diluted with ethyl acetate and washed with water, sat. NaHCO$_3$ and brine. The organic layer was separated, dried (MgSO$_4$), filtered and concentrated in vacuo. The residue was purified by preparative HPLC (10-90% CH$_3$CN). Yield: 145 mg. MS-ESI: [M+H]$^+$=628/630; anal. HPLC: Rt=10.77 min (diast1), Rt=11.17 min (diast2) (method 2). Diast. ratio: 9:1

EXAMPLE 70

4-[3-Bromo-4-(2,5-dimethyl-2H-pyrazol-3-yl-methoxy)-5-ethoxy-phenyl]-2-methyl-3-nitro-7-propyl-4,6,7,8-tetrahydro-1H-quinolin-5-one (a). 5-Chloromethyl-1,3-dimethyl-1H-pyrazole The title compound was prepared analogously to example 48b starting from (2,5-dimethyl-2H-pyrazol-3-yl)-methanol (778 mg) and thionyl chloride (2.35 ml). Yield: 900 mg.

(b). 4-[3-Bromo-4-(2,5-dimethyl-2H-pyrazol-3-yl-methoxy)-5-ethoxy-phenyl]-2-methyl-3-nitro-7-propyl-4,6,7,8-tetrahydro-1H-quinolin-5-one Alkylation of the product of example 65a (100 mg) with the product of example 70a (48 mg) was performed according to the method described in example 30b. The residue was purified by preparative HPLC (10→90% acetonitrile). Yield: 77.3 mg. MS-ESI: [M+H]$^+$=573/575; anal. HPLC: Rt=20.14 min (diast1), Rt=20.64 min (diast2) (method 2). Diast. ratio: 4:1

EXAMPLE 71

N-{2-[2-Bromo-4-(3-cyano-2-methyl-5-oxo-7-propyl-1,4,5,6,7,8-hexahydro-quinolin-4-yl)-6-ethoxy-phenoxymethyl]-5-trifluoromethyl-phenyl}-methanesulfonamide (a). 4-[3-Bromo-5-ethoxy-4-(2-nitro-4-trifluoromethyl-benzyloxy)-phenyl]-2-methyl-5-oxo-7-propyl-1,4,5,6,7,8-hexahydro-quinoline-3-carbonitrile Alkylation of the product of example 30a (778 mg) with 1-chloromethyl-2-nitro-4-trifluoromethyl-benzene (419 mg) was performed according to the method described in example 30b. The residue was chromatographed on silica gel in heptane/ethyl acetate=2/1 (v/v) as eluent. Yield: 493.9 mg. MS-ESI: [M+H]$^+$=648/650

(b). 4-[4-(2-Amino-4-trifluoromethyl-benzyloxy)-3-bromo-5-ethoxy-phenyl]-2-methyl-5-oxo-7-propyl-1,4,5,6,7,8-hexahydro-quinoline-3-carbonitrile Reduction of the product of example 71a (431 mg) with zinc dust (1.08 g) was performed according to the method described in example 19c. Yield: 400 mg. MS-ESI: [M+H]$^+$= 618/620

(c). N-{2-[2-Bromo-4-(3-cyano-2-methyl-5-oxo-7-propyl-1,4,5,6,7,8-hexahydro-quinolin-4-yl)-6-ethoxy-phenoxymethyl]-5-trifluoromethyl-phenyl}-di(methanesulfon)amide A mixture of the product of example 71c (120 mg), methanesulfonyl chloride (23 µl) and triethylamine (81 µl) in dichloromethane (2 ml) was stirred at 40° C. for 54 h. The reaction mixture was concentrated in vacuo. Yield: 150 mg (crude). ESI-MS: [M+H]$^+$=774/776

(d). N-{2-[2-Bromo-4-(3-cyano-2-methyl-5-oxo-7-propyl-1,4,5,6,7,8-hexahydro-quinolin-4-yl)-6-ethoxy-phenoxymethyl]-5-trifluoromethyl-phenyl}-methanesulfonamide A mixture of the crude product of example 71c (150 mg) and 2M NaOH (1 ml) in dioxane (2 ml) was stirred for 18 h.

The reaction mixture was acidified with 0.5N HCl, diluted with ethyl acetate and washed with sat. NaHCO$_3$ and brine. The organic layer was separated, dried (MgSO$_4$), filtered and concentrated in vacuo. The residue was purified by preparative HPLC (10-90% CH$_3$CN). Yield: 32.4 mg. MS-ESI: [M+H]$^+$=696/698; anal. HPLC: Rt=26.7 min (diast1), Rt=27.0 min (diast2) (method 2). Diast. ratio: 1:1

EXAMPLE 72

N-{2-[2-Bromo-4-((4R,7S)-3-cyano-2-methyl-5-oxo-7-propyl-1,4,5,6,7,8-hexahydro-quinolin-4-yl)-6-ethoxy-phenoxymethyl]-4,5-difluoro-phenyl}-methanesulfonamide (a). (1S)—N-[1-(4-Methoxy-phenyl)-ethyl]-3-oxo-butyramide To a solution of (S)-1-(4-methoxy-phenyl)-ethylamine (25 g) in dichloromethane (60 mL) was added TEA (20 g) and DMPA (200 mg). Then a solution of 4-methylene-oxetan-2-one (16.7 g) in dichloromethane (60 ml) was added over a period of 30 minutes and then stirred at 20° C. for 18 h. The mixture was washed with 1M HCl, aq. NaHCO$_3$ and aq. NaCl. The organic layer was dried (MgSO$_4$), filtered and concentrated in vacuo.
Yield: 39.8 g. MS-ESI: [M+H]$^+$=236

(b). (1S)-3-Amino-but-2-enoic acid [1-(4-methoxy-phenyl)-ethyl]-amide

To a suspension of (S)—N-[1-(4-methoxy-phenyl)-ethyl]-3-oxo-butyramide (10 g) in toluene (800 ml) was added at 20° C. ammonium acetate (10 g) and the reaction was heated for 20 h at 100° C. in a Dean Stark system. The mixture was concentrated in vacuo and the product obtained was used without further purification in the following reaction step.

(c). 4-(3-Bromo-5-ethoxy-4-hydroxy-phenyl)-2-methyl-5-oxo-7-propyl-1,4,5,6,7,8-hexahydro-quinoline-3-carboxylic acid (1S)-[1-(4-methoxy-phenyl)-ethyl]-amide A mixture of (S)-3-amino-but-2-enoic acid [1-(4-methoxy-phenyl)-ethyl]-amide (10 g), 3-bromo-5-ethoxy-4-hydroxy-benzaldehyde (10.4 g) and 5-propylcyclohexane-1,3-dione (6.5 g) in ethanol (150 ml) was stirred at 80° C. for 18 hr. The mixture was concentrated in vacuo. The residue was dissolved in toluene (100 ml) and dichloromethane (50 ml) and evaporated until a precipitated formed. The solid obtained was then crystallized in EtOAc.
Yield: 12.9 g. MS-ESI: [M+H]$^+$=597.4/599.4; anal. HPLC R$_t$=16.70 (diast.1) R$_t$=17.55 (diast.2) R$_t$=18.81 (diast.3) R$_t$=19.74 (diast.4) (method 7). Diast. ratio diast.1:diast2:diast3:diast4=10:1:10:1.

(d). (4S,7S)-4-(3-Bromo-5-ethoxy-4-hydroxy-phenyl)-2-methyl-5-oxo-7-propyl-1,4,5,6,7,8-hexahydro-quinoline-3-carboxylic acid (1S)-[1-(4-methoxy-phenyl)-ethyl]-amide The mixture of stereoisomers obtained in Example 72c was then separated by chromatography on silicagel in heptane/ethyl acetate 2/8->0/1 (v/v) as eluent.
Yield: 2.6 g MS-ESI: [M+H]$^+$=597.4/599.4; anal. HPLC Rt=18.81 (diast.3) (method 7). Diast. ratio: 0:0:1:0

(e). (4R,7S)-4-(3-Bromo-5-ethoxy-4-hydroxy-phenyl)-2-methyl-5-oxo-7-propyl-1,4,5,6,7,8-hexahydro-quinoline-3-carbonitrile A solution of (4S,7S)-4-(3-Bromo-5-ethoxy-4-hydroxy-phenyl)-2-methyl-5-oxo-7-propyl-1,4,5,6,7,8-hexahydro-quinoline-3-carboxylic acid [1-(4-methoxy-phenyl)ethyl]-amide (Example 72d, 1.43 g) was dissolved in TFA (30 mL) and stirred at 75° C. for 1 hr. The TFA was evaporated in vacuo and the residue was then dissolved in dichloromethane (30 ml). Triethylamine (1.04 g) and trifluoroacetic acid anhydride (0.95 g) were added dropwise at 0° C. for 15 minutes. The reaction was stirred for 1 hr and the reaction mixture was washed with water (20 ml). The organic layer was dried (MgSO$_4$), filtered, concentrated in vacuo and concentrated. The residue was purified by chromatography on silicagel in heptane/ethyl acetate 1/0->0/1 (v/v) as eluent.
Yield: 777 mg. MS-ESI: [M+H]$^+$=445.4.4/447.4

(f). (4,5-Difluoro-2-nitro-phenyl)-methanol

To a solution of to 4,5-difluoro-2-nitrobenzoic acid (25.9 g) in THF (90 ml), cooled to 0° C., was carefully added borane-tetrahydrofuran complex (319 ml, 1M in THF). After the addition was complete, the mixture was stirred at 60° C. for 3 h. Methanol (150 ml) was added to the mixture at 0° C. and after 10 minutes the mixture was concentrated in vacuo. The residue was poured into water and extracted with ethyl acetate. The organic layer was washed with sat. aq. NaCl, dried (MgSO$_4$), filtered and concentrated in vacuo.
Yield: 24.1 g (g). (4R,7S)-4-[3-Bromo-4-(4,5-difluoro-2-nitro-benzyloxy)-5-ethoxy-phenyl]-2-methyl-5-oxo-7-propyl-1,4,5,6,7,8-hexahydro-quinoline-3-carbonitrile To a mixture of (4,5-difluoro-2-nitro-phenyl)-methanol (Example 72f, 5.1 g), (4R,7S)-4-(3-Bromo-5-ethoxy-4-hydroxy-phenyl)-2-methyl-5-oxo-7-propyl-1,4,5,6,7,8-hexahydro-quinoline-3-carbonitrile (Example 72e, 10.0 g) and polymer-supported triphenylphosphine (13.5 g, 3 mmol/g loading) in THF (500 ml), cooled to 0° C., was added diisopropyl azodicarboxylate (DIAD) (5.3 ml). After 1.5 h, the mixture was filtered and the filtrate was concentrated in vacuo. The residue was purified by chromatography on silicagel in heptane/ethyl acetate 4/1-2/3 (v/v) as eluent.
Yield: 13.5 g. MS-ESI: [M+H]$^+$=616.10/618.10

(h). (4R,7S)-4-[4-(2-Amino-4,5-difluoro-benzyloxy)-3-bromo-5-ethoxy-phenyl]-2-methyl-5-oxo-7-propyl-1,4,5,6,7,8-hexahydro-quinoline-3-carbonitrile A solution of (4R,7S)-4-[3-Bromo-4-(4,5-difluoro-2-nitro-benzyloxy)-5-ethoxy-phenyl]-2-methyl-5-oxo-7-propyl-1,4,5,6,7,8-hexahydro-quinoline-3-carbonitrile (Example 72 g, 10.6 g) and acetic acid (19.6 ml) in THF (400 ml) was cooled to 0° C. Zinc dust (27.6 g) was added in portions under vigorous stirring. The mixture was stirred for 2 h at 0° C. and then filtered. The solids were washed with dichloromethane and the combined filtrates were washed with sat. aq. NaHCO$_3$. The organic layer was dried (MgSO$_4$), filtered and concentrated in vacuo.
Yield: 10.9 g. MS-ESI: [M+H]$^+$=586.05/588.05

(i). N,N-{2-[2-Bromo-4-((4R,7S)-3-cyano-2-methyl-5-oxo-7-propyl-1,4,5,6,7,8-hexahydro-quinolin-4-yl)-6-ethoxy-phenoxymethyl]-4,5-difluoro-phenyl}-bismethanesulfonamide A solution of (4R,7S)-4-[4-(2-Amino-4,5-difluoro-benzyloxy)-3-bromo-5-ethoxy-phenyl]-2-methyl-5-oxo-7-propyl-1,4,5,6,7,8-hexahydro-quinoline-3-carbonitrile (Example 72 h, 10.9 g) and triethylamine (11.9 ml) in dichloromethane (140 ml), cooled to 0° C., was treated with methanesulfonyl chloride (3.3 ml). After stirring for 2 h at 0° C., the mixture was diluted with 0.2N hydrochloric acid and extracted with dichloromethane. The organic layer was washed with sat. aq. NH$_4$Cl, dried (MgSO$_4$), filtered and concentrated in vacuo. The residue was purified by chromatography on silicagel in heptane/ethyl acetate 7/3-2/5 (v/v) as eluent.

Yield: 11.0 g. MS-ESI: [M+H]$^+$=742.08/744.08

(j). N-{2-[2-Bromo-4-((4R,7S)-3-cyano-2-methyl-5-oxo-7-propyl-1,4,5,6,7,8-hexahydro-quinolin-4-yl)-6-ethoxy-phenoxymethyl]-4,5-difluoro-phenyl}-methanesulfonamide N,N-{2-[2-Bromo-4-((4R,7S)-3-cyano-2-methyl-5-oxo-7-propyl-1,4,5,6,7,8-hexahydro-quinolin-4-yl)-6-ethoxy-phenoxymethyl]-4,5-difluoro-phenyl}-bismethanesulfonamide (Example 72 i, 11.0 g) was dissolved in dioxane (190 ml) and treated with 2N NaOH (80 ml). After 2 h the mixture was quenched with 2N hydrochloric acid and extracted with ethyl acetate. The organic layer was washed with sat. aq. NH$_4$Cl, dried (MgSO$_4$), filtered and concentrated in vacuo. The residue was purified by chromatography on silicagel in toluene/acetone 1/0-3/1 (v/v) as eluent.

Yield: 7.98 g. MS-ESI: [M+H]$^+$=664.06/666.06; anal. HPLC Rt=17.18 min (method 8)

Chiral purity: 99.2% (levorotatory or −) (method 9)

EXAMPLE 73

Agonistic Activity of Compounds at the Human FSH Receptor Expressed in CHO Cells Agonist activity of the compounds at the human FSH receptor was tested in Chinese Hamster Ovary (CHO) cells stably transfected with the human FSH receptor and cotransfected with a cAMP responsive element (CRE)/promotor directing the expression of a firefly luciferase reporter gene. Binding of the compound to the Gs coupled FSH receptor will result in an increase of cAMP, which in turn will induce an increased transactivation of the luciferase reporter construct. The luciferase activity was quantified using a luminescence counter. The compounds were tested in the concentration range of 0.1 nM to 10 μM. This assay was used to determine the EC$_{50}$ (concentration of test compound causing half-maximal (50%) luciferase stimulation) and efficacy of the compounds compared to recombinant human FSH. For this, the software program XLfit (Excel version 2.0, built 30, ID Business Solutions Limited) was used.

Compounds of all examples had an activity (EC$_{50}$) of less than 10$^{-6}$ M. Some of the compounds, such as those of examples 1, 3, 5, 7, 11, 15, 17, 22, 23, 24, 25, 34, 38, 39, 42, 50, 51, 54, 56, 58, 62 and 72 showed an EC$_{50}$ of less than 10$^{-8}$ M.

What is claimed is:
1. A 4-phenyl-5-oxo-1,4,5,6,7,8-hexahydroquinoline derivative according to Formula I,

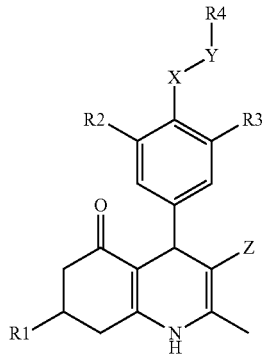

Formula I or a pharmaceutically acceptable salt thereof, wherein
R$^1$ is (1-6C)alkyl, (2-6C)alkenyl or (2-6C)alkynyl;
R$^2$, R$^3$ are independently halogen, (1-4C)alkyl, (2-4C)alkenyl, (2-4C)alkynyl, (1-4C)alkoxy, (3-4C)alkenyloxy or (3-4C)alkynyloxy;
R$^4$ is phenyl or (2-5C)heteroaryl, both substituted with R$^7$ and optionally substituted on the (hetero)aromatic ring with one or more substituents selected from hydroxy, amino, halogen, nitro, trifluoromethyl, cyano, (1-4C)alkyl, (1-4C)alkoxy, (1-4C)alkylthio and (di)(1-4C)alkylamino;
R$^7$ is H, (1-4C)alkylthio, (1-4C)alkylsulfonyl, (di)(1-4C)alkylamino, R$^8$R$^9$-amino, R$^{10}$R$^{11}$-aminocarbonyl, R$^{12}$R$^{13}$-amino(1-4C)alkylcarbonylamino, R$^{14}$R$^{15}$-amino(1-4C)alkyl, R$^{16}$-oxy, R$^{17}$R$^{18}$-aminocarbonyl(1-4C)alkoxy, R$^{19}$-oxy(1-4C)alkyl, R$^{19}$-oxycarbonyl(1-4C)alkyl, R$^{20}$R$^{21}$-aminosulfonyl, R$^{20}$-oxysulfonyl, aminoiminomethyl, (di)(1-4C)alkylaminoiminomethyl or (2-6C)-heterocycloalkyliminomethyl, trifluoromethylsulfonyl; R$^{23}$-oxycarbonyl, R$^{23}$-carbonyl or R$^{23}$R$^{24}$-aminocarbonyl;
R$^8$ is H or (1-4C)alkyl;
R$^9$ is (1-4C)alkylsulfonyl, (1-6C)alkylcarbonyl, (2-6C)alkenylcarbonyl, (2-6C)-alkynylcarbonyl, (3-6C)cycloalkylcarbonyl, (3-6C)cycloalkyl(1-4C)alkylcarbonyl, (1-4C)alkoxycarbonyl, (3-4C)alkenyloxycarbonyl, (3-4C)alkynyloxycarbonyl, (di)(1-4C)alkylaminocarbonyl, (2-6C)heterocycloalkylcarbonyl, (5-8C)alkyl, (3-6C)cycloalkyl, (3-6C)cycloalkyl(1-4C)alkyl, (di)(1-4C)alkylamino(2-4C)alkyl, (2-6C)heterocycloalkyl(2-4C)alkyl or phenylcarbonyl, phenylsulfonyl, phenyl(1-4C)alkoxy(1-4C)alkylcarbonyl, phenyl(1-4C)alkyl, (2-5C)heteroarylcarbonyl, (2-5C)heteroarylsulfonyl, (2-5C)heteroaryl(1-4C)alkyl, optionally substituted on the (hetero)aromatic ring with one or more substituents selected from hydroxy, amino, halogen, nitro, trifluoromethyl, cyano, (1-4C)alkyl, (1-4C)alkoxy or (di)(1-4C)alkylamino;
R$^{10}$ is H or (1-4C)alkyl;
R$^{11}$ is hydroxy(2-4C)alkyl, amino(2-4C)alkyl, (1-4C)alkoxy(2-4C)alkyl or (di)-(1-4C)alkylamino(2-4C)alkyl; or
R$^{10}$R$^{11}$ in R$^{10}$R$^{11}$-aminocarbonyl may be joined in a (4-6C)heterocycloalkenyl ring or a (2-6C)heterocycloalkyl ring substituted with one or more substituents selected from (1-4C)alkyl, (1-4C)alkoxy(1-4C)alkyl and hydroxy(1-4C)alkyl;

$R^{12}$, $R^{13}$ are independently H, (1-6C)alkyl, (2-6C)alkenyl, (2-6C)alkynyl, (3-6C)-cycloalkyl, hydroxy(2-4C)alkyl, (1-4C)alkoxy(2-4C)alkyl, (3-6C)cycloalkyl-(1-4C)alkyl, (2-6C)heterocycloalkyl(1-4C)alkyl, amino(2-4C)alkyl, (di)(1-4C)alkylamino(2-4C)alkyl or phenyl(1-4C)alkyl, (2-5C)heteroaryl(1-4C)alkyl, optionally substituted on the (hetero)aromatic ring with one or more substituents selected from hydroxy, amino, halogen, nitro, trifluoromethyl, cyano, (1-4C)-alkyl, (1-4C)alkoxy and (di)(1-4C)alkylamino; or $R^{12}R^{13}$ in $R^{12}R^{13}$-amino(1-4C)alkylcarbonylamino may be joined in a (4-6C)-heterocycloalkenyl ring or a (2-6C)heterocycloalkyl ring, optionally substituted with one or more substituents selected from (1-4C)alkyl, (1-4C)alkoxy(1-4C)alkyl and hydroxy(1-4C)alkyl;

$R^{14}$, $R^{15}$ are independently H, (1-6C)alkyl, (2-6C)heterocycloalkyl(1-4C)alkyl, (3-6C)cycloalkyl(1-4C)alkyl, (1-4C)alkoxy(2-4C)alkyl, hydroxy(2-4C)alkyl, (di)(1-4C)alkylamino(2-4C)alkyl, amino(2-4C)alkyl, (1-4C)alkoxycarbonyl-(1-4C)alkyl, (1-6C)alkylcarbonyl, (3-6C)cycloalkylcarbonyl, (1-4C)alkoxycarbonyl, (3-4C)alkenyloxycarbonyl, (di)(1-4C)alkylaminocarbonyl, (2-6C)heterocycloalkylcarbonyl or (2-5C)heteroaryl(1-4C)alkyl, phenyl(1-4C)alkyl, (2-5C)heteroarylcarbonyl, phenylcarbonyl, optionally substituted on the (hetero)aromatic ring with one or more substituents selected from hydroxy, amino, halogen, nitro, trifluoromethyl, cyano, (1-4C)alkyl or (1-4C)alkoxy, (di)(1-4C)alkylamino; or $R^{14}R^{15}$ in $R^{14}R^{15}$-amino(1-4C)alkyl may be joined in a (4-6C)heterocycloalkenyl ring or a (2-6C)heterocycloalkyl ring, optionally substituted with one or more substituents selected from (1-4C)alkyl, (1-4C)alkoxy(1-4C)alkyl and hydroxy(1-4C)alkyl;

$R^{16}$ is (2-6C)heterocycloalkyl(1-4C)alkyl, (di)(1-4C)alkylamino(2-4C)alkyl, (2-4C)alkoxy(1-4C)alkyl, hydroxy(2-4C)alkyl, amino(2-4C)alkyl, hydroxycarbonyl(1-4C)alkyl, (1-4C)alkoxycarbonyl(1-4C)alkyl, (1-4C)alkoxycarbonyl, (3-4C)alkenyloxycarbonyl, (3-4C)alkynyloxycarbonyl, (di)(1-4C)alkylaminocarbonyl, (2-6C)heterocycloalkylcarbonyl, or phenyl(1-4C)alkyl, (2-5C)heteroaryl(1-4C)alkyl, optionally substituted on the (hetero)aromatic ring with one or more substituents selected from hydroxy, amino, halogen, nitro, trifluoromethyl, cyano, (1-4C)alkyl, (1-4C)alkoxy and (di)(1-4C)alkylamino;

$R^{17}$, $R^{18}$ are independently H, (1-6C)alkyl, (3-6C)cycloalkyl(1-4C)alkyl, (1-4C)-alkoxy(2-4C)alkyl, hydroxy(2-4C)alkyl, amino(2-4C)alkyl, (di)(1-4C)alkylamino(2-4C)alkyl, (2-6C)heterocycloalkyl(2-4C)alkyl, or phenyl(1-4C)alkyl, (2-5C)heteroaryl(1-4C)alkyl, optionally substituted on the (hetero)aromatic ring with one or more substituents selected from hydroxy, amino, halogen, nitro, trifluoromethyl, cyano, (1-4C)alkyl, (1-4C)alkoxy and (di)(1-4C)alkylamino; or $R^{17}R^{18}$ in $R^{17}R^{18}$-aminocarbonyl(1-4C)alkoxy may be joined in a (4-6C)hetero-cycloalkenyl ring or a (2-6C)heterocycloalkyl ring, optionally substituted with one or more substituents selected from (1-4C)alkyl, (1-4C)alkoxy(1-4C)alkyl and hydroxy(1-4C)alkyl;

$R^{19}$ is H or (1-6C)alkyl;

$R^{20}$, $R^{21}$ are independently H, (1-6C)alkyl, (1-6C)alkenyl, (1-6C)alkynyl or (1-4C)-alkoxy(1-4C)alkyl; or $R^{20}R^{21}$ in $R^{20}R^{21}$-aminosulfonyl may be joined in a (4-6C)heterocycloalkenyl ring or a (2-6C)heterocycloalkyl ring, optionally substituted with one or more substituents selected from (1-4C)alkyl, (1-4C)alkoxy(1-4C)alkyl and hydroxy-(1-4C)alkyl;

X is O or N—$R^{22}$;

Y is $CH_2$, C(O) or $SO_2$;

Z is CN or $NO_2$;

$R^{22}$ is H, (1-4C)alkyl;

$R^{23}$, $R^{24}$ are independently H, (1-4C)alkyl, (2-4C)alkenyl, (2-4C)alkynyl, (3-6C)-cycloalkyl, (3-6C)cycloalkyl(1-4C)alkyl, (2-6C)heterocycloalkyl, (2-6C)heterocycloalkyl(1-4C)alkyl, (1-4C)alkoxycarbonyl(1-4C)alkyl, (di)(1-4C)alkylaminocarbonyl(1-4C)alkyl or phenylaminocarbonyl(1-4C)alkyl, (2-5C)heteroarylaminocarbonyl(1-4C)alkyl, phenyl, (2-5C)heteroaryl, phenyl(1-4C)alkyl, (2-5C)heteroaryl(1-4C)alkyl, optionally substituted at the (hetero)atom with one or more substituents selected from hydroxy, amino, halogen, nitro, trifluoromethyl, cyano, (1-4C)alkyl, (2-4C)alkenyl, (2-4C)alkynyl, (1-4C)alkoxy and (di)(1-4C)-alkylamino; or $R^{23}R^{24}$ in $R^{23}R^{24}$-aminocarbonyl may be joined in a (4-6C)heterocycloalkenyl ring or a (2-6C)heterocycloalkyl ring, optionally substituted with one or more substituents selected from (1-4C)alkyl, (1-4C)alkoxy(1-4C)alkyl and hydroxy-(1-4C)alkyl; with the proviso that the compounds of formula I wherein X is O, $R^4$ is phenyl and $R^7$ is selected from H, (1-4C)alkylthio, (1-4C)alkylsulfonyl, di(1-4C)alkylamino, $R^{23}$-oxycarbonyl, $R^{23}$-carbonyl and $R^{23}R^{24}$-aminocarbonyl, and the compounds of formula I wherein X is O, $R^4$ is (2-5C)heteroaryl and $R^7$ is H or (di)(1-4C)-alkylamino, are excluded.

2. The 4-phenyl-5-oxo-1,4,5,6,7,8-hexahydroquinoline derivative according to claim 1 wherein $R^1$ is (1-6C)alkyl.

3. The 4-phenyl-5-oxo-1,4,5,6,7,8-hexahydroquinoline derivative according to claim 1 wherein $R^2$ is halogen.

4. The 4-phenyl-5-oxo-1,4,5,6,7,8-hexahydroquinoline derivative according to claim 1 wherein $R^3$ is (1-4C)alkoxy.

5. The 4-phenyl-5-oxo-1,4,5,6,7,8-hexahydroquinoline derivative according to claim 1 wherein Z is CN.

6. The 4-phenyl-5-oxo-1,4,5,6,7,8-hexahydroquinoline derivative according to claim 1 wherein X is O.

7. The 4-phenyl-5-oxo-1,4,5,6,7,8-hexahydroquinoline derivative according to claim 1 wherein Y is $CH_2$.

8. The 4-phenyl-5-oxo-1,4,5,6,7,8-hexahydroquinoline derivative according to claim 1 wherein $R^7$ is $R^8R^9$-amino, $R^{10}R^{11}$-aminocarbonyl, $R^{12}R^{13}$-amino-(1-4C)alkylcarbonylamino, $R^{14}R^{15}$-amino(1-4C)alkyl or $R^{17}R^{18}$-aminocarbonyl(1-4C)alkoxy.

9. The 4-phenyl-5-oxo-1,4,5,6,7,8-hexahydroquinoline derivative according to claim 1 wherein $R^8$ is H;

$R^9$ is (1-4C)alkylsulfonyl, (1-6C)alkylcarbonyl, (3-6C)cycloalkylcarbonyl, (1-4C)alkoxycarbonyl, (3-4C)alkenyloxycarbonyl, (di)(1-4C)alkylaminocarbonyl, (2-6C)heterocycloalkylcarbonyl, or phenylcarbonyl, phenyl(1-4C)alkoxy(1-4C)alkylcarbonyl, (2-5C)heteroarylcarbonyl, (2-5C)heteroarylsulfonyl or (2-5C)heteroaryl(1-4C)alkyl, optionally substituted on the (hetero)aromatic ring with one or more substituents selected from, halogen or (1-4C)alkoxy;

$R^{10}$ is H or (1-4C)alkyl;

$R^{11}$ is hydroxy(2-4C)alkyl, amino(2-4C)alkyl, (1-4C)alkoxy(2-4C)alkyl or (di)-(1-4C)alkylamino(2-4C)alkyl; or $R^{10}R^{11}$ in $R^{10}R^{11}$-aminocarbonyl may be joined in a (4-6C)heterocycloalkenyl ring or a (2-6C)heterocycloalkyl ring, optionally substituted with one or more substituents selected from (1-4C)alkyl;

$R^{12}$, $R^{13}$ are independently H, (1-6C)alkyl, (3-6C)cycloalkyl, hydroxy(2-4C)alkyl, (1-4C)alkoxy(2-4C)alkyl, (2-6C)heterocycloalkyl(1-4C)alkyl or (di)-(1-4C)alkylamino(2-4C)alkyl or phenyl(1-4C)alkyl or (2-5C)heteroaryl(1-4C)alkyl, optionally substituted on the (hetero)aromatic ring with one or more substituents selected from halogen; or $R^{12}R^{13}$ in $R^{12}R^{13}$-amino(1-4C)alkylcarbonylamino may be joined in a (4-6C)-heterocycloalkenyl ring or a (2-6C) heterocycloalkyl ring, optionally substituted with one or more substituents selected from (1-4C)alkyl or hydroxy (1-4C)alkyl; $R^{14}$, $R^{15}$ are independently H, (1-6C)alkyl, hydroxy(2-4C)alkyl, (1-4C)alkoxycarbonyl(1-4C)alkyl, (1-6C)alkylcarbonyl, (3-6C)cycloalkylcarbonyl, (1-4C)alkoxycarbonyl, (2-5C)heteroaryl(1-4C)alkyl, (2-5C)heteroarylcarbonyl or phenylcarbonyl;

$R^{16}$ is (2-6C)heterocycloalkyl(1-4C)alkyl, (di)(1-4C)alkylamino(2-4C)alkyl, (2-4C)alkoxy(1-4C)alkyl, hydroxycarbonyl(1-4C)alkyl, (1-4C)alkoxycarbonyl-(1-4C)alkyl; or phenyl(1-4C)alkyl or (2-5C)heteroaryl(1-4C)alkyl, optionally substituted on the (hetero)aromatic ring with one or more substituents selected from halogen or (1-4C)alkoxy;

$R^{17}$, $R^{18}$ are independently H, (1-6C)alkyl, (3-6C)cycloalkyl(1-4C)alkyl, (1-4C)-alkoxy(2-4C)alkyl or (2-6C)heterocycloalkyl(2-4C)alkyl; or phenyl(1-4C)alkyl or (2-5C)heteroaryl(1-4C)alkyl, optionally substituted on the (hetero)aromatic ring with one or more substituents selected from halogen; or $R^{17}R^{18}$ in $R^{17}R^{18}$-aminocarbonyl(1-4C)alkoxy may be joined in a (4-6C)hetero-cycloalkenyl ring or a (2-6C) heterocycloalkyl ring, optionally substituted with one or more substituents selected from (1-4C)alkyl or hydroxy (1-4C)alkyl.

10. The 4-phenyl-5-oxo-1,4,5,6,7,8-hexahydroquinoline derivative according to claim 8 wherein $R^7$ is $R^8R^9$-amino.

11. The 4-phenyl-5-oxo-1,4,5,6,7,8-hexahydroquinoline derivative according to claim 10 wherein $R^8$ is H and $R^9$ is (1-4C)alkylsulfonyl.

12. The 4-phenyl-5-oxo-1,4,5,6,7,8-hexahydroquinoline derivative or a pharmaceutically acceptable salt thereof according to claim 1 selected from the group of N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-3,4,5-trimethoxy-benzamide;

N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-2-[(pyridin-4-ylmethyl)-amino]-acetamide;

N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-2-[4-(2-hydroxy-ethyl)-piperazin-1-yl]-acetamide;

4-{3-Bromo-4-[3-(3,6-dihydro-2H-pyridine-1-carbonyl)-benzyloxy]-5-ethoxy-phenyl}-2-methyl-5-oxo-7-propyl-1,4,5,6,7,8-hexahydro-quinoline-3-carbonitrile;

3-[Bis-(2-methoxy-ethyl)-amino]-N-{3-[2-bromo-4-(3-cyano-2-methyl-5-oxo-7-propyl-1,4,5,6,7,8-hexahydro-quinolin-4-yl)-6-ethoxy-phenoxymethyl]-phenyl}-propionamide;

2-{3-[2-Bromo-4-(3-cyano-2-methyl-5-oxo-7-propyl-1,4,5,6,7,8-hexahydro-quinolin-4-yl)-6-ethoxy-phenoxymethyl]-phenoxy}-N,N-dimethyl-acetamide;

4-{3-Bromo-5-ethoxy-4-[3-(2-morpholin-4-yl-2-oxoethoxy)-benzyloxy]-phenyl}-2-methyl-5-oxo-7-propyl-1,4,5,6,7,8-hexahydro-quinoline-3-carbonitrile;

Furan-2-carboxylic acid {2-[2-bromo-4-(3-cyano-2-methyl-5-oxo-7-propyl-1,4,5,6,7,8-hexahydro-quinolin-4-yl)-6-ethoxy-phenoxymethyl]-phenyl}-amide;

N-{2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-acrylamide;

Cyclopropanecarboxylic acid {2-[2-bromo-4-(3-cyano-2-methyl-5-oxo-7-propyl-1,4,5,6,7,8-hexahydro-quinolin-4-yl)-6-ethoxy-phenoxymethyl]-phenyl}-amide;

2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-carbamic acid methyl ester;

1-{2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-3-methyl-urea {3-[2-Bromo-4-(3-cyano-2-methyl-5-oxo-7-propyl-1,4,5,6,7,8-hexahydro-quinolin-4-yl)-6-ethoxy-phenoxymethyl]-pyridin-2-yl}-carbamic acid methyl ester 4-(3-Bromo-5-ethoxy-4-{3-[(1H-imidazol-4-ylmethyl)-amino]-benzyloxy}-phenyl)-2-methyl-5-oxo-7-propyl-1,4,5,6,7,8-hexahydro-quinoline-3-carbonitrile;

N-{2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-methanesulfonamide;

{4-[2-Bromo-4-(3-cyano-2-methyl-5-oxo-7-propyl-1,4,5,6,7,8-hexahydro-quinolin-4-yl)-6-ethoxy-phenoxymethyl]-phenyl}-carbamic acid allyl ester;

4-[3-Bromo-5-ethoxy-4-(1-methanesulfonyl-1H-pyrrol-2-ylmethoxy)-phenyl]-2-methyl-5-oxo-7-propyl-1,4,5,6,7,8-hexahydro-quinoline-3-carbonitrile;

4-[2-Bromo-4-(3-cyano-2-methyl-5-oxo-7-propyl-1,4,5,6,7,8-hexahydro-quinolin-4-yl)-6-ethoxy-phenoxymethyl]-N-methyl-benzamidine;

4-{3-Bromo-5-ethoxy-4-[(pyridin-3-ylmethyl)-amino]-phenyl}-2-methyl-5-oxo-7-propyl-1,4,5,6,7,8-hexahydro-quinoline-3-carbonitrile;

N-(2-{[2-Bromo-4-(3-cyano-2-methyl-5-oxo-7-propyl-1,4,5,6,7,8-hexahydro-quinolin-4-yl)-6-ethoxy-phenylamino]-methyl}-phenyl)-methanesulfonamide;

4-{3-Bromo-4-[2-(cyclopropylmethyl-amino)-benzyloxy]-5-ethoxy-phenyl}-2-methyl-5-oxo-7-propyl-1,4,5,6,7,8-hexahydro-quinoline-3-carbonitrile; or N-{2-[2-Bromo-4-((4R,7S)-3-cyano-2-methyl-5-oxo-7-propyl-1,4,5,6,7,8-hexahydro-quinolin-4-yl)-6-ethoxy-phenoxymethyl]-4,5-difluoro-phenyl}-methanesulfonamide.

13. A pharmaceutical composition comprising a 4-phenyl-5-oxo-1,4,5,6,7,8-hexahydroquinoline derivative or a pharmaceutically acceptable salt thereof according to claim 1, and pharmaceutically suitable auxiliaries.

14. The pharmaceutical composition of claim 13 wherein the 4-phenyl-5-oxo-1,4,5,6,7,8-hexahydroquinoline derivative is selected from N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-3,4,5-trimethoxy-benzamide;

N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-2-[(pyridin-4-ylmethyl)-amino]-acetamide;

N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-2-[4-(2-hydroxy-ethyl)-piperazin-1-yl]-acetamide;

4-{3-Bromo-4-[3-(3,6-dihydro-2H-pyridine-1-carbonyl)-benzyloxy]-5-ethoxy-phenyl}-2-methyl-5-oxo-7-propyl-1,4,5,6,7,8-hexahydro-quinoline-3-carbonitrile;

3-[Bis-(2-methoxy-ethyl)-amino]-N-{3-[2-bromo-4-(3-cyano-2-methyl-5-oxo-7-propyl-1,4,5,6,7,8-hexahydro-quinolin-4-yl)-6-ethoxy-phenoxymethyl]-phenyl}-propionamide;

2-{3-[2-Bromo-4-(3-cyano-2-methyl-5-oxo-7-propyl-1,4,5,6,7,8-hexahydro-quinolin-4-yl)-6-ethoxy-phenoxymethyl]-phenoxy}-N,N-dimethyl-acetamide;

4-{3-Bromo-5-ethoxy-4-[3-(2-morpholin-4-yl-2-oxo-ethoxy)-benzyloxy]-phenyl}-2-methyl-5-oxo-7-propyl-1,4,5,6,7,8-hexahydro-quinoline-3-carbonitrile;

Furan-2-carboxylic acid {2-[2-bromo-4-(3-cyano-2-methyl-5-oxo-7-propyl-1,4,5,6,7,8-hexahydro-quinolin-4-yl)-6-ethoxy-phenoxymethyl]-phenyl}-amide;

N-{2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-acrylamide;

Cyclopropanecarboxylic acid {2-[2-bromo-4-(3-cyano-2-methyl-5-oxo-7-propyl-1,4,5,6,7,8-hexahydro-quinolin-4-yl)-6-ethoxy-phenoxymethyl]-phenyl}-amide;

2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-carbamic acid methyl ester;

1-{2-[2-Bromo-4-(3-cyano-2-methyl-5-oxo-7-propyl-1,4,5,6,7,8-hexahydro-quinolin-4-yl)-6-ethoxy-phenoxymethyl]-phenyl}-3-methyl-urea {3-[2-Bromo-4-(3-cyano-2-methyl-5-oxo-7-propyl-1,4,5,6,7,8-hexahydro-quinolin-4-yl)-6-ethoxy-phenoxymethyl]-pyridin-2-yl}-carbamic acid methyl ester 4-(3-Bromo-5-ethoxy-4-{3-[(1H-imidazol-4-ylmethyl)-amino]-benzyloxy}-phenyl)-2-methyl-5-oxo-7-propyl-1,4,5,6,7,8-hexahydro-quinoline-3-carbonitrile;

N-{3-[2-Bromo-4-(3-cyano-2-methyl-5-oxo-7-propyl-1,4,5,6,7,8-hexahydro-quinolin-4-yl)-6-ethoxy-phenoxymethyl]-phenyl}-methanesulfonamide;

{4-[2-Bromo-4-(3-cyano-2-methyl-5-oxo-7-propyl-1,4,5,6,7,8-hexahydro-quinolin-4-yl)-6-ethoxy-phenoxymethyl]-phenyl}-carbamic acid allyl ester;

4-[3-Bromo-5-ethoxy-4-(1-methanesulfonyl-1H-pyrrol-2-ylmethoxy)-phenyl]-2-methyl-5-oxo-7-propyl-1,4,5,6,7,8-hexahydro-quinoline-3-carbonitrile;

4-[2-Bromo-4-(3-cyano-2-methyl-5-oxo-7-propyl-1,4,5,6,7,8-hexahydro-quinolin-4-yl)-6-ethoxy-phenoxymethyl]-N-methyl-benzamidine;

4-{3-Bromo-5-ethoxy-4-[(pyridin-3-ylmethyl)-amino]-phenyl}-2-methyl-5-oxo-7-propyl-1,4,5,6,7,8-hexahydro-quinoline-3-carbonitrile;

N-(2-{[2-Bromo-4-(3-cyano-2-methyl-5-oxo-7-propyl-1,4,5,6,7,8-hexahydro-quinolin-4-yl)-6-ethoxy-phenylamino]-methyl}-phenyl)-methanesulfonamide;

4-{3-Bromo-4-[2-(cyclopropylmethyl-amino)-benzyloxy]-5-ethoxy-phenyl}-2-methyl-5-oxo-7-propyl-1,4,5,6,7,8-hexahydro-quinoline-3-carbonitrile; or N-{2-[2-Bromo-4-((4R,7S)-3-cyano-2-methyl-5-oxo-7-propyl-1,4,5,6,7,8-hexahydro-quinolin-4-yl)-6-ethoxy-phenoxymethyl]-4,5-difluoro-phenyl}-methanesulfonamide, or a pharmaceutically acceptable salt thereof.

* * * * *